(12) United States Patent
Pal et al.

(10) Patent No.: US 6,686,390 B2
(45) Date of Patent: Feb. 3, 2004

(54) COMPOUNDS HAVING ANTIINFLAMATORY ACTIVITY: PROCESS FOR THEIR PREPARATION AND PHARMACEUTICAL COMPOSITIONS CONTAINING THEM

(75) Inventors: Manojit Pal, Hyderabad (IN); Koteswar Rao Yeleswarapu, Hyderabad (IN); Rajagopalan Ramanujam, Hyderabad (IN); Parimal Misra, Hyderabad (IN); Prem Kumar Mamnoor, Hyderabad (IN); Seshagiri Rao Casturi, Hyderabad (IN)

(73) Assignee: Dr. Reddy's Laboratories Limited, Hyderabad (IN)

( * ) Notice: Subject to any disclaimer, the term of this patent is extended or adjusted under 35 U.S.C. 154(b) by 255 days.

(21) Appl. No.: 09/861,903

(22) Filed: May 21, 2001

(65) Prior Publication Data

US 2002/0032230 A1 Mar. 14, 2002

(30) Foreign Application Priority Data

May 22, 2000 (IN) ..................................... 388/MAS/2000
Jun. 8, 2000 (IN) ..................................... 436/MAS/2000

(51) Int. Cl.$^7$ ......................... A61K 31/34; A61K 31/38
(52) U.S. Cl. .................... 514/473; 514/231.5; 514/443; 549/53; 549/295; 544/152
(58) Field of Search ............................ 514/473, 231.5, 514/443; 549/295, 53; 544/152

Primary Examiner—Amelia Owen
(74) Attorney, Agent, or Firm—Ladas & Parry

(57) ABSTRACT

The present invention relates to novel heterocyclic compounds of the general formula (I), their derivatives, their analogs, their tautomeric forms, their stereoisomers, their regioisomers, their polymorphs, their pharmaceutically acceptable salts, their pharmaceutically acceptable solvates and pharmaceutically acceptable compositions containing them.

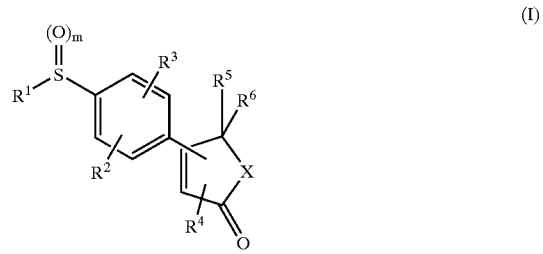

(I)

49 Claims, No Drawings

COMPOUNDS HAVING ANTIINFLAMATORY ACTIVITY: PROCESS FOR THEIR PREPARATION AND PHARMACEUTICAL COMPOSITIONS CONTAINING THEM

FIELD OF INVENTION

The present invention relates to novel anti-inflammatory compounds, their derivatives, their analogs, their tautomeric forms, their stereoisomers, their regioisomers, their polymorphs, their pharmaceutically acceptable salts, their pharmaceutically acceptable solvates and pharmaceutically acceptable compositions containing them. More particularly, the present invention relates to novel heterocyclic compounds of the general formula (I), their derivatives, their analogs, their tautomeric forms, their stereoisomers, their regioisomers, their polymorphs, their pharmaceutically acceptable salts, their pharmaceutically acceptable solvates and pharmaceutically acceptable compositions containing them.

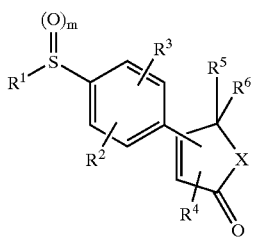

(I)

wherein $R^1$ represents amino or substituted or unsubstituted groups selected from alkyl, alkylamino, acylamino, cycloalkyl, cyclicamino, carboethoxycarbonylalkyl, hydrazino, hydrazido, aminoacid residue, aryl, heteroaryl or $-N=CR(NR)_2$ where R represents hydrogen or lower alkyl group; $R^2$ represents halogen, hydroxy, cyano, nitro, azido, formyl, oximealkyl, thio or substituted or unsubstituted groups selected from amino, alkyl, alkoxy, hydrazino, hydrazinoalkyl, hydrazido, hydrazidoalkyl, aminoacid residue, aminoacid residuealkyl, acyl, carbonyloxyalkyl, haloalkyl, aminoalkyl, haloalkoxy, hydroxyalkyl, alkoxyalkyl, thioalkyl, alkylthio, alkylsulfinyl, alkylsulfonyl, aryl, aralkyl, aryloxy, aralkoxy, aryloxyalkyl, aralkoxyalkyl, carboxamidoalkyl, carbonylaminoalkyl groups or when the groups $-S(=O)_m-R^1$ and $R^2$ are present on adjacent carbon atoms, $R^1$ and $R^2$ together with atoms to which they are attached may also form a substituted or unsubstituted 5–7 membered cyclic structure containing carbon atoms, a sulfur atom and may optionally contain one or two heteroatoms selected from O, S or N; $R^3$ represents hydrogen, halogen atom, hydroxy, nitro, cyano, azido or substituted or unsubstituted groups selected from hydrazino, hydrazinoalkyl, hydrazido, hydrazidoalkyl, aminoacid residues, alkyl, alkoxy, hydroxyalkyl, alkoxyalkyl, acylamino or amino groups; $R^4$ and $R^5$ may be same or different and independently represent hydrogen, halogen, hydroxy, cyano, nitro, thio, hydroxylamino, substituted or unsubstituted groups selected from alkyl, alkoxy, acyl, acyloxy, amino, hydrazino, hydrazinoalkyl, hydrazido, hydrazidoalkyl, aminoacid residues, aminoacyl, carboxyalkyl, carboxyalkenyl, aryl, aryloxy, aralkyl, aralkoxy, alkoxycarbonyl, aryloxycarbonyl, aralkoxycarbonyl, heteroaryl, heteroaryloxy, heteroaralkyl, heteroaralkoxy, heteroarylcarbonyl, heteroaryloxycarbonyl, heteroaralkylcarbonyl, heteroaralkoxycarbonyl, heterocyclylcarbonyl, aminocarbonyl, aminocarbonylalkyl, carbonylamino, cycloalkylacylamino, alkylaminoalkoxy, alkylaminoacyl, carboxylic acid or its derivatives, saturated or partially saturated or aromatic single or fused 5 to 7 membered carbocycle ring or saturated or partially saturated or aromatic, single or fused 5 to 7 membered heterocycle ring; $R^6$ represents hydrogen, halogen, hydroxy, amino, cyano, nitro, thio, hydroxylamino or unsubstituted or substituted groups selected from alkyl, alkoxy, carboxyalkyl; the furanone ring may be fused with $R^4$ wherever possible; $R^5$ and $R^6$ together may represent $=C(R^a)(R^b)$, where $R^a$ and $R^b$ may be same or different and independently represent hydrogen, substituted or unsubstituted $(C_1-C_6)$alkyl or aryl; $=O$ or $=NR^7$ where $R^7$ represents hydrogen, aryl or heteroaryl group; X represents oxygen or $NR^8$, where $R^8$ represents hydrogen or substituted or unsubstituted groups selected from $(C_1-C_6)$alkyl, aryl, aralkyl, heteroaryl, heteroaralkyl, aralkenoyl, aralkanoyl and m is an integer in the range of 0–2.

The present invention also relates to a process for the preparation of the above said novel compounds, their analogs, their derivatives, their tautomeric forms, their stereoisomers, their regioisomers, their polymorphs, their pharmaceutically acceptable salts, pharmaceutically acceptable solvates and pharmaceutical compositions containing them.

The present invention also relates to novel intermediates, process for their preparation and their use in the preparation of compounds of formula (I).

The compounds of general formula (I) are useful as antiinflammatory, analgesic, antipyretic, antiarthritic, antibacterial, anticancer agents or for treating Alzheimer diseases. The compounds of the present invention are also useful for the treatment of diseases of human or animals such as pain, fever or inflammation. Compounds of formula (I) also inhibit prostanoid-induced smooth muscle contraction by preventing the synthesis of contractile prostanoids and hence may be of use in the treatment of dysmenorrhea, premature labor and asthma. The compounds of the present invention are useful for treatment of pain, fever, and inflammation related to common cold, influenza, viral infections. The compounds of the present invention can be used for the treatment of arthritis such as rheumatoid arthritis, osteoarthritis, gouty arthritis, juvenile arthritis, spondylo arthritis; systemic lupus erythematosus, skin inflammation disorders such as eczema, burns, dermatitis, psoriasis; low back and neck pain, head ache, tooth ache, sprains, strains, myostis, neuralgia, synovitis, bursitis, tendinitis, injuries following surgical and dental procedures, post-operative inflammation including ophthalmic surgery such as cataract and refractive surgery.

The compounds of general formula (I) are also useful for the treatment of dysmenorrhoea, premature labour, asthma and bronchitis, gastrointestinal conditions such as inflammatory bowel disease, Crohn's disease, gastritis, irritable bowel syndrome, ulcerative colitis, diverticulitis, regional enteritis, peptic ulcers. These compounds may also be useful for treating inflammation in diseases such as vascular diseases, migraine head aches, periarteritis nodosa, thyroiditis, aplastic anemia, Behcat's syndrome, Hodgkin's diseases, scleroderma, myasthenia gravies, sarcoidosis, nephrotic syndrome, Type I diabetes, polymyositis, conjunctivitis, gingivitis, myocardial ischaemia, nephritis, swelling after injury, hypersensitivity and the like. The compounds of the present inventions are useful in the treatment of allergic rhinitis, respiratory distress syndrome, endotoxin shock syndrome, atherosclerosis, and central nervous system damage resulting from stroke, ischaemia and trauma; pulmonary inflammation such as in the case of viral infections and cystic fibrosis; ophthalmic diseases such as retinitis, retinopathy, uveitis, ocular photophobia and acute injury to eye tissues. The compounds of general formula (I) are also useful for treating central nervous system disorders such as cortical dementia (Alzheimer's diseases), useful for treatment of pain not limited to dental pain, muscular pain, pain from cancer, postoperative pain, and useful for the treatment of diseases where NSAIDS are used with the benefit of having significantly less side effects.

The compounds of general formula (I) are cyclooxygenase inhibitors and are therefore useful to treat the cyclooxygenase mediated diseases. The compounds of formula (I) are also useful for the treatment of mammals not limited to human beings such as horses, dogs, cats, sheep, pigs etc., and also for treating rats, mice, rabbits etc. The compounds of formula (I) may also be used in cotherapies for inflammation, Alzheimer's disease or cancer, in place of, or together with the conventional therapies.

The compounds of the general formula (I) are useful as partial or complete substitute for NSAIDS in compositions or preparations wherein they are presently coadministered with other agents or ingredients. The present invention also comprises pharmaceutical compositions for treating cyclooxygenase mediated diseases as defined earlier, comprising a non-toxic therapeutically effective amount of the compound of formula (I) as defined above and pharmaceutically acceptable carrier optionally containing one or more ingredients such as another analgesic agent like acetaminophen, phenacetin, a potentiator like caffeine, a $H_2$ antagonist, aluminum or magnesium hydroxide, simethicone, a decongestant such as phenylephrine, phenyl propanolamine, pseudophedrine, oxymetazoline, epinephrine, nephazoline, propylhexadrine or leavo-desoxyephedrine, xylomatezoline, a sedating or non sedating antihistamine, an antitussive such as dextromethorphan, carbetapentane, caramiphen, hydrocodeine and codeine and the like, or a diuretic agent. The present invention also comprises a method of treatment of cyclooxygenase mediated diseases consisting of administering a patient in need thereof, a nontoxic therapeutically effective amount of compound of formula (I) or pharmaceutical composition described above.

BACKGROUND OF INVENTION

Nonsteroidal anti-inflammatory drugs (NSAIDS) are widely used in the treatments of arthritis and pain. These agents act by inhibiting the production of prostaglandin, which plays an important role in the inflammation process. The prostaglandin synthesis is inhibited by blocking the enzyme cyclooxygenase (COX) (Vane J. R. Nature [New Biol.] 1971, 231–232). However, these NSAIDS while reducing the prostaglandin induced inflammation and associated symptoms, have also been found to affect prostaglandin regulated other beneficial processes causing side effects [Allison M. C, et. al., J. Med. 1992, 327, 749]. The side effects showed by NSAIDS are gastrointestinal ulceration and intolerance, blockade of platelet aggregation, inhibition of uterine, motility, inhibition of prostaglandin mediated renal function and hypersensitivity reactions.

Recently, it has been discovered that two isoforms of cyclooxygenase exist enzyme viz., COX-1 and COX-2. While COX-1 is constitutive isoform found in blood vessels, stomach and kidney, COX-2 is induced during inflammation. Therefore, selective inhibition of COX-2 enzyme would be useful in treating inflammation without causing side effects due to inhibition of COX-1.

Alternatively Leukotriens also are mediators of inflammation and related disorders. The leukotriens (LTB4, LTC4, LTD4 etc.,) are produced by the 5-lipoxygenase mediated oxidation of arachidonic acid. Hence inhibition of 5-lipoxygenase (5-LO) enzyme would also be useful in treating inflammation and related disorders. It is therefore possible to treat inflammation with agents which can selectively inhibit COX-2 or 5-LO or both without causing the potential side effects caused by chronic treatment with common NSAIDS.

Recently it has been shown that there is increased expression of COX-2 in colon tumors. Therefore, agents that can inhibit COX-2 can also be used in the treatment of cancer.

Studies have shown that the brain tissues of patients of Alzheimer's disease often have high levels of COX-2. This indicates the usefulness of COX-2 inhibitors in the treatment of Alzheimer's disease and in enhancing the memory.

A few heterocyclic compounds, their derivatives, and their analogs have been reported to be useful in the treatment of inflammation. Some of such compounds described in the prior art are outlined below:

(i) International patent application No. WO 97/34882 discloses compounds of general formula (IIa)

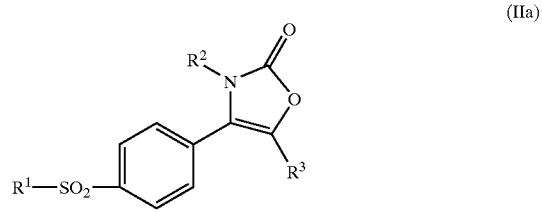

(IIa)

wherein $R^1$ is an alkyl or $NR^4R^5$ group, wherein $R^4$ and $R^5$ each independently is hydrogen or an alkyl or benzyl group; $R^2$ is a naphthyl, tetrahydronaphthyl, unsubstituted phenyl or phenyl group, substituted by from 1 to 3 halogen atoms, alkyl, hydroxy, alkoxy or trifluoromethyl groups and $R^3$ is hydrogen or an alkyl group.

An example of these compounds is shown in formula (IIb)

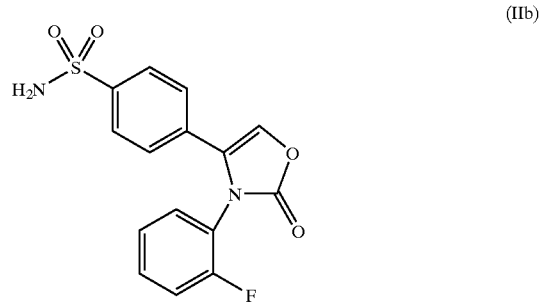

(IIb)

DE patent No. 19753463 discloses compounds of formula (IIc)

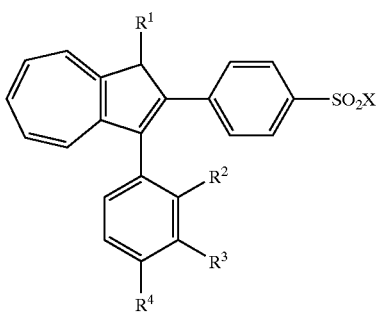

(IIc)

wherein $R^1$ represents hydrogen, alkoxycarbonyl, carboxy, halogen, alkyl, phenyl or alkanoyl; $R^2$, $R^3$ and $R^4$ represents hydrogen, alkyl, alkoxy or halogen; X represents alkyl or $NH_2$.

An example of these compounds is shown in formula (IId)

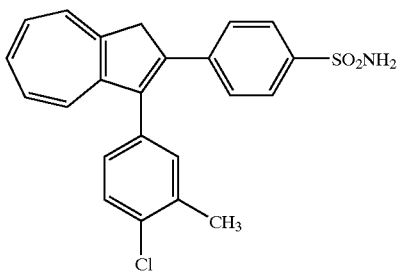

(IId)

(iii) International patent application No. WO 95/00501 discloses compounds of formula (IIe)

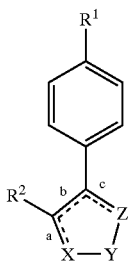

(IIe)

wherein X—Y—Z— is selected from the group consisting of —$CH_2CH_2CH_2$—, —$C(O)CH_2CH_2$—, —$CH_2CH_2C(O)$—, $CR^5(R^{5'})$—O—C(O)—, —C(O)—O—$CR^5(R^{5'})$—, $CH_2$—$NR^3$—$CH_2$—, $CR^5(R^{5'})$—$NR^3$—C(O)—, —$CR^4$=$CR^{4'}$—S—, —S—$CR^4$=$CR^{4'}$—, —S—N=CH—, —CH=N—S—, —N=$CR^4$—O—, —O—$CR^4$=N—, —N=$CR^4$—NH—, —N=$CR^4$—S—, —S—$CR^4$=N—, —C(O)—$NR^3$—$CR^5(R^{5'})$—, —$NR^3$—CH=CH— provided $R^1$ is other than —$S(O)_2Me$, —CH=CH—$NR^3$— provided R is other than —$S(O)_2Me$; when side b is a double bond and sides a and c are single bonds and X—Y—Z— is selected from the group consisting of =CH—O—CH=, =CH—$NR^3$—CH=, =N—S—CH=, =CH—S—N=, =N—O—CH=, =CH—O—N=, =N—S—N=, =N—O—N=, when sides a and c are double bonds and side b is a single bond; $R^1$ is selected from the group consisting of $S(O)_2CH_3$, $S(O)_2NH_2$, $S(O)_2NHC(O)CF_3$, $S(O)(NH)CH_3$, $S(O)(NH)NH_2$, $S(O)(NH)NHC(O)CF_3$, $P(O)(CH_3)OH$ and $P(O)(CH_3)NH_2$; $R^2$ is selected from the group consisting of ($C_1$-$C_6$)alkyl; ($C_3$-$C_7$)cycloalkyl; mono, di or tri substituted phenyl wherein the substituent is selected from the group consisting of hydrogen, halogen, ($C_1$-$C_6$)alkoxy, ($C_1$-$C_6$)alkylthio, CN, $CF_3$, ($C_1$-$C_6$)alkyl, $N_3$, —$CO_2H$, —$CO_2$—($C_1$-$C_4$)alkyl, —$C(R^5)(R^6)$—OH, —$C(R^5)(R^6)$—O—($C_1$-$C_4$)alkyl and —($C_1$-$C_6$)alkyl—$CO_2$—$R^5$; mono, di or tri substituted heteroaryl wherein the heteroaryl is a monocyclic aromatic ring of 5 atoms, said ring having one hetero atom which is S, O or N and optionally 1, 2, 3 or 4 additional N atoms, said substituents are selected from the group consisting of hydrogen, halogen including fluoro, chloro, bromo and iodo, ($C_1$-$C_6$)alkyl, ($C_1$-$C_6$)alkoxy, ($C_1$-$C_6$)alkylthio, CN, $CF_3$, $N_3$, —$C(R^5)(R^6)$—OH and, —$C(R^5)(R^6)$—O—($C_1$-$C_4$)alkyl; $R^3$ is selected from the group consisting of hydrogen, $CF_3$, CN, ($C_1$-$C_6$)alkyl, hydroxy($C_1$-$C_6$)alkyl, —C(O)—($C_1$-$C_6$)alkyl and optionally substituted —($C_1$-$C_5$)alkyl—Q, —($C_1$-$C_3$)alkyl—O—($C_1$-$C_3$)alkyl—Q, —($C_1$-$C_3$)alkyl—S—($C_1$-$C_3$)alkyl—Q, —($C_1$-$C_5$)alkyl—O—Q, or —($C_1$-$C_5$)alkyl—S—Q, wherein the substituents resides on the alkyl and the substituent is ($C_1$-$C_3$)alkyl; or $R^3$ represents —Q; $R^4$ and $R^{4'}$ are each and independently selected from the group consisting of hydrogen, $CF_3$, CN, ($C_1$-$C_6$)alkyl, —Q, —O—Q, —S—Q, and optionally substituted ($C_1$-$C_5$)alkyl—Q, —O—($C_1$-$C_5$)alkyl—Q, —S—($C_1$-$C_5$)alkyl—Q, —($C_1$-$C_3$)alkyl—O—($C_1$-$C_3$)alkyl—Q, —($C_1$-$C_3$)alkyl—S—($C_1$-$C_3$)alkyl—Q, —($C_1$-$C_5$)alkyl—O—Q, or —($C_1$-$C_5$)alkyl—S—Q, wherein the substituents resides on the alkyl and the substituent is ($C_1$-$C_3$)alkyl; and $R^5$, $R^{5'}$, $R^6$, $R^7$ and $R^8$ are each independently selected from the group consisting of hydrogen, ($C_1$-$C_6$)alkyl or $R^5$, $R^{5'}$, $R^6$, $R^7$ and $R^8$ together with the carbon to which they are attached form a monocyclic saturated carbon ring of 3, 4, 5, 6, or 7 atoms. Q is $CO_2H$, $CO_2$—($C_1$-$C_4$)alkyl, tetrazolyl-5-yl, $C(R^7)(R^8)(OH)$, or $C(R^7)(R^8)(O$—($C_1$-$C_4$)alkyl; provided that when X—Y—Z is S—$CR^4$=$CR^{4'}$, then $R^4$ and $R^{4'}$ are other than $CF_3$.

An example of these compounds is shown in formula (IIf)

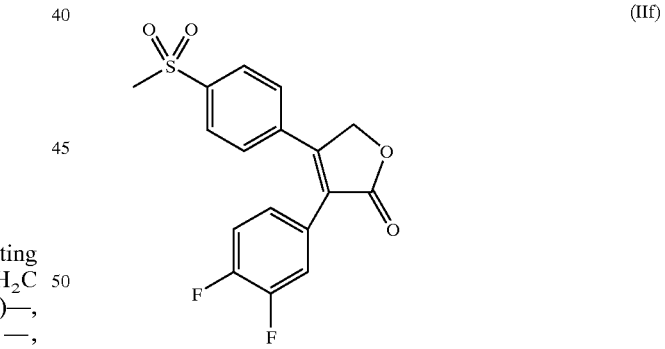

(IIf)

(iv) International patent application No. WO 96/38442 discloses compounds of formula (IIg)

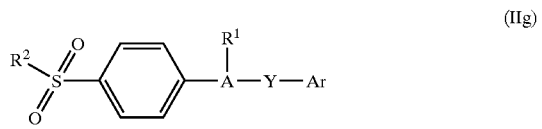

(IIg)

wherein A is a 5 or 6 membered ring substituent selected from partially unsaturated of unsaturated heterocycle and carbocyclic rings, A may be optionally substituted with a radical selected from acyl, halogen, alkyl, haloalkyl, cyano, nitro, carboxyl, alkoxy, oxo, aminocarbonyl, alkoxycarbonyl, carboxyalkyl, cyanoalkyl and hydroxyalkyl; Y is a radical selected from oxy, thio, sulfinyl, sulfonyl, alkyl, alkenyl, alkynyl, alkyloxy, alkylthio, alkylcarbonyl, cycloalkyl, aryl, haloalkyl, hydroxyalkyl, hydroxyalkyloxy, hydroxyalkyloxyalkyl, hydroxyalkylthio, hydroxyalkylthioalkyl, oximinoalkoxy, oximinoalkoxyalkyl, (alkyl)oximinoalkoxy, (alkyl)oximinoalkoxyalkyl, oximinoalkylthio, oximinoalkylthioalkyl, (alkyl)oximinoalkylthio, (alkyl)oximinoalkylthioalkyl, carbonylalkyloxy, carbonylalkyloxyalkyl, carbonylakylthio, carbonylalkylthioalkyl, heterlcyclo, cycloalkenyl, aralkyl, heterocycloalkyl, acyl, alkylthioalkyl, alkyloxyalkyl, alkenylthio, alkynylthio, alkenyloxy, alkynyloxy, alkenylthioalkyl, alkenyloxyalkyl, alkynyloxyalkyl, arylcarbonyl, aralkylcarbonyl, aralkenyl, alkylarylalkynyloxy, alkylarylalkenyloxy, alkylarylalkynylthio, alkylarylalkenylthio, haloalkylcarbonyl, alkoxyalkyl, alkylaminocarbonylalkyl, heteroaralkoxyalkyl, heteroaryloxyalkyl, heteroarylthioalkyl, heteroaralkylthioalkyl, heteroaralkoxy, heteroaralkylthio, heteroaryloxy, heteroarylthio, arylthioalkyl, aryloxyalkyl, haloaryloxyalkyl, aralkylthioalkyl, aralkoxyalkyl, alkoxyaralkoxyalkyl, alkoxycarbonylalkyl, alkoxycarbonylcyanoalkenyl, aminocarbonylalkyl, N-alkylaminocarbonyl, N-arylaminocarbonyl, N,N-dialkylaminocarbonyl, N-alkyl-N-arylaminocarbonyl, cycloalkylaminocarbonyl, heterocycloaminocarbonyl, carboxyalkylaminocarbonyl, alkylcarbonylalkyl, aralkoxycarbonylalkylaminocarbonyl, haloaralkyl, carboxyhaloalkyl, alkoxycarbonylhaloalkyl, aminocarbonylhaloalkyl, alkylaminocarbonylhaloalkyl, N-alkylamino, N,N-dialkylamino, N-arylamino, N-aralkylamino, N-alkyl-N-aralkylamino, N-alkyl-N-arylamino, aminoalkyl, N-alkylaminoalkyl, N,N-dialkylaminoalkyl, N-arylaminoalkyl, N-aralkylaminoalkyl, N-alkyl-N-aralkylaminoalkyl; N-alkyl-N-arylaminoalkyl, aminoalkoxy, aminoalkoxyalkyl, aminoalkylthio, aminoalkylthioalkyl, cycloalkyloxy, cycloalkylalkyloxy, cycloalkylthio, cycloalkylalkylthio, aryloxy, aralkoxy, arylthio, aralkylthio, arlkylsulfinyl, alkylsulfonyl aminosulfonyl, N-alkylaminosulfonyl, N-arylaminosulfonyl, arylsulfonyl, N,N-dialkylaminosulfonyl, N-alky-N-araylaminosulfonyl, or Y represents following groups

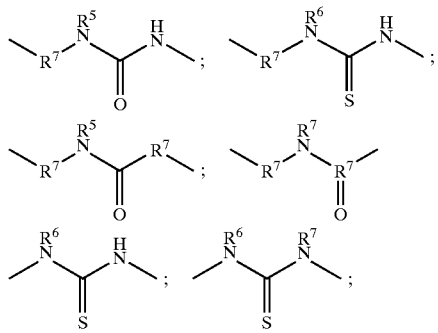

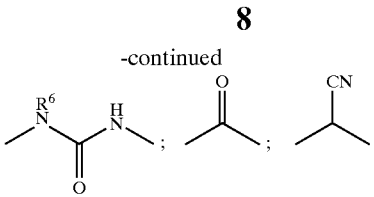

Ar is selected from aryl and heteroaryl, Ar may be optionally substituted with one or two substituents selected from halogen, hydroxyl, mercapto, amino, nitro, cyano, carbamoyl, alkyl, alkenyloxy, alkoxy, alkylthio, alkylsulfonyl, alkylsulfonyl, alkylamino, dialkylamino, haloalkyl, alkoxycarbonyl, N-alkylcarbamoyl, N,N-dialkylcarbamoyl, alkanoylamino, cyanoalkoxy, carbamoylalkoxy, alkoxycarbonylalkoxy, and

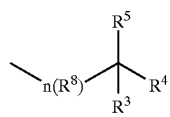

where $R^1$ is one or more substituents selected from heterocycle, cycloalkyl, cycloalkenyl, and aryl, $R^1$ may be optionally substituted at a substitutable position with one or more radicals selected from alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halogen, alkoxy and alkythio; $R^2$ is selected from alkyl and amino; wherein $R^3$ and $R^4$ together form a group of the formula —B—X—$B^1$ which together with the carbon atom to which B and $B^1$ are attached defines a ring having 6 ring atoms, wherein B and $B^1$ which may be the same or different, each is alkylene and X is oxy, and which ring may bear one, two or three substituents, which may be the same or different selected from hydroxyl, alkyl, alkoxy, alkenyloxy and alkynyloxy; wherein $R^5$ is selected from hydroxyl, alkoxy, alkylcarbonyloxy, arylcarbonyloxy, alkoxycarbonyl, acyl, and cyano; wherein $R^6$ is selected from hydrido, alkyl, aryl, and aralkyl; wherein $R^7$ is selected from alkyl, alkoxy, alkenyl, and alkynyl; wherein $R^8$ is oximino optionally substituted with alkyl; wherein n is 0 or 1; provided Ar is substituted with

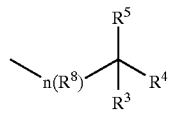

where $R^3$, $R^4$ $R^5$, $R^8$ and n are as defined above

An example of these compounds is shown in formula (IIh)

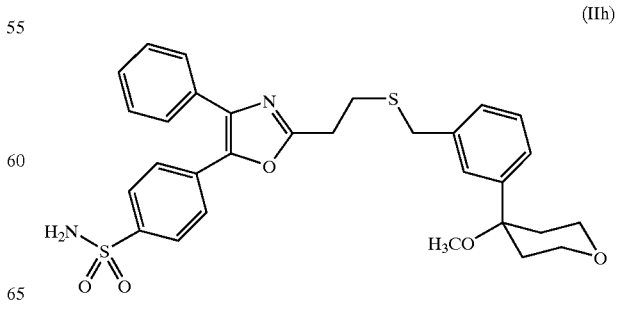

(IIh)

(v) International application WO 96/24585 discloses compounds of formula (IIi)

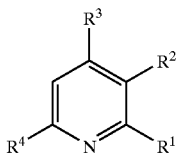

(IIi)

wherein $R^1$ is haloalkyl; $R^2$ is aryl optionally substituted at a substitutable position with one or more radicals independently selected from alkysulfinyl, alkyl, cyano, carboxyl, alkoxycarbonyl, haloalkyl, hydroxyl, hydroxyalkyl, haloalkyl, amino, alkylamino, arylamino, nitro, halogen, alkoxy and alkylthio; $R^3$ is aryl substituted at a substitutable position with a radical selected from alkylsulfonyl and sulfamyl and $R^4$ is selected from halogen, alkoxy, and alkynyloxy.

An example of these compounds is shown in formula (IIj)

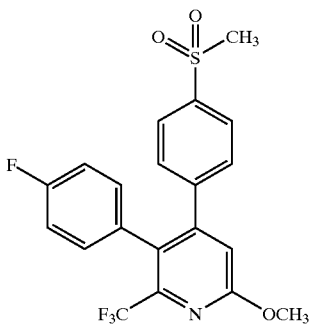

(IIj)

(vi) German patent DE19533643 discloses compounds of formula (IIk)

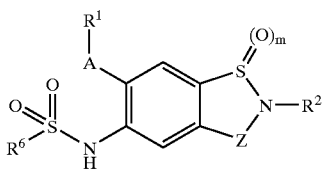

(IIk)

wherein A is O, S or NH; $R^1$ is optionally substituted cycloalkyl, aryl or heteroaryl; $R^2$ is hydrogen, optionally substituted alkyl, aralkyl, aryl, heteroaryl, or $(CH_2)_n$—X; Z is $CH_2$, $CH_2CH_2$, $CH_2CH_2CH_2$, $CH_2CH$=$CH$, $CH_2CO$, NHCO, NHCH$_2$, N=CH, NHCH, $CH_2CH_2NH$, CH=CH, C=O, $S(O)_m$ or optionally substituted NH; m is 0–2; n is 0–8; X is halogen, $NO_2$, optionally substituted OH, COH, COOH, OCOOH, CONHOH, $CONH_2$, SH, $S(O)H$, $SO_2H$, $NH_2$, NHCOH or $NHSO_2H$ or CN; $R^6$ is optionally substituted $(C_1-C_4)$alkyl.

An example of these compounds is shown in formula (III)

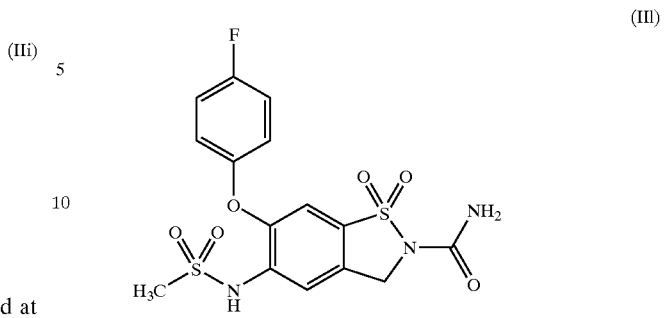

(III)

(vii) International patent application WO 95/15316 discloses compounds of formula (IIm)

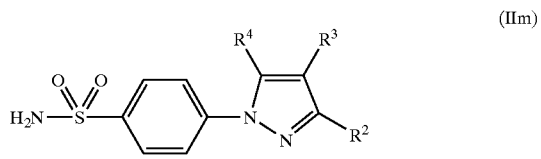

(IIm)

wherein $R^2$ is selected from hydrido, alkyl, haloalkyl, alkoxycarbonyl, cyano, cyanoalkyl, carboxy, aminocarbonyl, alkylaminocarbonyl, cycloalkylaminocarbonyl, arylaminocarbonyl, carboxyalkylaminocarbonyl, carboxyalkyl, aralkoxycarbonylalkylaminocarbonyl, aminocarbonylalkyl, alkoxycarbonyl, cyanoalkenyl and hydroxyalkyl; wherein $R^3$ is selected from hydrido, alkyl, cyano, hydroxyalkyl, cycloalkyl, alkylsulfonyl, and halogen; $R^4$ is selected from aralkenyl, aryl, cycloalkyl, cycloalkenyl and heterlcyclic, $R^4$ is optionally substituted at a substitutable position with one or more radicals selected from halogen, alkylthio, alkylsulfonyl, cyano, nitro, haloalkyl, alkyl, hydroxyl, alkenyl, hydroxyalkyl, carboxyl, cycloalkyl, alkylamino, dialkylamino, alkoxycarbonyl, aminocarbonyl, alkoxy, haloalkoxy, sulfamyl, heterocyclic and amino; provided $R^2$ and $R^3$ are not both hydrido; further provided that $R^2$ is not carboxyl, or methyl when $R^3$ is hydrido and when $R^4$ is phenyl; further provided that $R^4$ is not triazolyl when $R^2$ is methyl; further provided that $R^4$ is not aralkenyl when $R^2$ is carboxyl, aminocarbonyl or ethoxycarbonyl; further provided that $R^4$ is not phenyl when $R^2$ is methyl and $R^3$ is carboxyl; and further provided that $R^4$ is not unsubstituted thienyl when $R^2$ is trifluoromethyl.

An example of these compounds is shown in formula (IIn)

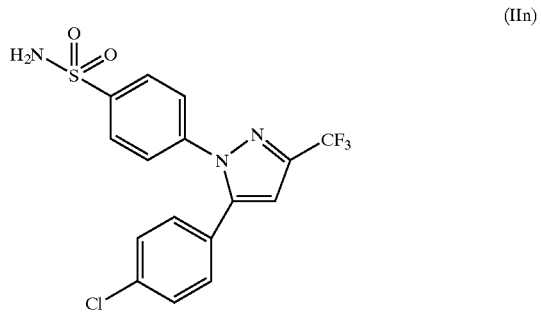

(IIn)

(viii) International patent application WO 96/19462 discloses compounds of formula (IIo)

(IIo)

wherein one of R, $R^1$ is methylsulfonylphenyl, aminosulfonylphenyl or alkylaminosulfonylphenyl and the other is 5–7 carbon cycloalkyl optionally substituted by alkyl, thienyl or furyl optionally substituted by alkl or halogen; $R^2$ is lower alkyl.

An example of these compounds is shown in formula (IIp)

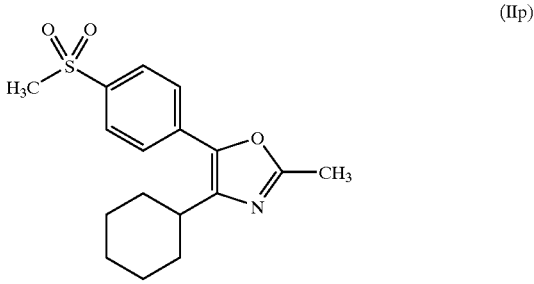

(IIp)

OBJECTIVE OF THE INVENTION

With an objective to develop novel compounds for the treatment and/or prophylaxis of diseases or conditions related to cyclooxygenase, more particularly COX-2 and other related diseases such as pain, fever or inflammation, to inhibit prostanoid-induced smooth muscle contraction, to treat Alzheimer disease, colorectal cancer, for the treatment of pain, fever, and inflammation related to common cold, influenza, viral infections, for the treatment of arthritis such as rheumatoid arthritis, osteoarthritis, gouty arthritis, juvenile arthritis, spondylo arthritis; systemic lupus erythematosus, skin inflammation disorders such as eczema, burns, dermatitis, psoriasis; low back and neck pain, dysmenorrhoea, head ache, tooth ache, sprains, strains, myostis, neuralgia, synovitis, bursitis, tendinitis, wounds resulting from surgical and dental procedures, post-operative inflammation including ophthalmic surgery such as cataract and refractive surgery, with better efficacy, potency and lower toxicity, we focussed our research to develop new compounds effective in the treatment of above mentioned diseases or conditions. Effort in this direction has led to the development of compounds having general formula (I).

The main objective of the present invention is therefore, to provide novel compounds and their derivatives, their analogs, their tautomeric forms, their stereoisomers, their regioisomers, their polymorphs, their pharmaceutically acceptable salts, their pharmaceutically acceptable solvates and pharmaceutical compositions containing them, or their mixtures.

Another objective of the present invention is to provide novel compounds and their derivatives, their analogs, their tautomeric forms, their stereoisomers, their regioisomers, their polymorphs, their pharmaceutically acceptable salts, their pharmaceutically acceptable solvates and pharmaceutical compositions containing them or their mixtures having enhanced activities, without toxic effect or with reduced toxic effect.

Yet another objective of the present invention is to produce a process for the preparation of novel compounds and their derivatives of the formula (I) as defined above, their analogs, their tautomeric forms, their stereoisomers, their regioisomers, their polymorphs, their pharmaceutically acceptable salts and their pharmaceutically acceptable solvates.

Still another objective of the present invention is to provide pharmaceutical compositions containing compounds of the general formula (I), their analogs, their derivatives, their tautomers, their stereoisomers, their regioisomers, their polymorphs, their salts, solvates or their mixtures in combination with pharmaceutically acceptable carriers, solvents, diluents and other media normally employed in preparing such compositions, optionally containing one or more ingredients such as another analgesic agent like acetaminophen, phenacetin, a potentiator like caffeine, a $H_2$ antagonist, aluminum or magnesium hydroxide, simethicone, a decongestant such as phenylephrine, phenyl propanolamine, pseudophedrine, oxymetazoline, epinephrine, nephazoline, propylhexadrine or leavo-desoxyephedrine, xylomatazoline, a sedating or non sedating antihistamine, an antitussive such as dextromethorphan, carbetapentane, caramiphen, hydrocodeine and codeine and the like, or a diuretic agent.

The present invention also provides a method for the treatment of cyclooxygenase mediated diseases comprising administering a patient in need thereof, a nontoxic therapeutically effective amount of compound of formula (I) or pharmaceutical composition described above.

The present invention also provides novel intermediates of formulae (I-1), (I-3), (I-5), (I-7), (II-1), (II-2) and (II-4).

SUMMARY OF THE INVENTION

The present invention relates a novel compound having the general formula (I)

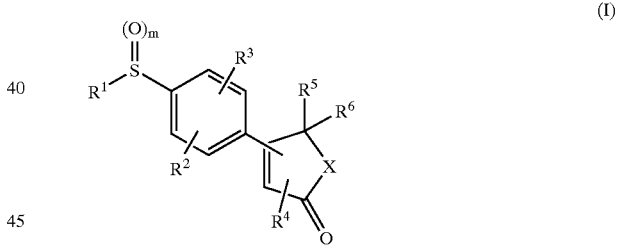

(I)

wherein $R^1$ represents amino or substituted or unsubstituted groups selected from alkyl, alkylamino, acylamino, cycloalkyl, cyclicamino, carboethoxycarbonylalkyl, hydrazino, hydrazido, aminoacid residue, aryl, heteroaryl or —N=CR(NR)$_2$ where R represents hydrogen or lower alkyl group; $R^2$ represents halogen, hydroxy, cyano, nitro, azido, formyl, oximealkyl, thio or substituted or unsubstituted groups selected from amino, alkyl, alkoxy, hydrazino, hydrazinoalkyl, hydrazido, hydrazidoalkyl, aminoacid residue, aminoacid residuealkyl, acyl, carbonyloxyalkyl, haloalkyl, aminoalkyl, haloalkoxy, hydroxyalkyl, alkoxyalkyl, thioalkyl, alkylthio, alkylsulfinyl, alkylsulfonyl, aryl, aralkyl, aryloxy, aralkoxy, aryloxyalkyl, aralkoxyalkyl, carboxamidoalkyl, carbonylaminoalkyl groups or when the groups —S(=O)$_m$—$R^1$ and $R^2$ are present on adjacent carbon atoms, $R^1$ and $R^2$ together with atoms to which they are attached may also form a substituted or unsubstituted 5–7 membered cyclic structure containing carbon atoms, a sulfur atom and may optionally contain one or two heteroatoms selected from O, S or N; $R^3$ represents hydrogen, halogen atom, hydroxy, nitro, cyano, azido or substituted or unsubstituted groups selected from hydrazino, hydrazinoalkyl, hydrazido, hydrazidoalkyl, aminoacid residues, alkyl, alkoxy, hydroxyalkyl, alkoxyalkyl, acylamino or amino groups; $R^4$ and $R^5$ may be same or different and independently represent hydrogen, halogen, hydroxy, cyano, nitro, thio, hydroxyamino, substituted or unsubstituted groups selected from alkyl, alkoxy, acyl, acyloxy, amino, hydrazino, hydrazinoalkyl, hydrazido, hydrazidoalkyl, aminoacid residues, aminoacyl, carboxyalkyl, carboxyalkenyl, aryl, aryloxy, aralkyl, aralkoxy, alkoxycarbonyl, aryloxycarbonyl, aralkoxycarbonyl, heteroaryl, heteroaryloxy, heteroaralkyl, heteroaralkoxy, heteroarylcarbonyl, heteroaryloxycarbonyl, heteroaralkylcarbonyl, heteroaralkoxycarbonyl, heterocyclylcarbonyl, aminocarbonyl, aminocarbonylalkyl, carbonylamino, cycloalkylacylamino, alkylaminoalkoxy, alkylaminoacyl, carboxylic acid or its derivatives, saturated or partially saturated or aromatic single or fused 5 to 7 membered carbocycle ring or saturated or partially saturated or aromatic, single or fused 5 to 7 membered heterocycle ring; $R^6$ represents hydrogen, halogen, hydroxy, amino, cyano, nitro, thio, hydroxyamino or unsubstituted or substituted groups selected from alkyl, alkoxy, carboxyalkyl; the furanone ring maybe fused with $R^4$ wherever possible; $R^5$ and $R^6$ together may represent $=C(R^a)(R^b)$, where $R^a$ and $R^b$ may be same or different and independently represent hydrogen, $(C_1-C_6)$alkyl or aryl; $=O$ or $=NR^7$ where $R^7$ represents hydrogen, aryl or heteroaryl group; X represents oxygen or $NR^8$, where $R^8$ represents hydrogen or substituted or unsubstituted groups selected from $(C_1-C_6)$alkyl, aryl, aralkyl, heteroaryl, heteroaralkyl, aralkenoyl, aralkanoyl and m is an integer in the range of 0–2.

DETAILED DESCRIPTION OF THE INVENTION

Suitable groups represented by $R^1$ may be selected from amino, substituted or unsubstituted linear or branched $(C_1-C_6)$alkyl group such as methyl, ethyl, n-propyl, isopropyl, n-butyl, iso-butyl, t-butyl, n-pentyl, isopentyl, hexyl and the like; $(C_1-C_6)$ alkylamino group such as methylamino, ethylamino, propylamino, butylamino, pentylamino, hexylamino and the like, which may be substituted; acylamino groups such as $NHCOCH_3$, $NHCOC_2H_5$, $NHCOC_3H_7$, $NHCOC_6H_5$ and the like, which may be substituted; $(C_3-C_8)$cycloalkyl group such as cyclopropyl, cyclobutyl, cyclopentyl, cyclohexyl, cycloheptyl and the like, which may be substituted; cyclicamino group such as aziridine, pyrrolidine, piperidine and the like, the cyclicamino group may be substituted; carboethoxycarbonyl$(C_1-C_6)$alkyl group such as carboethoxycarbonylmethyl, carboethoxycarbonylethyl, carboethoxycarbonylpropyl and the like, the carboethoxycarbonyl$(C_1-C_6)$alkyl group may be substituted; hydrazino, which may be substituted; hydrazido, which may be substituted; aminoacid residues, wherein the aminoacid is selected from glycine, alanine, phenylalanine, lysine and the like, which may be substituted; aryl group such as phenyl, naphthyl and the like, the aryl group may be substituted; heteroaryl group such as pyrrole, furan, pyridine, thiophene and the like, the heteroaryl group may be substituted; or $-N=CR(NR)_2$.

The suitable groups represented by R are selected from hydrogen or $(C_1-C_6)$alkyl group such as methyl, ethyl, n-propyl, isopropyl, n-butyl, iso-butyl and the like.

Suitable groups represented by $R^2$ may be selected halogen atom such as chlorine, fluorine, bromine or iodine; hydroxy, cyano, nitro, azido, formyl, oxime$(C_1-C_6)$alkyl groups such as oximemethyl, oximeethyl, oximepropyl and the like; thio, amino group, which may be substituted; substituted or unsubstituted linear or branched $(C_1-C_6)$alkyl group such as methyl, ethyl, n-propyl, isopropyl, n-butyl, iso-butyl, t-butyl, n-pentyl, isopentyl, hexyl and the like; $(C_1-C_6)$alkoxy such as methoxy, ethoxy, propyloxy, butyloxy, iso-propyloxy and the like, which may be substituted; hydrazino, which may be substituted; hydrazino $(C_1-C_6)$alkyl group such as hydrazinomethyl, hydrazinoethyl, hydrazinopropyl and the like, which may be substituted; hydrazido, which may be substituted; hydrazido $(C_1-C_6)$alkyl such as hydrazidomethyl, hydrazidoethyl, hydrazidopropyl and the like, which may be substituted; aminoacid residues, wherein the aminoacid is selected from glycine, alanine, phenylalanine, lysine and the like, which may be substituted; aminoacid residue$(C_1-C_6)$alkyl wherein the aminoacid is as defined above, which may be substituted; acyl group such as acetyl, propanoyl, benzoyl and the like, which may be substituted; carbonyloxy$(C_1-C_6)$alkyl group such as carbonyloxymethyl, carbonyloxyethyl, carbonyloxypropyl and the like, which may be substituted; halo$(C_1-C_6)$ alkyl such as chloromethyl, bromoethyl, chloropropyl, chloroisopropyl and the like, which may be substituted; amino$(C_1-C_6)$alkyl such as aminomethyl, aminoethyl, aminopropyl, aminoisopropyl and the like, which may be substituted; halo$(C_1-C_6)$alkoxy such as chloromethoxy, bromethoxy, chloropropoxy, bromopropoxy and the like, which may be substituted; hydroxy$(C_1-C_6)$alkyl such as hydroxymethyl, hydroxyethyl, hydroxypropyl, hydroxyisopropyl and the like, which may be substituted; alkoxy $(C_1-C_6)$alkyl group such as methoxymethyl, ethoxymethyl, methoxyethyl, ethoxyethyl and the like, which may be substituted; thio$(C_1-C_6)$alkyl such as thiomethyl, thioethyl, thiopropyl, thioisopropyl and the like, which may be substituted; $(C_1-C_6)$alkylthio such as methylthio, ethylthio, propylthio, isopropylthio and the like, which may be substituted; $(C_1-C_6)$alkylsulfinyl such as methylsulfinyl, ethylsulfinyl, n-propylsulfinyl, isopropysulfinyl, butylsulfinyl and the like, the $(C_1-C_6)$alkylsulfinyl group may be substituted; $(C_1-C_6)$alkylsulfonyl such as methylsulfonyl, ethylsulfonyl, n-propylsulfonyl, isopropysulfonyl, butylsulfonyl and the like, the $(C_1-C_6)$alkylsulfonyl group may be substituted; aryl group such as phenyl, naphthyl and the like, the aryl group may be substituted; aralkyl such as benzyl, phenethyl, $C_6H_5CH_2CH_2CH_2$, naphthylmethyl and the like, the aralkyl group may be substituted; aryloxy group such as phenoxy, naphthyloxy and the like, the aryloxy group may be substituted; aralkoxy group such as benzyloxy, phenethyloxy, naphthylmethyloxy, phenylpropyloxy and the like, which may be substituted; aryloxyalkyl group such as $C_6H_5OCH_2$, $C_6H_5OCH_2CH_2$, naphthyloxymethyl and the like, which may be substituted; aralkoxyalkyl group such as $C_6H_5CH_2OCH_2$, $C_6H_5CH_2OCH_2CH_2$ and the like, which may be substituted; carboxamido$(C_1-C_6)$alkyl such as carboxamidomethyl, carboxamidoethyl, carboxamidopropyl and the like, carboxamido$(C_1-C_6)$alkyl group may be substituted; carbonylamino$(C_1-C_6)$alkyl group such as carbonylaminomethyl carbonylaminoethyl, carbonylaminopropyl and the like, the carbonylamino$(C_1-C_6)$alkyl may be substituted.

When $R^1$ and $R^2$ together form a cyclic structure, $R^1$ and $R^2$ together represent substituted or unsubstituted $-NH-C(=O)-(CH_2)_n-$, $-CH_2-(CH_2)_n-$, $-(CH_2)_n-C(=O)-$, $-CH_2-C(=O)-CH_2-$, $-NH-(CH_2)_n-$, $-NH-C(=O)-$, $-NH-(CH_2)_n-C(=O)-$, $-(CH_2)_n-C(=O)-NH-$, $-NH-(CH_2)_n-O-$, —NH—(CH$_2$)$_n$—S—, —CH$_2$—(CH$_2$)$_n$—O—, —CH$_2$—(CH$_2$)$_n$—S—, where n is an integer in the range of 1–2.

The substituents on R$^1$ and R$^2$ may be selected from hydroxy, linear or branched (C$_1$–C$_6$)alkyl, (C$_1$–C$_6$)alkoxy, aryl, aralkyl, aralkoxy, acyl, heteroaryl such as pyridyl, furyl, thiophenyl, oxazolyl and the like; heteroaralkyl such as pyridylmethyl, pyridylethyl, furanmethyl, furanethyl and the like; heterocyclyl such as morpholinyl, piperidinyl, piperzinyl, pyrrolidinyl, dihydro-3-oxo-1,1-dioxo-benzo[b]isothiazyl, benzoisothiazolyl, benzothiazolyl and the like; sulfonyl, (C$_1$–C$_6$)alkylsulfinyl, arylsulfinyl such as phenylsulfonyl, naphthylsulfonyl and the like; (C$_1$–C$_6$)alkylsulfonyl, arylsulfonyl such as phenylsulfinyl, naphthylsulfinyl and the like; wherein the alkyl and aryl moieties may be substituted with hydroxy, halogen atom such as chlorine, fluorine, bromine or iodine; nitro or amino groups.

Suitable groups represented by R$^3$ may be selected from hydrogen, halogen atom such as chlorine, fluorine, bromine or iodine; hydroxy, nitro, cyano, azido, hydrazino, which may be substituted; hydrazino(C$_1$–C$_6$)alkyl groups such as hydrazinomethyl, hydrazinoethyl, hydrazinopropyl and the like, which may be substituted; hydrazido, which may be substituted; hydrazido(C$_1$–C$_6$)alkyl such as hydrazidomethyl, hydrazidoethyl, hydrazidopropyl and the like, which may be substituted; aminoacid residues, wherein the aminoacid is selected from glycine, alanine, phenylalanine, lysine and the like, which may be substituted; linear or branched (C$_1$–C$_6$)alkyl group such as methyl, ethyl, n-propyl, isopropyl, n-butyl, iso-butyl, t-butyl, n-pentyl, isopentyl, hexyl and the like, which may be substituted; (C$_1$–C$_6$)alkoxy such as methoxy, ethoxy, propyloxy, butyloxy, iso-propyloxy and the like, which may be substituted; hydroxy(C$_1$–C$_6$)alkyl such as hydroxymethyl, hydroxyethyl, hydroxypropyl, hydroxyisopropyl and the like, which may be substituted; (C$_1$–C$_6$)alkoxy(C$_1$–C$_6$)alkyl group such as methoxymethyl, ethoxymethyl, methoxyethyl, ethoxypropyl and the like, which may be substituted; acylamino groups such as NHCOCH$_3$, NHCOC$_2$H$_5$, NHCOC$_3$H$_7$, NHCOC$_6$H$_5$ and the like, which may be substituted; amino group, which may be substituted.

Suitable groups represented by R$^4$ and R$^5$ may be selected from hydrogen, halogen atom such as fluorine, chlorine, bromine, or iodine; hydroxy, cyano, nitro, thio, hydroxylamino, substituted or unsubstituted linear or branched (C$_1$–C$_6$)alkyl group such as methyl, ethyl, n-propyl, isopropyl, n-butyl, iso-butyl, t-butyl, n-pentyl, isopentyl, hexyl and the like; (C$_1$–C$_6$)alkoxy such as methoxy, ethoxy, propoxy, isopropoxy, butoxy and the like, the (C$_1$–C$_6$)alkoxy groups may be substituted; acyl group such as formyl, acetyl, propanoyl, benzoyl and the like; the acyl group may be substituted; acyloxy group such as OCOMe, OCOEt, OCOPh and the like, the acyloxy group may be substituted; amino group, which may be substituted; hydrazino, which may be substituted; hydrazino(C$_1$–C$_6$)alkyl groups such as hydrazinomethyl, hydrazinoethyl, hydrazinopropyl and the like, which may be substituted; hydrazido, which may be substituted; hydrazido(C$_1$–C$_6$)alkyl such as hydrazidomethyl, hydrazidoethyl, hydrazidopropyl and the like, which may be substituted; aminoacid residues, wherein the aminoacid is selected from glycine, alanine, phenylalanine, lysine and the like, which may be substituted; aminoacyl such as aminoacetyl, aminopropanoyl, aminobutanoyl and the like, which may be substituted; carboxy(C$_1$–C$_6$)alkyl such as carboxymethoxy, carboxyethyl, carboxypropyl and the like, which may be substituted; carboxy(C$_2$–C$_6$)alkenyl such as carboxyethenyl, carboxypropenyl, carboxybutenyl and the like, which may be substituted; aryl group such as phenyl, naphthyl and the like, the aryl group may be substituted; aryloxy group such as phenoxy, naphthyloxy and the like, the aryloxy group may be substituted; aralkyl such as benzyl, phenethyl, C$_6$H$_5$CH$_2$CH$_2$CH$_2$, naphthylmethyl and the like, the aralkyl group may be substituted; aralkoxy group such as benzyloxy, phenethyloxy, naphthylmethyloxy, phenylpropyloxy and the like, which may be substituted; (C$_1$–C$_6$)alkoxycarbonyl such as methoxycarbonyl, ethoxycarbonyl, propoxycarbonyl and the like, the (C$_1$–C$_6$) alkoxycarbonyl may be substituted; aryloxycarbonyl such as phenoxycarbonyl, naphthyloxycarbonyl and the like, which may be substituted; aralkoxycarbonyl group such as benzyloxycarbonyl, phenethyloxycarbonyl, naphthylmethoxycarbonyl and the like, which may be substituted; aminocarbonyl, which may be substituted; carbonylamino, which may be substituted; aminocarbonyl(C$_1$–C$_6$)alkyl such as aminocarbonylmethyl, aminocarbonylethyl, aminocarbonylpropyl and the like, the aminocarbonyl(C$_1$–C$_6$)alkyl may be substituted; (C$_1$–C$_6$)alkylamino(C$_1$–C$_6$)alkoxy groups such as methylaminomethoxy, ethylaminoethoxy, methylaminoethoxy, ethylaminomethoxy, propylaminoethoxy and the like, the (C$_1$–C$_6$)alkylamino(C$_1$–C$_6$)alkoxy group may be substituted; (C$_1$–C$_6$)alkylaminoacyl groups such as methylaminoacetyl, ethylaminopropanoyl, methylaminopropanoyl, ethylaminoacetyl and the like, the (C$_1$–C$_6$)alkylaminoacyl group may be substituted; (C$_3$–C$_8$)cycloalkylacylamino such as cyclopropylacylamino, cyclobutylacylamino, cyclobutylacylamino and the like, (C$_3$–C$_8$)cycloalkylaminoacyl may be substituted; substituted or unsubstituted carbocyclic groups such as phenyl, indenyl, indanyl, dihydronaphthyl, tetrahydronaphthyl, naphthyl, cyclobutyl, cyclopentyl, cyclohexyl, cycloheptyl, cyclobutenyl, cyclopentenyl, cyclohexenyl and the like; heteroaryl and heterocyclyl groups such as pyrrolyl, pyrrolidinyl, furyl, dihydrofuryl, tetrahydrofuryl, furanonyl, benzofuryl, dihydrobenzofuryl, benzofuranonyl, thienyl, benzotheinyl, dihydrobenzotheinyl, thiazolyl, benzothiazolyl, imidazolyl, benzimidazolyl, pyrazolyl, oxazolyl, isooxazolyl, benzoxazolyl, isothiazolyl, oxadiazolyl, thiadiazolyl, triazolyl, tetrazolyl, indolyl, azaindolyl, indolinyl, dihydroindolinyl, dihydroindolinonyl, azaindolinyl, pyranyl, benzopyranyl, dihydrobenzopyranyl, tetrahydrobenzopyranyl, diazinyl, triazinyl, tetrazinyl, pyridyl, piperidinyl, piperidinonyl, pyridazinyl, pyrazinyl, piperazinyl, morpholinyl, quinolinyl, dihydroquinolinyl, oxazinyl, benzoxazinyl, dihydrobenzoxazinyl, thiazinyl, benzothiazinyl, dihydrobenzothiazinyl, quinazolinyl, dihydroquinazolinyl, phthalazinyl, dihydrophthalazinyl, quinaoxalinyl, dihydrobenzothienyl-1-oxide, dihydrobenzothienyl-1,1-dioxide, which may be substituted; heterocyclylcarbonyl groups such as pyrrolidinylcarbonyl, morpholinylcarbonyl, piperidinylcarbonyl, piperazinylcarbonyl and the like, the heterocyclyl group may be substituted; heteroaryl carbonyl group such as pyridylcarbonyl, thienylcarbonyl, furylcarbonyl, pyrrolylcarbonyl, oxazolylcarbonyl, thiazolylcarbonyl, oxadiazolylcarbonyl, thiadiazolylcarbonyl, tetrazolylcarbonyl and the like, the heteroaryl group may be substituted; heteroaralkyl such as pyridylmethyl, pyridylethyl, furanmethyl, furanethyl and the like, which may be substituted; heteroaryloxy, heteroaralkoxy, heteroaralkylcarbonyl, heteroaryloxycarbonyl, heteroaralkoxycarbonyl, wherein the heteroaryl and heteroaralkyl moieties are as defined above, which may be substituted; carboxylic acid or its derivatives such as amides, like CONH$_2$, CONHMe, CONMe$_2$, CONHEt, CONEt$_2$, CONHPh and the like;

Suitable substituents on the groups represented by $R^4$ and $R^5$ are selected from halogen atom such as fluorine, chlorine, bromine, or iodine; hydroxy, cyano, nitro, optionally halogenated $(C_1-C_6)$alkyl, optionally halogenated $(C_1-C_3)$ alkoxy, acyl, amino, acylamino, $(C_3-C_8)$cycloalkyl, $(C_3-C_8)$ cycloalkoxy, aryl, aryloxy, aralkyl, aralkoxy, heteroaryl, heterocyclyl such as morpholinyl, piperidinyl, piperzinyl, pyrrolidinyl and the like; heteroaryloxy, heteroaralkyl, heteroaralkoxy, heteroaryloxycarbonyl, heteroaralkoxycarbonyl, heteroaryloxycarbonylamino, heteroaralkoxycarbonylamino, acyloxy, $(C_1-C_6)$ alkoxycarbonyl, aryloxycarbonyl, aralkoxycarbonyl, mono $(C_1-C_6)$ alkylamino such as methylamino, ethylamino, isopropylamino and like, $(C_1-C_6)$ dialkylamino such as dimethylamino, methylethylamino and the like; arylamino such as phenylamino, naphthylamino and the like; aralkylamino such as benzylamino, phenethylamino and the like; amino$(C_1-C_6)$alkyl such as aminomethyl, aminoethyl, aminoisopropyl and the like; hydroxy$(C_1-C_6)$alkyl, $(C_1-C_6)$ alkoxy$(C_1-C_6)$alkyl such as methoxymethyl, methoxyethyl, ethoxypropyl and the like; aryloxy$(C_1-C_6)$alkyl such as phenyloxymethyl, phenyloxy ethyl, naphthyloxy methyl, naphthyloxyethyl and the like; aralkoxy$(C_1-C_6)$alkyl such as benzyloxymethyl, benzyloxyethyl, phenethoxymethyl, phenethoxyethyl and the like; $(C_1-C_6)$alkoxycarbonylamino such as methoxycarbonylamino, ethoxycarbonylamino, propoxycarbonylamino and the like; aryloxycarbonylamino such as phenyloxycarbonylamino, naphthyloxycarbonylamino, aralkoxycarbonylamino such as benzyloxycarbonylamino, phenethyloxycarbonylamino and the like; thio, thio$(C_1-C_6)$alkyl, $(C_1-C_6)$alkylthio, $(C_1-C_6)$ alkylsulfinyl such as methylsulfinyl, ethylsulfinyl, n-propylsulfinyl, isopropylsulfinyl, butylsulfinyl and the like; $(C_1-C_6)$alkylsulfonyl methylsulfonyl, ethylsulfonyl, n-propylsulfonyl, isopropysulfonyl, butylsulfonyl and the like; sulfonic acid or its derivatives such as $SO_2NH_2$, $SO_2NHMe$, $SO_2NMe_2$, $SO_2NHEt$, $SO_2NEt_2$ and the like; or carboxylic acid or its derivatives such as amides, like $CONH_2$, $CONHMe$, $CONMe_2$, $CONHEt$, $CONEt_2$, $CONHPh$ and the like. The substituents on the groups are as defined for $R^4$ and $R^5$.

Suitable groups represented by $R^6$ are selected from hydrogen, halogen atom such as fluorine, chlorine, bromine, or iodine; hydroxy, amino, cyano, nitro, thio, hydroxylamino, linear or branched $(C_1-C_6)$alkyl group, such as methyl, ethyl, n-propyl, iso-propyl, n-butyl, iso-butyl, t-butyl, n-pentyl, iso-pentyl, hexyl and the like, the $(C_1-C_6)$alkyl group may be substituted; $(C_1-C_6)$alkoxy such as methoxy, ethoxy, propyloxy, butyloxy, iso-propyloxy and the like, the $(C_1-C_6)$alkoxy group may be substituted; carboxy$(C_1-C_6)$alkyl such as carboxymethyl, carboxyethyl, carboxypropyl and the like, the carboxy$(C_1-C_6)$alkyl may be substituted.

The suitable groups represented by $R^a$ and $R^b$ are selected from hydrogen or $(C_1-C_6)$alkyl group such as methyl, ethyl, n-propyl, isopropyl, n-butyl, iso-butyl and the like; aryl group such as phenyl, naphthyl and the like.

The suitable groups represented by $R^7$ are selected from hydrogen, aryl group such as phenyl, naphthyl and the like; heteroaryl group such as pyridyl, furyl, thiophenyl, benzothiazoyl, purinyl, benzimidazoyl, pyrimidinyl, tetrazolyl and the like;

Suitable ring structures formed by $R^4$ fused with furanone may be selected from 2,3a,4,5-tetrahydronaphtho[2,1-b] furan-2-one; 4-thioxo-2,3a,4,5-tetrahydronaphtho[2,1-b] furan-2-one; 4-imino-2,3a,4,5-tetrahydronaphtho[2,1-b] furan-2-one; 3a,4,5,6-tetrahydronaphtho[2,1-b]furan-2-one; 2,3a-dihydronaphtho[2,1-b]furanone; 2,3a,4,5-tetrahydronaphtho[2,1-b]furan-2,4-dione; 2,3a-dihydronaphtho[2,1-b]furan-2,4-dione; 3a,4-dihydro-2H-furo[2,3-c]chromene-2-one; 3a,4-dihydro-2H-furo[2,3-c] chromene-2,4-dione; 2,3a,4,5-tetrahydro-2H-furo[2,3-c] chromene-2-one; 4-thioxo-2,3a,4,5-tetrahydro-2H-furo[2,3-c]chromene-2-one; 4-imino-2,3a,4,5-tetrahydro-2H-furo[2,3-c]chromene-2-one; 2,3a,4,5-tetrahydro-2H-furo[2,3-c] chromene-2,4-dione; 2,3a,4,5-tetrahydrofuro[2,3-c] quinolin-2-one; 2,3a,4,5-tetrahydrofuro[2,3-c]quinolin-2,4-dione;

8,8a-dihydro-2H-indeno[2,1-b]furan-2-one; 4-thioxo-8, 8a-dihydro-2H-indeno[2,1-b]furan-2-one; 4-imino-8,8a-dihydro-2H-indeno[2,1-b]furan-2-one; 2,8a-dihydrobenzo [4,5]thieno[2,3-b]furan-2-one; 2,8a-dihydrobenzo[b]furo[3, 2-d]furan-2-one; 8,8a-dihydro-2H-furo[2,3-b]indol-2-one; 8,8a-dihydro-2H-indeno[2,1-b]furan-2-one; 3a,4,5,6-tetrahydro-2H-benzo[3,4]cyclohepta[b]furan-2-one; 3a,4,5, 8-tetrahydro-2H-indeno[5,4-b]furan-2-one; 4,5,5a,7-tetrahydro-1H-furo[2,3-g]indol-7-one; 4,5,5a,7-tetrahydrothieno[2',3':3,4]benzo[b]furan-7-one; 4,5,5a,7-tetrahydrofuro[2',3':3,4]benzo[b]furan-7-one.

The suitable groups represented by X are selected from oxygen or $NR^8$ where $R^8$ represents hydrogen or linear or branched $(C_1-C_6)$alkyl group such as methyl, ethyl, n-propyl, isopropyl, n-butyl, iso-butyl, t-butyl, n-pentyl, isopentyl, hexyl and the like, the $(C_1-C_6)$alkyl group may be substituted; aryl group such as phenyl, naphthyl and the like, the aryl group may be substituted; aralkyl such as benzyl, phenethyl and the like, the aralkyl group may be substituted; heteroaryl group such as pyridyl, furyl, thiophenyl, benzothiazoyl, purinyl, benzimidazoyl, pyrimidinyl, tetrazolyl and the like, the heteroaryl group may be substituted; heteroaralkyl group such as pyridylmethyl, pyridylethyl, furanmethyl, furanethyl and the like, the heteroaralkyl group may be substituted; aralkenoyl group such as phenylpropenoyl, phenylbutenoyl, phenylpentenoyl and the like, the aralkenoyl group may be substituted; aralkanoyl group such as phenylpropanoyl, phenylbutanoyl, phenylpentanoyl and the like, the aralkanoyl group may be substituted.

The substituents on $R^3$, $R^6$ and $R^8$ may be selected from nitro, halogen atom such as fluorine, chlorine, bromine or iodine; amino, hydroxy, thio or cyano groups.

Pharmaceutically acceptable salts forming part of this invention include salts derived from inorganic bases such as Li, Na, K, Ca, Mg, Fe, Cu, Zn, Mn; salts of organic bases such as N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine, and the like; chiral bases like alkylphenylamine, glycinol, phenyl glycinol and the like, salts of natural amino acids such as glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids such as D-isomers or substituted amino acids; guanidine, substituted guanidine wherein the substituents are selected from nitro, amino, alkyl, alkenyl, alkynyl, ammonium or substituted ammonium salts and aluminum salts. Salts may include acid addition salts where appropriate which are, sulphates, nitrates, phosphates, perchlorates, borates, halides, acetates, tartrates, maleates, citrates, succinates, palmoates, methanesulphonates, benzoates, salicylates, hydroxynaphthoates, benzenesulfonates, ascorbates, glycerophosphates, ketoglutarates and the like. Pharmaceutically acceptable solvates may be hydrates or comprising other solvents of crystallization such as alcohols.

Representative compounds prepared according to the process of the present invention may be selected from:

4-(1,1-Dioxo-2,3-dihydrobenzo[b]thiophen-5-yl)-3-(3,4-difluorophenyl)-2,5-dihydro-2-furanone;

4-(3-Methyl-4-methylsulfanylphenyl)-3-(3,4-difluorophenyl)-2,5-dihydro-2-furanone;

4-(3-Methyl-4-methylsulfonylphenyl)-3-(3,4-difluorophenyl)-2,5-dihydro-2-furanone;

4-(3-Methyl-4-methylsulfanylphenyl)-3-phenyl-2,5-dihydro-2-furanone;

4-(3-Methyl-4-methylsulfonylphenyl)-3-phenyl-2,5-dihydro-2-furanone;

4-(3-Methyl-4-methylsulfanylphenyl)-3-(4-fluorophenyl)-2,5-dihydro-2-furanone;

4-(3-Methyl-4-methylsulfanylphenyl)-3-(4-methylphenyl)-2,5-dihydro-2-furanone;

4-(3-Methyl-4-methylsulfonylphenyl)-3-(4-fluorophenyl)-2,5-dihydro-2-furanone;

4-(3-Methyl-4-methylsulfonylphenyl)-3-(4-methylphenyl)-2,5-dihydro-2-furanone;

4-(3-Methyl-4-methylsulfanylphenyl)-3-(4-isobutylphenyl)-2,5-dihydro-2-furanone;

4-(3-Methyl-4-methylsulfanylphenyl)-3-(4-methoxyphenyl)-2,5-dihydro-2-furanone;

4-(3-Methyl-4-methylsulfonylphenyl)-3-(3-methyl-4-methylsulfanyl-phenyl)-2,5-dihydro-2-furanone;

3-Phenyl-4-(3-methoxy-4-methylsulfanylphenyl)-2,5-dihydro-2-furanone;

4-(3-Methyl-4-methylsulfonylphenyl)-3-(4-isobutylphenyl)-2,5-dihydro-2-furanone;

4-(3-Methyl-4-methylsulfanylphenyl)-3-(4-trifluoromethylphenyl)-2,5-dihydro-2-furanone;

4-(3-Methyl-4-methylsulfonylphenyl)-3-(4-trifluorophenyl)-2,5-dihydro-2-furanone;

4-(2-Fluoro-4-methylsulfanylphenyl)-3-phenyl-2,5-dihydro-2-furanone;

4-(2-Fluoro-4-methylsulfonylphenyl)-3-phenyl-2,5-dihydro-2-furanone;

4-(4-Methylsulfanyl-3-chlorophenyl)-3-phenyl-2,5-dihydro-2-furanone;

3-(4-Methylsulfanylphenyl)-4-(3-chloro-4-methylsulfanylphenyl)-2,5-dihydro-2-furanone;

4-(4-Methylsulfanyl-3-chlorophenyl)-3-(3,4-difluorophenyl)-2,5-dihydro-2-furanone;

4-(4-Methylsulfanyl-3-fluorophenyl)-3-phenyl-2,5-dihydro-2-furanone;

4-(4-Methylsulfanyl-3-fluorophenyl)-3-(4-methylsulfanylphenyl)-2,5-dihydro-2-furanone;

4-(4-Methylsulfonyl-3-chlorophenyl)-3-phenyl-2,5-dihydro-2-furanone;

4-(4-Methylsulfanyl-3-chlorophenyl)-3-(4-methylphenyl)-2,5-dihydro-2-furanone;

4-(4-Methylsulfanyl-3-fluorophenyl)-3-(4-methylphenyl)-2,5-dihydro-2-furanone;

4-(4-Methylsulfonyl-3-fluorophenyl)-3-phenyl-2,5-dihydro-2-furanone;

4-(4-Methylsulfonyl-3-fluorophenyl)-3-(4-methylphenyl)-2,5-dihydro-2-furanone;

4-(2-Fluoro-4-methylsulfanylphenyl)-3-(4-trifluoromethylphenyl)-2,5-dihydro-2-furanone;

4-(2-Fluoro-4-methylsulfonylphenyl)-3-(4-trifluoromethylphenyl)-2,5-dihydro-2-furanone;

4-(3-Methyl-4-methylsulfonylphenyl)-3-(4-methylsulfanylphenyl)-2,5-dihydro-2-furanone;

4-(2-Fluoro-4-methylsulfonylphenyl)-3-(4-methylphenyl)-2,5-dihydro-2-furanone;

4-(2-Fluoro-4-methylsulfanylphenyl)-3-(4-isobutylphenyl)-2,5-dihydro-2-furanone;

4-(2-Fluoro-4-methylsulfonylphenyl)-3-(4-isobutylphenyl)-2,5-dihydro-2-furanone;

4-(3-Methyl-4-methylsulfonylphenyl)-3-(4-methoxyphenyl)-2,5-dihydro-2-furanone;

4-(4-Methylsulfanyl-3-fluorophenyl)-3-(4-methoxyphenyl)-2,5-dihydro-2-furanone;

4-(4-Methylsulfonyl-3-fluorophenyl)-3-(4-methoxyphenyl)-2,5-dihydro-2-furanone;

4-(4-Methylsulfonyl-2-chlorophenyl)-3-(4-methoxyphenyl)-2,5-dihydro-2-furanone;

4-(2-Fluoro-4-methylsulfonylphenyl)-3-(3-methyl-4-methylsulfanylphenyl)-2,5-dihydro-2-furanone;

4-(2-Fluoro-4-methylsulfanylphenyl)-3-(4-fluorophenyl)-2,5-dihydro-2-furanone;

4-(4-Methylsulfonyl-3-chlorophenyl)-3-(3,4-difluorophenyl)-2,5-dihydro-2-furanone;

4-(4-Methylsulfanyl-2-chlorophenyl)-3-(4-methoxyphenyl)-2,5-dihydro-2-furanone;

4-(2-Fluoro-4-methylsulfonylphenyl)-3-(4-fluorophenyl)-2,5-dihydro-2-furanone;

4-(2,3-Dimethyl-4-methylsulfonylphenyl)-3-phenyl-2,5-dihydro-2-furanone;

4-(3-Fluoro-4-methylsulfanylphenyl)-3-(3-methyl-4-sulfanylphenyl)-2,5-dihydro-2-furanone;

4-(3-Fluoro-4-methylsulfonylphenyl)-3-(3-methyl-4-methylsulfonylphenyl)-2,5-dihydro-2-furanone;

4-(3-Methyl-4-methylsulfonylphenyl)-3-(3-fluoro-4-methylphenyl)-2,5-dihydro-2-furanone;

4-(3-Methyl-4-methylsulfonylphenyl)-3-(4-ethylphenyl)-2,5-dihydro-2-furanone;

4-(3-Methyl-4-methylsulfonylphenyl)-3-(3,4-dimethylphenyl)-2,5-dihydro-2-furanone;

4-(3-Methyl-4-methylsulfonylphenyl)-3-(3-bromo-4-methoxyphenyl)-2,5-dihydro-2-furanone;

4-(2-Fluoro-4-methylsulfonylphenyl)-3-(3-fluorophenyl)-2,5-dihydro-2-furanone;

4-(3-Fluoro-4-methylsulfonylphenyl)-3-(3-methyl-4-methylsulfanylphenyl)-2,5-dihydro-2-furanone;

4-(2-Fluoro-4-methylsulfonylphenyl)-3-(1-naphthyl)-2,5-dihydro-2-furanone;

3-(3-Methyl-4-methoxyphenyl)-4-(3-methyl-4-methylsulfonylphenyl)-2,5-dihydro-2-furanone;

4-(3-Fluoro-4-methylsulfonylphenyl)-3-(4-fluorophenyl)-2,5-dihydro-2-furanone;

4-(3-Fluoro-4-methylsulfonylphenyl)-3-(3-methyl-4-methoxyphenyl)-2,5-dihydro-2-furanone;

4-(2-Fluoro-4-methylsulfonylphenyl)-3-(3-methyl-4-methoxyphenyl)-2,5-dihydro-2-furanone;

4-(2-Fluoro-4-methylsulfonylphenyl)-3-(3-fluorophenyl)-5,5-dimethyl-2,5-dihydro-2-furanone;

4-(2-Fluoro-4-methylsulfonylphenyl)-3-(4-fluorophenyl)-5,5-dimethyl-2,5-dihydro-2-furanone;

4-(2-Fluoro-4-methylsulfonylphenyl)-3-(3-methyl-4-methoxyphenyl)-5,5-dimethyl-2,5-dihydro-2-furanone;

4-(3-Methyl-4-methylsulfonylphenyl)-3-(3-fluorophenyl)-5,5-dimethyl-2,5-dihydro-2-furanone;

4-(3-Bromomethyl-4-methylsulfonylphenyl)-3-(4-fluorophenyl)-5,5-dimethyl-2,5-dihydro-2-furanone;

2-{5-[4-(4-Fluorophenyl)-2,2-dimethyl-5-oxo-2,5-dihydro-3-furanyl]-2-methylsulfonylbenzyl}-2,3-dihydrobenzo[d]isothiazol-3-oxo-1,1-dioxide;

4-(2-Fluoro-4-methylsulfonylphenyl)-5,5-dimethyl-3-(3-methyl-4-methylsulfonylphenyl)-2,5-dihydro-2-furanone;

5-Ethyl-4-(3-fluoro-4-methylsulfonylphenyl)-3-(3-fluorophenyl)-2,5-dihydro-2-furanone;

3-(4-Fluorophenyl)-5,5-dimethyl-4-(4-methylsulfonyl-3-morpholinomethylphenyl)-2,5-dihydro-2-furanone;

5-Ethyl-4-(3-fluoro-4-methylsulfonylphenyl)-3-(4-fluorophenyl)-2,5-dihydro-2-furanone;

3-(3,4-Difluorophenyl)-4-(2-fluoro-4-methylsulfonylphenyl)-2,5-dihydro-2-furanone;

3-(3,5-Difluorophenyl)-4-(2-fluoro-4-methylsulfonylphenyl)-2,5-dihydro-2-furanone;

5-Ethyl-4-(3-fluoro-4-methylsulfonylphenyl)-3-(3-methyl-4-methylsulfanylphenyl)-2,5-dihydro-2-furanone;

3-Isopropoxy-5,5-dimethyl-4-(3-methyl-4-methylsulfonylphenyl)-2,5-dihydro-2-furanone;

4-(3-Hydroxymethyl-4-methylsulfonylphenyl)-3-isopropoxy-5,5-dimethyl-2,5-dihydro-2-furanone;

5-Ethyl-4-(3-fluoro-4-methylsulfonylphenyl)-3-(3-methyl-4-methylsufanylphenyl)-5-hydroxy-2,5-dihydro-2-furanone;

5-Ethyl-4-(3-fluoro-4-methylsulfonylphenyl)-3-(4-methoxy-3-methylphenyl)-2,5-dihydro-2-furanone;

5-Ethyl-4-(3-fluoro-4-methylsulfonylphenyl)-3-(3,4-difluorophenyl)-2,5-dihydro-2-furanone;

3-(3,4-Difluorophenyl)-5-ethyl-4-(2-fluoro-4-methylsulfonylphenyl)-2,5-dihydro-2-furanone;

3-(3,4-Difluorophenyl)-5-ethyl-4-(2-fluoro-4-methylsulfonylphenyl)-5-hydroxy-2,5-dihydro-2-furanone;

4-(3-Fluoromethyl-4-methylsulfonylphenyl)-3-isopropoxy-5,5-dimethyl-2,5-dihydro-2-furanone;

3-Isopropoxy-5,5-dimethyl-4-(3-fluoro-4-methylsulfonylphenyl)-2,5-dihydro-2-furanone;

3-Isopropoxy-5,5-dimethyl-4-(3-methylsulfanyl-4-methylsulfonylphenyl)-2,5-dihydro-2-furanone;

3-Isopropoxy-4-(3-methoxymethyl-4-methylsulfonylphenyl)-5,5-dimethyl-2,5-dihydro-2-furanone;

4-(3-Formyl-4-methylsulfonylphenyl)-3-isopropoxy-5,5-dimethyl-2,5-dihydro-2-furanone;

4-(3-Fluoro-4-methylsulfonylphenyl)-3-(3-methyl-4-methylsulfonylphenyl)-2,5-dihydro-2-furanone;

5-Ethyl-4-(2-fluoro-4-methylsulfonylphenyl)-3-(4-fluorophenyl)-5-hydroxy-2,5-dihydro-2-furanone;

5-Ethylidene-4-(2-fluoro-4-methylsulfonylphenyl)-3-(3-fluorophenyl)-2,5-dihydro-2-furanone;

5-Ethylidene-4-(2-fluoro-4-methylsulfonylphenyl)-3-phenyl-2,5-dihydro-2-furanone;

5-Ethylidene-4-(2-fluoro-4-methylsulfonylphenyl)-3-(3-methyl-4-methoxyphenyl)-2,5-dihydro-2-furanone;

4-(3-Fluoro-4-methylsulfonylphenyl)-3-(4-fluorophenyl)-5-methyl-2,5-dihydro-2-furanone;

4-(3-Fluoro-4-methylsulfonylphenyl)-3-(3-fluorophenyl)-5-methyl-2,5-dihydro-2-furanone;

4-(2-Fluoro-4-methylsulfonylphenyl)-3-(4-fluorophenyl)-5-methyl-2,5-dihydro-2-furanone;

4-(2-Fluoro-4-methylsulfonylphenyl)-3-(3-fluorophenyl)-5-methyl-2,5-dihydro-2-furanone;

4-(2-Fluoro-4-methylsulfonylphenyl)-3-(3,4-difluorophenyl)-5-methyl-2,5-dihydro-2-furanone;

4-(2-Fluoro-4-methylsulfonylphenyl)-3-(3-fluorophenyl)-5-methoxy-5-methyl-2,5-dihydro-2-furanone;

4-(2-Fluoro-4-methylsulfonylphenyl)-3-(4-methylphenyl)-5-methyl-2,5-dihydro-2-furanone;

4-(2-Fluoro-4-methylsulfonylphenyl)-3-(4-fluorophenyl)-5-methoxy-5-methyl-2,5-dihydro-2-furanone;

1-(4-Fluorophenyl)-4-(3-methyl-4-methylsulfonylphenyl)-3-phenyl-2,5-dihydro-1H-2-azolone and 3-(2-Fluoro-4-methylsulfonylphenyl)-1-(4-fluorophenyl)-4-phenyl-2,5-dihydro-1H-2,5-azoledione.

Accordingly, the compounds of general formula (I) where $R^1$, $R^2$, $R^3$, $R^4$, $R^5$, $R^6$, X and m are as defined earlier can be prepared by any of the following routes shown in Scheme I below:

Scheme-I

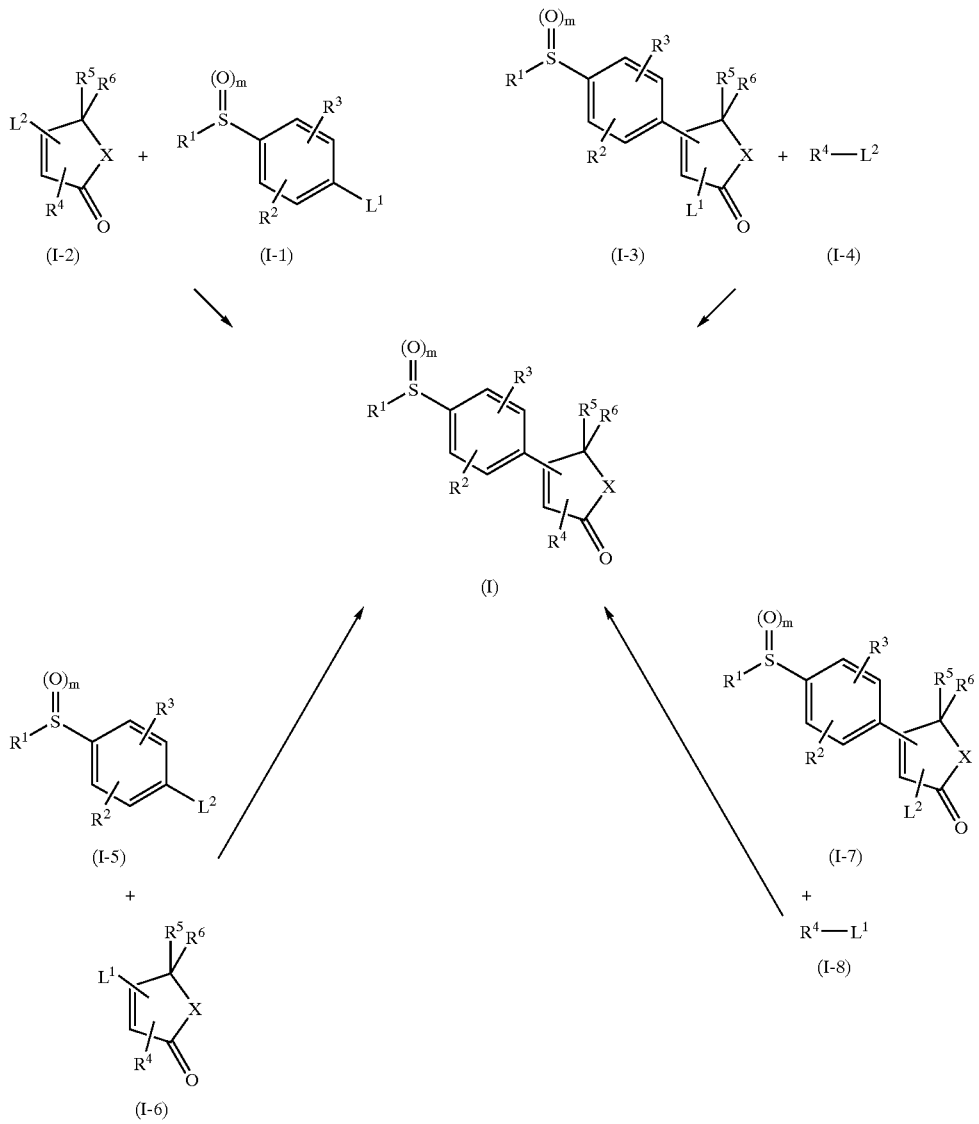

The reaction of a compound of formula (I-1) with a compound of (I-2) or the reaction of formula (I-3) with a compound of formula (I-4) or the reaction of a compound of formula (I-5) with a compound of formula (I-6) or the reaction of formula (I-7) with a compound of formula (I-8) where $L^1$ represents $B(OR)_2$, wherein R represents hydrogen or $(C_1-C_6)$alkyl group, $L^2$ represents halogen atom such as chlorine, bromine or iodine, or other leaving groups such as $ZnCl_2$ or triflate and all other symbols are as defined above to produce a compound of formula (I), where all symbols are as defined above may be carried out in the presence of solvents such as toluene, dimethylformamide (DMF), dioxane, tetrahydrofuran (THF), isopropanol, ethanol, dimethylsulfoxide (DMSO), dichloromethane (DCM), water and the like or mixtures thereof. The reaction may be carried out in an inert atmosphere which may be maintained by using inert gases such as He, $N_2$, Ar and the like. The reaction may be carried out in the presence of a catalyst such as bis(triphenyl phosphine)palladium(II)chloride, 1,4-bis (diphenyl phosphine butane)palladium (II)chloride, bis (dibenzylideneacetone)palladium(o), palladium acetate, palladium acetate-tri(o-tolyl)phosphine, bis(acetonitrile) palladium(II)chloride, palladium on carbon+triphenyl phosphine, tetrakis(triphenylphosphine)palladium(o) and the like. The amount of catalyst used may range from 0.1 mol % to 50 mol %, preferably from 1 to 10 mol %. The reaction may be effected in the presence of a base such as alkali metal carbonates like sodium carbonate or potassium carbonate; alkali metal bicarbonates like sodium bicarbonate or potassium bicarbonate; organic bases like triethylamine, pyridine, dimethylaminopyridine (DMAP) or di-isopropylethylamine and the like. The amount of base may range from 1 to 20 equivalents, preferably the amount of base ranges from 1 to 5 equivalents. Phase transfer catalysts such as tetraalkylammonium halide, benzyl triethylammonium halide, benzyl tributylammonium halide, tetraalkylammonium bisulfate, benzyl triethylammonium bisulfate or benzyl tributylammonium bisulfate may be employed. The amount of phase transfer catalyst used may range from 0.01 equivalents to 1 equivalent, preferably from 0.05 to 0.5 equivalents. The reaction temperature may range from 0° C. to reflux temperature of the solvent, preferably from 30° C. to reflux temperature of the solvent. The duration of the reaction may range from 0.5 to 76 hours, preferably from 6 hours to 24 hours.

In yet another feature of the present invention, the compounds of general formula (I) where $R^1$, $R^2$, $R^3$, $R^4$, $R^5$, $R^6$, X and m are as defined earlier may be prepared by any of the following routes shown in Scheme-II below:

gases such as $N_2$, Ar or He. The duration of the reaction may range from 2 to 80 hours.

The reaction of compound of formula (II-2), where $L^3$ represents halogen atom such as chlorine, bromine or iodine, and all other symbols are as defined above, with the compound of formula (II-3) where X represents oxygen or $NR^8$ and $R^4$ is as defined earlier or the reaction of a compound of Scheme-II

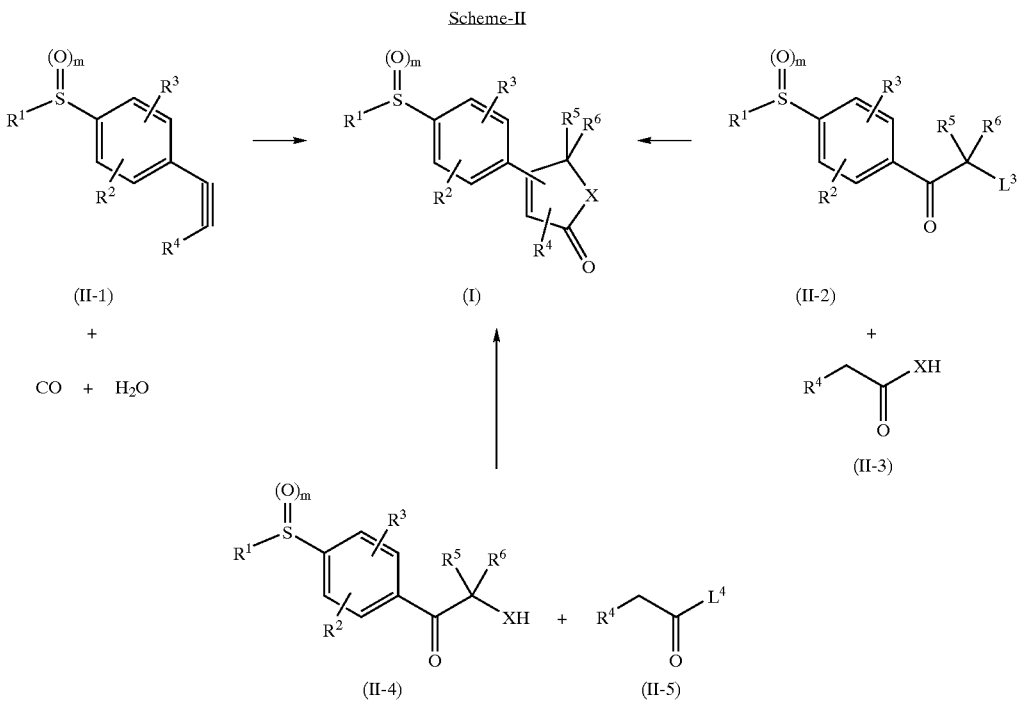

The reaction of compound of formula (II-1) where all symbols are as defined above with carbon monoxide and water to produce compound of the formula (I) where X represents oxygen and all other symbols are as defined earlier may be carried out in the presence of suitable palladium catalyst such as $PdCl_2$, $Pd(OAc)_2$, $(PPh_3)PdCl_2$ and the like. The amount of catalyst may range from 0.01 mol % to 5 mol % preferably 2.0 mol %. The reaction may be carried out in the presence of aqueous mineral acids such as HCl or HBr; protic solvents such as EtOH, i-PrOH or BuOH. The reaction temperature may be in the range of −78° C. to 300° C., preferably at a temperature in the range of 20° C. to reflux temperature of the solvent used and the reaction may be carried out at 50 to 150 atmospheric pressure of carbon monoxide. The duration of the reaction may range from 2 to 80 hours.

Alternatively, the compound of formula (I), where X represents oxygen and all symbols are as defined earlier, may be prepared by reacting a compound of formula (II-I), where all symbols are as defined earlier, with transition metal carbonyl complexes like $Rh_4(CO)_{12}$ or $Rh_6(CO)_{16}$. The reaction may be carried out in the presence of solvents such as THF, acetone, acetonitrile, benzene, toluene, EtOH, MeOH and the like or mixtures thereof. The reaction may be carried out in the presence of a base such as trialkyl amine like triethyl amine, di-isopropyl ethylamine and the like. The temperature may range from 30° C. to 300° C., preferably at a temperature in the range of 50° C.–150° C. at 20 to 300 atmosphere of pressure. The reaction may be carried out in an inert atmosphere which may be maintained by using inert formula (II-4) where X represents oxygen or $NR^8$ and all other symbols are as defined earlier with a compound of formula (II-5) where $L^4$ represents hydroxy, halogen atom such as chlorine, bromine or iodine to produce a compound of formula (I) where all symbols are as defined earlier may be carried out in the presence of base such as triethylamine (TEA), di-isopropylamine, di-isopropylethylamine, pyridine, piperidine, DMAP, 1,8-diazabicyclo[5.4.0]undec-7-ene (DBU), lithium diisopropylamide (LDA), potassium bis-(trimethyl silyl)amide, $Na_2CO_3$, $K_2CO_3$, NaOH, KOH, NaOMe, NaOEt, NaOiPr, t-BuOK, NaH, KH and the like. The amount of base may range from 1 to 5 equivalents, preferably the amount of base ranges from 2 to 3 equivalents. The reaction may be carried using solvents such as THF, N-methyl pyrrolidine, acetonitrile, propionitrile, acetone, 2-butanone, DMSO, DMF, dimethylamine (DMA), DCM, $CHCl_3$ and the like or mixtures thereof. The reaction may be carried in an inert atmosphere which may be carried out using inert gases such as He, $N_2$, Ar and the like. The reaction temperature may be in the range of 0° C. to 150° C., preferably at a temperature in the range of 20° C. to reflux temperature of the solvent used. The duration of the reaction may range from 2 to 50 hours, preferably from 2 to 20 hours. In case of incomplete dehydration, the hydrated compound is further dehydrated.

Alternatively, the reaction of compound of formula (II-2) where $L^3$ represents a halogen atom such as chlorine, bromine or iodine, and all other symbols are as defined above with a compound of formula (II-3) where X represents oxygen or $NR^8$ and $R^4$ is as defined earlier or the reaction of a compound of formula (II-4) where X represents oxygen or NR$^8$ and all other symbols are as defined earlier with a compound of formula (II-5) where L$^4$ represents hydroxy, halogen atom such as chlorine, bromine or iodine to produce a compound of formula (I) where all symbols are as defined earlier may be carried out in the presence of 2 equivalents of N,N1-dicyclohexylcarbodiimide (DCC)+0.5 equivalents of DMAP or carboxymethylcellulose (CMC)+DMAP. The reaction may be carried out in the presence of solvents such as DCM, CHCl$_3$, benzene, toluene, xylene, and the like or mixtures thereof. The reaction temperature may be in the room temperature to reflux temperature of the solvents used. The duration of the reaction may range from 2 to 12 h.

According to another feature of the present invention, the compound of formula (I) where R$^1$ represents amino group, m represents 2 and all other symbols are as defined above may be prepared by transforming a compound of formula (I) where R$^1$ represents lower alkyl group, m represents 2 and all other symbols are as defined earlier in the presence of a Grignard reagent like MeMgCl, MeMgBr, EtMgCl or a base such as nBuLi, LiNH$_2$ or LDA. The reaction may be carried out in the presence of trialkyl borane such as triethyl borane or tributyl borane in the presence of a solvent such as dioxane, diethylether, di-isobutylether, diphenylether, THF and the like or mixtures thereof. The reaction may be carried out in inert atmosphere which may be maintained by using Ar, N$_2$ or He. The reaction may be carried out in the temperature range of −78° C. to the reflux temperature of solvent used, preferably at 0° C. to reflux temperature of the solvent used. The reaction may be more effective under anhydrous condition. The duration of the reaction may be in the range of 12 to 72 hours, preferably in the range of 15 to 24 hours. The oxidative amination reaction may be carried out in presence of hydroxylamine-O sulfonic acid and NaOAc. The temperature range of 0° C. to reflux temperature of the solvent, preferably 0° C. to 50° C. may be used. The duration of the reaction may be 2 to 20 hours, preferably 2 to 10 hours.

According to another feature of the present invention the compound of formula (I) where all symbols are as defined earlier and m represents 0 may be prepared by reducing a compound of formula (I) where all symbols are as defined earlier and m represents 1 or 2. The reduction may be carried out using reagents such as LAH, HI, Bu$_3$SnH, TiCl$_2$, MeSiCl$_3$, NaI, PCl$_3$, H$_2$-Pd—C, acetyl chloride, PPh$_3$, t-BuBr and tris(dimethylamino)phosphine-I$_2$. The reduction may also be carried out using diisobutyl aluminium hydride [(iBu)$_2$AlH], LAH according to the procedure described in J. Org. Chem. 48, (1983) 1617.

In yet another embodiment of the present invention, the compound of formula (I) where all symbols are as defined earlier and m represents 1 (sulfoxide) or m represents 2 (sulfone) may be prepared by oxidising a compound of formula (I) where all symbols are as defined earlier and m represents 0 with a suitable oxidising agent. The oxidation of a compound of formula (I) where m is 0 may be carried out in the presence of an oxidising agent such as 30% H$_2$O$_2$, m-CPBA, oxone (potassium peroxy monosulfate), NaIO$_4$, KMnO$_4$, sodiumperborate, magnesium monoperoxy phthalate hexahydrate and the like. The quantity of the reagent varies from 2 mol to 20 mol preferably 4 to 10 mol. The reaction may be effective in presence of a solvent such as CHCl$_3$, t-butanol, CH$_2$Cl$_2$, acetone, CH$_3$COOH and the like or mixtures thereof. Water may be used as cosolvent. The reaction may be carried out in inert atmosphere which may be maintained by using He, N$_2$ or Ar. The reaction may be carried out at temperature in the range of 0° C. to 150° C., preferably in the range of 30° C. to 120° C. The duration of the reaction may range from 0.5 to 24 hours, preferably 0.5 to 12 hours.

In yet another embodiment of the present invention the compound of general formula (II-2) where L$^3$ represents halogen atom, R$^1$ and R$^2$ together with the atoms which they are attached forms a ring and the ring is selected from dihydrothiophene, R$^5$, R$^6$ represent hydrogen and R$^3$ is as defined earlier, may be prepared by a process shown in the Scheme-III below:

Scheme-III

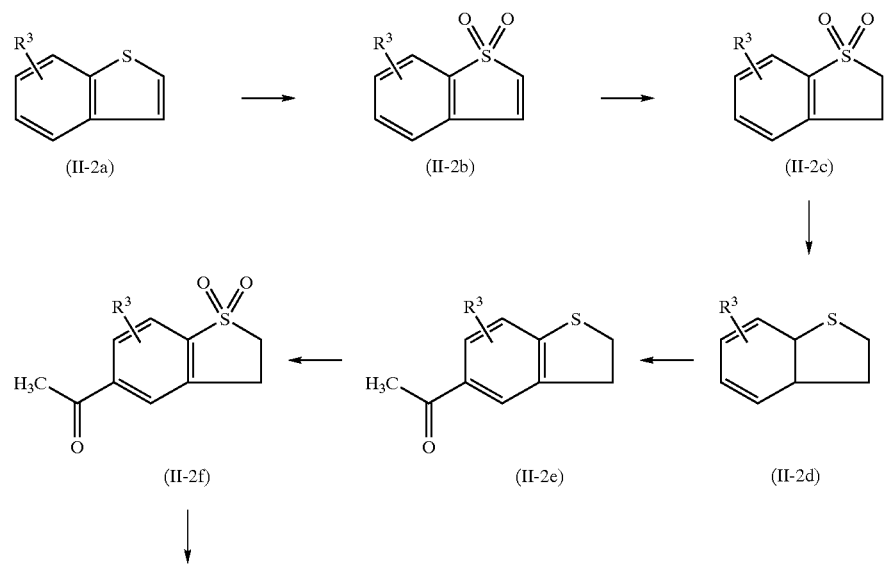

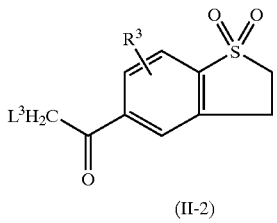

(II-2)

The oxidation of compound of formula (II-2a) where $R^3$ is as defined above to produce a compound of formula (II-2b) where $R^3$ is as defined above may be carried out using oxidizing agents such as hydrogenperoxide, potassium permanganate, meta chloro per benzoic acid (m-CPBA), $NaIO_4$, t-BuOCl, sodium perborate, potassium hydrogen persulfate and the like. The quantity of oxidizing agent used may vary from 1 to 20 equivalents, preferably 2–10 equivalents. The reaction may be carried out in the presence of solvents such as glacial acetic acid, propionic acid, water and the like or mixtures thereof. The reaction may be carried out in an inert atmosphere which is maintained by using inert gases such as He, $N_2$ or Ar. The reaction temperature may range from 20° C. to reflux temperature of solvent used, preferably from 50° C. to the reflux temperature of the solvent used. The duration may vary from 15 min to 15 h, preferably 15 min to 3 h.

The reduction of compound of formula (II-2b) defined above to a compound of formula (II-2c) where $R^3$ is as defined above, may be carried out using 5–10% Pd—C. catalyst, Raney-Nickel, Pt/C, Nickel boride and the like. The quantity of catalyst may vary from 0.01 to 1.0% w/w, preferably from 0.01 to 0.50% w/w. The reaction may be carried out in the presence of solvents such as acetic acid, methanol, ethanol and the like or mixtures thereof. The reaction may be effected in $H_2$ atmosphere, the pressure varying from 1 to 20 atm, preferably 1 to 10 atm. The reaction may be carried out in an inert atmosphere which is maintained by using inert gases such as He, $N_2$ or Ar. The reaction temperature may range from 15 to 100° C., preferably from 15 to 50° C. The duration of the reaction may vary from 0.5 to 20 h, preferably from 0.5 to 5 h.

The reduction of compound of formula (II-2c) defined above to a compound of formula (II-2d) where $R^3$ is as defined above, may be carried out using reducing agents such as LAH, HI, $Bu_3SnH$, $TiCl_2$, $MeSiCl_3$, NaI, $PCl_3$, $H_2$-Pd/C, $PPh_3$, t-BuBr, tris(dimethylamino)phosphine-$I_2$ and the like. The quantity of reducing agent may vary from 0.5 to 10 equivalents, preferably from 1 to 5 equivalents. The reaction may be carried out in the presence of solvents such as ($C_1$–$C_8$ linear or branched) alkylether, THF, dioxane and the like. The reaction may be carried out in an inert atmosphere, which is maintained by using inert gases such as He, $N_2$ or Ar. The reaction temperature may range from 0° C. to the reflux temperature of the solvent used and the duration of reaction ranges from 1 to 80 h, preferably from 1 to 24 h. The reaction may be carried out under anhydrous conditions.

The reaction of compound of formula (II-2d) defined above with acetyl chloride to produce a compound of formula (II-2e) where $R^3$ is as defined above, may be carried out in the presence of solvents such as dichloromethane, ethylene dichloride, chloroform, nitrobenzene and the like or mixtures thereof. The quantity of acetyl chloride may vary from 1 to 10 equivalents, preferably 1 to 5 equivalents. The reaction may be effected using catalysts such as $Al.Hal_3$ (where Hal is F, Cl or Br). The quantity of the catalyst may range from 1 to 10 equivalents, preferably 1 to 5 equivalents. The reaction may be carried out in an inert atmosphere which is maintained by using inert gases such as He, $N_2$ or Ar. The temperature of the reaction may range from –20° C. to the reflux temperature of the solvent used, preferably –20° C. to 50° C. The duration of the reaction may vary from 1 to 80 h, preferably from 4 to 24 h.

The oxidation of compound of formula (II-2e) defined above to produce a compound of formula (II-2f) where $R^3$ is as defined above may be carried using oxidizing agents such as hydrogenperoxide, potassium permanganate, m-CPBA, $NaIO_4$, t-BuOCl, sodium perborate, potassium hydrogen persulfate and the like. The quantity of oxidizing agent used may vary from 1 to 20 equivalents, preferably 2–10 equivalents. The reaction may be carried out in the presence of solvents such as glacial acetic acid, propionic acid, water and the like or mixtures thereof. The reaction may be carried out in an inert atmosphere, which is maintained by using inert gases such as He, $N_2$ or Ar. The reaction temperature may range from 20° C. to reflux temperature of solvent used, preferably from 50° C. to the reflux temperature of the solvent used. The duration may vary from 15 min to 15 h, preferably 15 min to 3 h.

The reaction of compound of formula (II-2f) defined above to produce a compound of formula (II-2) where $L^3$ represents halogen atom and all other symbols are as defined above may be carried out using halogenating agent such as NIS, NBS, bromine, Cu-Hal where Hal represents halogen atom in the quantity varying from 0.5 to 5 equivalents, preferably 0.5 to 1.5 equivalents, in the presence of solvents such as acetic acid, methanol, toluene, dichloromethane. The reaction may be effected in the presence of catalyst such as HBr, HCl in the quantity varying form 0.01 to 1.0% w/w, preferably 0.01 to 0.5% w/w. The temperature of the reaction may range from 15° C. to reflux temperature of the solvent used, preferably from 15 to 75° C. The duration of the reaction may vary from 1 to 20 h, preferably from 1 to 10 h.

It is appreciated that in any of the above-mentioned reactions, any reactive group in the substrate molecule may be protected according to conventional chemical practice. Suitable protecting groups in any of the above mentioned reactions are those used conventionally in the art. The methods of formation and removal of such protecting groups are those conventional methods appropriate to the molecule being protected.

The compound of formula (I) when produced through an intermediate compound, conventional functional group transformations such as hydrolysis, reduction or oxidation may be carried out.

The following examples illustrate some of the functional group transformations:

The compounds of formula (I) having $CONH_2$ groups may be transformed to CN by following a procedure disclosed in International publication WO No. 99/15505

Similarly, the compound of formula (I) having $CO_2Et$ group may be transformed to $CH_2OH$ by following a procedure disclosed in International publication No. WO 95/15316.

The pharmaceutically acceptable salts are prepared by reacting the compounds of formula (I) wherever applicable with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixture of solvents may be used. Organic bases like lysine, arginine, diethanolamine, choline, tromethamine, guanidine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used. The salts of amino acid groups and other groups may be prepared by reacting the compounds of formula (I) with the respective groups in solvents like alcohols, ketones, ether etc. Mixture of solvents may be used.

The stereoisomers of the compounds of formula (I) forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid and the like or chiral bases such as brucine, cinchona alkaloids and their derivatives and the like.

The regioiosmers of compound of formula (I) may be prepared by modifying the reaction conditions, use of reagents like acid to base or base to acid or by reaction with free base hydrazine instead of its salt with diketone. The molar proportion also can change the regiosiomer formation.

Various polymorphs of compound of general formula (I) forming part of this invention may be prepared by crystallization of compound of formula (I) under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or slow cooling. The presence of polymorphs may be determined by solid probe NMR spectroscopy, IR spectroscopy, differential scanning calorimetry, powder X-ray data or such other techniques.

Pharmaceutically acceptable solvates of compound of formula (I) forming part of this invention may be prepared by conventional methods such as dissolving the compounds of formula (I) in solvents such as water, methanol, ethanol etc., preferably water and recrystallizing by using different crystallization techniques.

The compounds of the general formula (I) are useful as partial or complete substitute for NSAIDS in compositions or preparations wherein they are presently coadministered with other agents or ingredients. The present invention also comprises pharmaceutical compositions for treating cyclooxygenase mediated diseases as defined earlier, comprising a non-toxic therapeutically effective amount of the compound of formula (I) as defined above and pharmaceutically acceptable carrier and optionally containing one or more other therapeutic ingredients such as another analgesic agent like acetaminophen, phenacetin, a potentiator like caffeine, a $H_2$ antagonist, aluminum or magnesium hydroxide, simethicone, a decongestant such as phenylephrine, phenyl propanolamine, pseudophedrine, oxymetazoline, epinephrine, nephazoline, propylhexadrine or leavo-desoxyephedrine, xylomatazoline, a sedating or non sedating antihistamine, an antitussive such as dextromethorphan, carbetapentane, caramiphen, hydrocodeine and codeine and the like, or a diuretic agent. The present invention also comprises a method of treatment of cyclooxygenase mediated diseases comprising administering to a patient in need thereof, a nontoxic therapeutically effective amount of compounds of formula (I) or pharmaceutical composition described above.

The pharmaceutical composition containing the active ingredient may be in the form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatine or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452 and 4,265,874 to form osmotic therapeutic tablets for control release.

Formulations for oral use may also be presented as hard gelatine capsules wherein the active ingredient is mixed with an inert solid diluent, for example, calcium carbonate, calcium phosphate or kaolin or as soft gelatine capsules wherein the active ingredients is mixed with water or an oil medium, for example peanut oil, liquid paraffin or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethycellulose, sodium alginate, polyvinyl-pyrrolidone, gum tragacanth and gum acacia; dispersing or wetting agents may be a naturally-occurring phosphatide, for example lecithin or condensation products of an alkylene oxide with fatty acids, for example polyoxyethylene stearate or condensation products of ethylene oxide with long chain aliphatic alcohols, for example heptadecaethylene-oxycetanol or condensation products of ethylene oxide with partial esters derived from fatty acids and a hexitol such as polyoxyethylene sorbitol monooleate or condensation products of ethylene oxide with partial esters derived from fatty acids and hexitol anhydrides, for example polyethylene sorbitan monooleate. The aqueous suspensions may also contain one or more preservatives, for example ethyl or n-propyl, p-hydroxybenzoate, one or more coloring agents, one or more flavouring agents and one or more sweetening agents, such as sucrose, saccharin or aspartame.

Oily suspensions may be formulated by suspending the active ingredient in a vegetable oil, for example arachis oil, olive oil, sesame oil or coconut oil or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and coloring agents, may also be present.

The pharmaceutical compositions of the invention may also be in the form of an oil-in-water emulsions. The oily phase may be a vegetable oil, for example olive oil or arachis oil or a mineral oil, for example liquid paraffin or mixtures of these. Suitable emulsifying agents may be naturally-occurring phosphatides, for example soy bean, lecithin and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parentally acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono or di glycerides. In addition, fatty acids such as oleic acid find use in the preparation of injectables.

Compounds of formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of Formula (I) are employed. (For purposes of this application, topical application shall include mouth washes and gargles).

Dosage levels of the order of from about 0.01 mg to about 140 mg/kg of body weight per day are useful in the treatment of the above-indicated conditions or alternatively about 0.5 mg to about 7 g per patient per day. For example, inflammation may be effectively treated by the administration of from about 0.01 to 50 mg of the compound per kilogram of body weight per day or alternatively about 0.5 mg to about 3.5 g per patient per day, preferably 2.5 mg to 1 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

The invention is explained in detail in the examples given below which are provided by way of illustration only and therefore should not be construed to limit the scope of the invention.

Preparation 1

3-Fluoroanisole

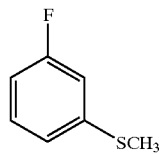

To an ice cold (~0° C.) solution of 3-fluoroaniline (50 g, 450.45 mmol) in 6 N hydrochloric acid (200 ml) was added 150 ml of ice cold (~5° C.) aqueous solution of $NaNO_2$ (37.3 g, 540.58 mmol) very slowly and drop wise. Temperature of the reaction mixture was maintained strictly at 0°–5° C. by occasional addition of ice and salts out side the reaction flask. The diazotised solution of 3-fluoroaniline was then added very slowly (not more than 2 ml at a time) to an aqueous solution of ethyl potassium xanthate (101.5 g, 634.37 mmol in 100 ml of $H_2O$) at 40°–45° C. The duration of addition was 1.5 h. The reaction mixture was then stirred for 1 h at 40°–45° C. The aqueous layer was decanted out from the orange colored oil that was extracted with chloroform (3×100 ml). The combined organic layers washed with 5 N NaOH solution (2×50 ml) followed by water (2×100 ml), dried over anhydrous $Na_2SO_4$ and concentrated under low vacuum. The crude oil thus obtained was used for the next step.

To the solution of above product in ethanol (250 ml) was added KOH pellets (37.91 g, 675.63 mmol) carefully. The mixture was then heated to 85°–90° C. under nitrogen atmosphere with vigorous stirring for 27 h. Ethanol was removed under low vacuum and the resulting residue was dissolved in acetone (200 ml). The mixture was cooled to ~10° C. to which methyl iodide (127.87 g, 900.87 mmol) was added slowly and drop wise. After stirring for 12 h at room temperature solvent was removed under vacuum and petroleum ether (200 ml) was added to the residue. Filtration of the mixture through celite followed by the concentration of the filtrate gave crude product which was purified by distillation at 83°–85° C. under 40 mm Hg to afford 31 g of title compound (49% yield) as oil.

$^1$H NMR (CDCl$_3$, 200 MHz): δ 7.29–7.18 (m, 1H), 7.02–6.77 (m, 3H), 2.48 (s, 3H).

Mass (CI, i-Butane) m/z 142 (M$^+$, 20), 96 (100).

Preparation 2

2-Fluorothioanisole

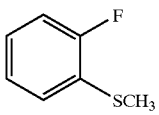

2-Fluorothioanisole was prepared in 71% yield from 2-fluoroaniline (30 g, 270.27 mmol) using NaNO$_2$ (22.37 g, 324.49 mmol), ethyl potassium xanthate (43.51 g, 271.4 mmol) and methyl iodide (76.72 g, 540.21 mmol) according to the procedure described in preparation 1.

$^1$H NMR (CDCl$_3$, 200 MHz): δ 7.36–7.00 (m, 4H), 2.47 (s, 3H).

Preparation 3

2,3-Dimethylthioanisole

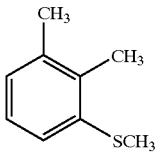

2,3-Dimethylthioanisole was prepared in 78% yield from 2,3-dimethylaniline (5 g, 41.32 mmol) using NaNO$_2$ (5.13 g, 74.37 mmol), ethyl potassium xanthate (7.90 g, 49.28 mmol) and methyl iodide (6.10 g, 42.95 mmol) according to the procedure described in preparation 1.

$^1$H NMR (CDCl$_3$, 200 MHz): δ 7.2–6.9 (m, 3H), 2.46 (s, 3H), 2.32 (s, 3H), 2.31 (s, 3H).

Preparation 4

2-Chlorothioanisole

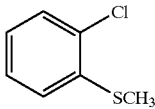

2-Chlorothioanisole was prepared in 89% yield from commercially available 2-chlorothiophenol (4.0 g, 27.6 mmol) using methyl iodide (4.66 g, 32.81 mmol) according to the procedure described in preparation 1.

$^1$H NMR (CDCl$_3$, 200 MHz): δ 7.31–6.92 (m, 4H), 2.46 (s, 3H).

Preparation 5

2-Fluoro-4-methylsulfanyl Acetophenone

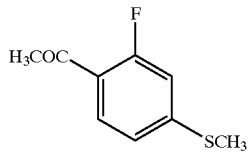

To a suspension of AlCl$_3$ (45 g, 339 mmol) in dichloromethane (150 ml) was added acetyl chloride (24.2 ml, 339 mmol) drop wise at 0° C. The mixture was stirred for 0.5 h at 25° C. until a clear solution was obtained. To this was added a solution 3-fluorothioanisole (37 g, 260.5 mmol) in dichloromethane (50 ml) slowly at 0° C. The duration of addition was 30 min. The mixture was then stirred for 3 h at 25° C., poured into ice (500 g), extracted with chloroform (3×100 ml). Combined organic layers were washed with water (2×100 ml), dried over anhydrous Na$_2$SO$_4$ and concentrated under vacuum to give crude product. This was purified by column chromatography over silica gel using 1% EtOAc-Petroleum ether as eluant to give 14 g (29% yield) of the title compound as light brown solid. m.p.: 61°–62° C.

$^1$H NMR (CDCl$_3$, 200 MHz): δ 7.85–7.77 (m, 1H), 7.06–7.01 (d, J=8.79 Hz, 1H), 6.90–6.86 (d, J=, 8.3 Hz, 1H), 2.62–2.60 (d, J=4.88 Hz, 3H), 2.52 (s, 3H).

Mass (CI, i-Butane) m/z 183 (M$^+$, 47), 169 (100), 155 (89).

Preparation 6

3-Fluoro-4-methylsulfanyl Acetophenone

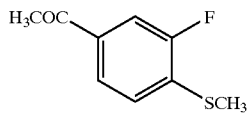

3-Fluoro-4-methylsulfanyl acetophenone was prepared in 22% yield from 2-fluorothioanisole (9 g, 63.38 mmol) using acetylchloride (5.97 g, 76.05 mmol) and AlCl$_3$ (10.11 g, 75.82 mmol) according to the procedure described in preparation 5.

$^1$H NMR (CDCl$_3$, 200 MHz): δ 7.72–7.50 (m, 2H), 7.30–7.15 (t, J=7.8 Hz, 1H), 2.56 (s, 3H), 2.51 (s, 3H).

Preparation 7

2,3-Dimethyl-4-methylsulfanyl Acetophenone

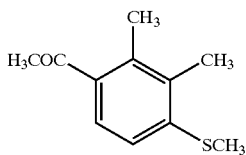

2,3-Dimethyl-4-methylsulfanyl acetophenone was prepared in 28% yield from 2,3-dimethylthioanisole (7.5 g, 49.01 mmol) using acetylchloride (4.60 g, 58.59 mmol) and AlCl$_3$ (7.80 g, 58.49 mmol) according to the procedure described in preparation 5.

$^1$H NMR (CDCl$_3$, 200 MHz): δ 7.54–7.49 (d, J=8.71 Hz, 1H), 6.75–6.65 (d, J=8.72 Hz, 1H), 2.55 (s, 3H), 2.49 (s, 3H), 2.42 (s, 3H), 2.30 (s, 3H).

Preparation 8

3-Chloro-4-methylsulfanyl Acetophenone

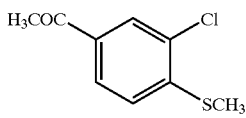

3-Chloro-4-methylsulfanyl acetophenone was prepared in 69% yield from 2-chlorothioanisole (5.0 g, 31.54 mmol) using acetylchloride (2.7 ml, 37.83 mmol) and AlCl$_3$ (4.56 g, 34.19 mmol) according to the procedure described in preparation 5.

$^1$H NMR (CDCl$_3$, 200 MHz): δ 7.90–7.71 (m, 2H), 7.17 (d, J=8.0 Hz, 1H), 2.55 (s, 2H), 2.52 (s, 3H).

Preparation 9

2-Bromo-1-(2-fluoro-4-methylsulfanylphenyl)-1-ethanone

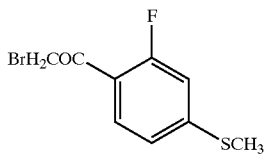

To a solution of 2-fluoro-4-methylsulfanyl acetophenone (12 g, 65.2 mmol) in acetic acid (100 ml) was add ed hydrobromic acid (5 ml) at 10°–15° C. The mixture was stirred for 10–15 min to this stirring mixture was added a solution of bromine (3.18 ml, 61.72 mmol) in acetic acid (4 ml) very slowly. Stirring continued for 3 h until the color of bromine disappeared. Water (300 ml) was added to this mixture, the solid separated was filtered and dried under vacuum. The powder thus obtained was treated with petroleum ether (20 ml) to remove color impurities and then filtered to give 13.3 g of title compound in 78% yield as pale brown solid.

m.p. 55°–59° C.

$^1$H NMR (CDCl$_3$, 200 MHz): δ 7.91–7.83 (m, 1H), 7.09–7.05 (d, J=8.7 Hz, 1H), 6.98–6.92 (d, J=12.2 Hz, 1H), 4.48–4.47 (d, J=1.96 Hz, 2H), 2.52 (s, 3H).

Mass (CI, i-Butane) m/z 262 (M$^+$, 8), 169 (100).

Preparation 10

2-Bromo-1-(3-fluoro-4-methylsulfanylphenyl)-1-ethanone

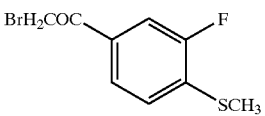

2-Bromo-1-(3-fluoro-4-methylsulfanylphenyl)-1-ethanone was prepared in 67% yield from 2-fluoro-4-methylsulfanyl acetophenone (2 g, 10.86 mmol) using bromine (0.58 ml, 11.25 mmol) according to the procedure described in preparation 9.

$^1$H NMR (CDCl$_3$, 200 MHz): δ 7.75–7.63 (m, 2H), 7.30–7.15 (t, J=7.40 Hz, 1H), 4.38 (s, 2H), 2.53 (s, 3H).

Preparation 11

2-Bromo-1-(2, 3-dimethyl-4-methylsulfanylphenyl)-1-ethanone

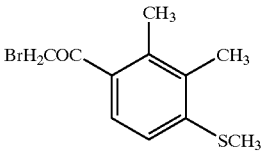

2-Bromo-1-(2,3-dimethyl-4-methylsulfanylphenyl)-1-ethanone was prepared in 79% yield from 2,3-dimethyl-4-methylsulfanyl acetophenone (1.8 g, 9.2 mmol) using bromine (0.45 ml, 8.73 mmol) according to the procedure described preparation 9.

$^1$H NMR (CDCl$_3$, 200 MHz): δ 7.78–7.56 (d, J=8.21 Hz, 1H), 6.89–6.76 (d, J=8.22 Hz, 1H), 4.31 (s, 2H), 2.51 (s, 3H), 2.43 (s, 3H), 2.33 (s, 3H).

Preparation 12

2-Bromo-1-(3-chloro-4-methylsulfanylphenyl)-1-ethanone

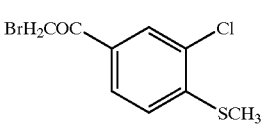

2-Bromo-1-(3-chloro-4-methylsulfanylphenyl)-1-ethanone as prepared in 55% yield from 3-chloro-4-methylsulfanyl acetophenone (6.6 g, 33 mmol) using bromine (1.60 ml, 31.01 mmol) according to the procedure described in preparation 9.

$^1$H NMR (CDCl$_3$, 200 MHz): δ 8.02–7.81 (m, 2H), 7.19 (d, J=8.0 Hz, 1H), 4.36 (s, 2H), 2.52 (s, 3H).

Preparation 13

Benzothiophene-1,1-dioxide

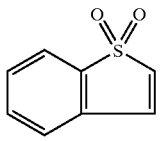

To a solution of benzothiophene (10 g, 74.6 mmol) in glacial acetic acid (18.65 ml) 30% aqueous $H_2O_2$ (37.31 ml, 329.20 mmol) was added and refluxed for 0.5 h. The reaction mixture was cooled slowly to 10°–15° C., filtered, washed with chilled water (15 ml) and dried to yield the title compound as white solid (12 g, 97%). m.p. 129°–130° C.

$^1$HNMR(CDCl$_3$, 200 MHz): δ 7.74 (d, J=7.80 Hz, IH), 7.68–7.54 (m, 2H), 7.38 (d, J=2.40 Hz, IH), 7.24 (d, J=7.00 Hz, IH), 6.72 (d, J=6.80 Hz, IH).

Preparation 14

2,3-Dihydrobenzothiophene-1,1-dioxide

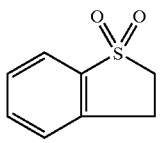

A solution of benzothiophene-1,1-dioxide (10 g, 60.24 mmol) obtained in preparation 13 dissolved in glacial acetic acid (400 ml) was charged with 5–10% Pd—C (100 mg, 0.01 wt %) and hydrogenated using $H_2$ gas for 5 h. The reaction mixture was filtered using celite bed and the filtrate poured into ice water (500 ml), extracted with ethylacetate, dried (Na$_2$SO$_4$) and evaporated to yield gummy mass which was chromatographed over silica gel column using ethylacetate:pet. ether (10:90) to yield the title compound (10 g, 99%). m.p. 91°–92° C.

$^1$HNMR (CDCl$_3$, 200 MHz): δ 7.76–7.73 (d, J=7.60 Hz, IH), 7.62–7.40 (m, 3H), 3.53–3.50 (t, J=6.20 Hz, 2H), 3.39–3.36 (t, J=6.00 Hz, 2H).

Preparation 15

2,3-Dihydrobenzothiophene

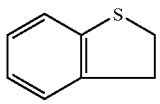

To 2,3-dihydrobenzothiophene-1,1-dioxide (10 g, 59.52 mmol) obtained in preparation 14, lithium aluminum hydride (5.65 g, 148.80 mmol) and THF (100 ml) was added under argon atmosphere and refluxed for 4–5 h. The reaction mixture was cooled to 10° C. and adding water dropwise slowly quenched excess lithium aluminum hydride. THF was removed under reduced pressure. Water (100 ml) and ethyl acetate (100 ml) was added and stirred. The water layer was extracted with ethyl acetate. The combined ethyl acetate layers were dried (Na$_2$SO$_4$) and evaporated to yield the crude product, which was chromatographed over silica gel column using 2% ethylacetate and pet. ether as eluent to afford the title compound as viscous liquid.

$^1$HNMR (CDCl$_3$, 200 MHz): δ 7.26–7.01 (m, 4H), 3.39–3.26 (m, 4H).

Preparation 16

5-Acetyl-2, 3-dihydrobenzothiophene

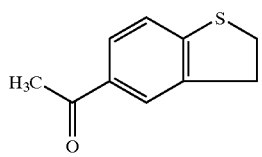

2,3-Dihydrobenzothiophene (8 g, 58.8 mmol) obtained in preparation 15 was slowly added to slurry of anhydrous aluminum chloride (11.77 g, 88.2 mmol) and acetylchloride (6.92 g, 88.2 mmol) in dichloromethane (100 ml) at 5°–10° C. The reaction mixture was stirred at 25°–30° C. for 24 h and then poured into crushed ice. Extracted with dichloromethane (2×50 ml), dried (Na$_2$SO$_4$) and evaporated to yield the title compound as viscous liquid (10 g, 96%).

$^1$HNMR (CDCl$_3$, 200 MHz): δ 7.77 (s, 1H), 7.74–7.70 (d, J=9.70 Hz, 1H), 7.28–7.24 (d, J=7.98 Hz, 1H), 3.47–3.34 (m, 4H), 2.55 (s, 3H).

Preparation 17

5-Acetyl-2,3-dihydrobenzothiophene-1,1-dioxide

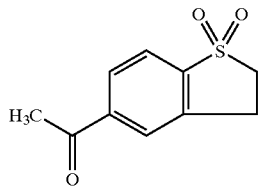

To a solution of 5-acetyl-2,3-dihydrobenzothiophene (8 g, 44.9 mmol) obtained in preparation 16 in glacial acetic acid (16 ml), 30% aqueous $H_2O_2$ solution (22.92 ml, 202.2 mmol) was added and refluxed for 1 h. After cooling to 20° C., the separated solid was filtered and washed with water to yield the title compound (9 g, 96%). m.p. 54°–56° C.

$^1$HNMR (CDCl$_3$, 200 MHz): 8.02 (m, 2H), 7.82 (d, J=8.20 Hz, IH), 3.57–3.51 (dt, J=5.60 Hz, 4H), 2.64 (s, 3H).

Preparation 18

5-Bromoacetyl-2,3-dihydrobenzothiophene-1,1-dioxide

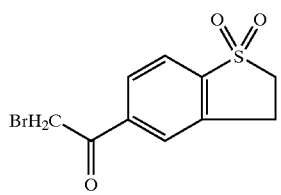

To a solution of 5-acetyl-2,3-dihydrobenzothiophene-1,1-dioxide (8 g, 38.1 mmol) (obtained in preparation 17)

dissolved in acetic acid (45 ml) under argon atmosphere, aqueous HBr (0.5 ml, 47%), bromine (5.84 g, 36.54 mmol) was added slowly at 15°–20° C. and the reaction mixture was stirred for about 0.5 h. Additional quantity of bromine (4.84 g) was slowly added and the stirring continued for further 10 h at 25°–30° C. Argon atmosphere was removed and the reaction mixture was kept open in the wave of blowing air in the fuming cup board to eliminate free bromine. The solid separated was filtered and washed with acetic acid (2×10 ml) followed by pet. ether to yield the title compound (10 g, 91%). mp. 68°–70° C.

$^1$HNMR (CDCl$_3$, 200 MHz): 8.06 (d, J=8.20 Hz, IH), 8.00 (s, IH), 7.86 (d, J=8.40 Hz, IH), 4.44 (s, 2H), 3.62–3.40 (dt, J=5.40 Hz, 4H).

Preparation 19

2-(4-Fluoroanilino)-1-(3-methyl-4-methylsulfonylphenyl)1-ethanone

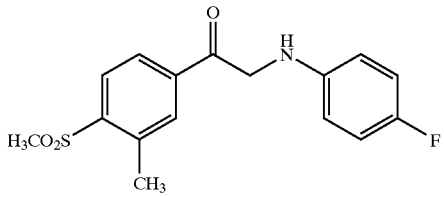

To a mixture of p-fluoroaniline (1.14 g, 10.3 mmol) and NaHCO$_3$ (0.865 g, 10.3 mmol) in ethanol (25 ml) was added 2-bromo-1-(3-methyl-4-methylsulfonyl) acetophenone (3 g, 10.3 mmol) under nitrogen atmosphere at 25° C. The mixture was stirred vigorously for 3.5 h at the same temperature and then diluted with water (100 ml). The solid separated was filtered, washed with water (2×25 ml) followed by petroleum ether (2×10 ml) and dried under vacuum to give 2.9 g of the title compound in 88% yield.

$^1$H NMR (CDCl$_3$, 200 MHz): δ 8.19–8.15 (d, J=8.7 Hz, 1H), 7.96–7.93 (m, 2H), 6.97–6.88 (m, 2H), 6.68–6.62 (m, 2H), 4.59 (s, 2H), 3.10 (s, 3H), 2.79 (s, 3H).

Preparation 20

2-(4-Fluoroanilino)-1-(2-fluoro-4-methylsulfonylphenyl)-1-ethanone

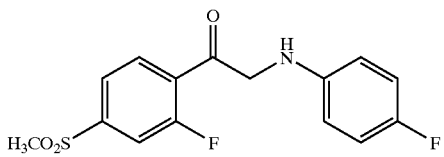

2-(4-Fluoroanilino)-1-(3-methyl-4-methylsulfonylphenyl)-1-ethanone was prepared in 95% yield using p-fluoroaniline (0.22 g, 1.96 mmol) and 2-bromo-1-(2-fluoro-4-methylsulfanylphenyl)-1-ethanone (0.6 g, 1.96 mmol) according to the procedure described in preparation 19.

$^1$H NMR (CDCl$_3$, 200 MHz): δ 8.22–8.14 (m, 1H), 7.85–7.78 (m, 2H), 6.95–6.87 (m, 2H), 6.65–6.59 (m, 2H), 4.55 (s, 2H), 3.09 (s, 3H).

Preparation 21

N$^1$-(4-Fluorophenyl)-N$^1$-[2-(3-methyl-4-methylsulfonylphenyl)-2-oxoethyl]-2-phenylacetamide

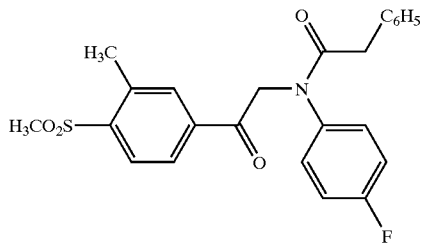

To a solution of 2-(4-fluoroanilino)-1-(3-methyl-4-methylsulfonylphenyl)-1-ethanone (1.5 g, 4.67 mmol) (obtained in preparation 19) in anhydrous THF (15 ml) was added phenacylchloride (0.722 g, 0.62 mmol) very slowly under nitrogen atmosphere at 25° C. The mixture was stirred for 2 h and diluted with water (25 ml). The solid separated was filtered, washed with water (2×15 ml) followed by petroleum ether (2×5 ml) and dried under vacuum to give 1.6 g of the title compound in 78% yield.

$^1$H NMR (CDCl$_3$, 200 MHz): δ 8.14–8.10 (d, J=8.8 Hz, 1H), 7.89–7.86 (m, 3H), 7.39–7.00 (m, 9H), 5.04 (s, 2H), 6.57 (s, 2H), 3.08 (s, 3H), 2.75 (s, 3H).

Preparation 22

N$^1$-(4-Fluorophenyl)-N$^1$-[2-(2-fluoro-4-methylsulfonylphenyl)-2-oxoethyl]-2-phenylacetamide

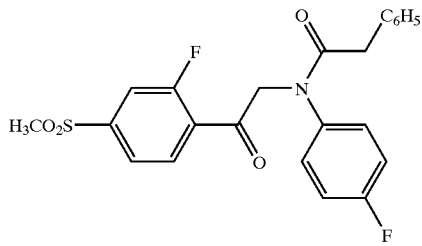

N$^1$-(4-Fluorophenyl)-N$^1$-[2-(3-methyl-4-methylsulfonylphenyl)-2-oxoethyl]-2-phenylacetaomide was prepared in 93% yield from 2-(4-fluoroanilino)-1-(2-fluoro-4-methylsulfonylphenyl)-1-ethanone (0.55 g, 1.84 mmol) and phenacyl chloride (0.285 g, 1.84 mmol) according to the procedure described in preparation 21.

$^1$H NMR (CDCl$_3$, 200 MHz): δ 8.18–8.11 (m, 1H), 7.84–7.73 (m, 2H), 7.35–7.04 (m, 9H), 4.95 (s, 2H), 3.56 (s, 2H), 3.08 (s, 3H).

EXAMPLE 1

3-(4-Fluorophenyl)-4-(2-fluoro-4-methylsulfonylphenyl)-2,5-dihydro-2-furanone

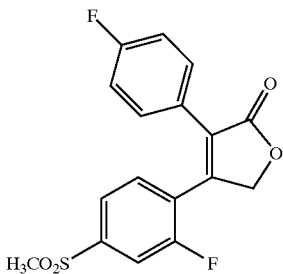

Step 1

Preparation of 2-(2-fluoro-4-methylsulfanylphenyl)-2-oxyethyl-2-(4-fluorophenyl) Acetate

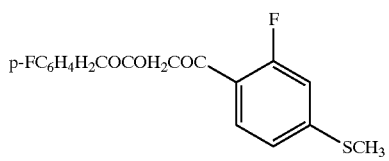

To a solution of 4-fluorophenylacetic acid (7.6 g, 49.3 mmol) in DMF (30 ml) was added aqueous solution of KOH (2.7 g, 48.11 mmol in 5 ml water) and the mixture was stirred at 25° C. for 30 min. To this mixture was added a solution of 2-Bromo-1-(2-fluoro-4-methylsulfanylphenyl)-1-ethanone (13 g, 49.3 mmol) in DMF (100 ml) and stirring continued for 1 h at 25° C. Water (500 ml) was added to this, the solid separated was filtered and dried under vacuum. The crude solid was treated with isopropanol and filtered to give 15 g of title compound in 90% yield as pale brown solid. m.p. 78°–81° C.

$^1$H NMR (CDCl$_3$, 200 MHz): δ 7.91–7.83 (t, J=7.8 Hz, 1H), 7.35–7.28 (m, 2H), 7.08–6.90 (m, 4H), 5.21–5.20 (d, J=3.42 Hz, 1H), 3.78 (s, 2H), 2.51 (s, 3H). Mass (CI, i-Butane) m/z 336 (M$^+$, 8), 169 (100).

Step 2

Preparation of 3-(4-fluorophenyl)-4-(2-fluoro-4-methylsulfanylphenyl)-2,5-dihydro-2-furanone

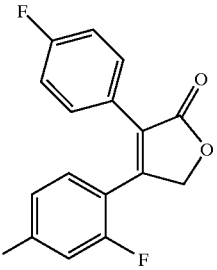

To a solution of 2-(2-fluoro-4-methylsulfanylphenyl)-2-oxyethyl-2-(4-fluorophenyl) acetate (12 g, 35.7 mmol) (obtained in step 1) in acetonitrile (100 ml) was added 1,8-diazabicyclo[5.4.0] undec-7-ene (DBU) (11 ml, 71.5 mmol) drop wise at 25° C. under nitrogen atmosphere. The mixture was stirred for 30 min. at same temperature. Water (200 ml) was added to this followed by the addition of 2 N HCl (200 ml). The mixture was then extracted with EtOAc (2×250 ml), organic layers were collected, combined, dried over anhydrous Na$_2$SO$_4$ and concentrated. The crude product thus obtained was purified by column chromatography over silica gel using 10% EtOAc-petroleum ether to give 5 g of the title compound in 44% yield as white solid. m.p. 118°–122° C.

$^1$H NMR (CDCl$_3$, 200 MHz): δ 7.45–7.38 (m, 2H), 7.25–6.87 (m, 5H), 5.17 (s, 2H), 2.48 (s, 3H).

Mass (CI, i-Butane) m/z 318 (M$^+$, 100), 261 (85).

Step 3

Preparation of 3-(4-fluorophenyl)-4-(2-fluoro-4-methylsulfonylphenyl)-2,5-dihydro-2-furanone.

To a solution of 3-(4-fluorophenyl)-4-(2-fluoro-4-methylsulfanylphenyl)-2,5-dihydro-2-furanone (6 g, 18.8 mmol) (obtained in step 2) in acetone (150 ml) was added a solution of oxone (34.8 g, 56.6 mmol) in water (75 ml). The reaction mixture was stirred vigorously for 2 h at 25° C. After completion of the reaction solvent was removed under low vacuum and water (200 ml) was added to it. The mixture was then extracted with EtOAc (2×100 ml), organic layers collected, combined, dried over anhydrous Na$_2$SO$_4$ and concentrated under vacuum. The crude product was then treated with MeOH (2×20 ml) and filtered to give 5.6 g of title compound in 85% yield as off white powder. m.p. 160°–162° C.

$^1$H NMR (CDCl$_3$, 200 MHz): δ 7.77–7.66 (m, 2H), 7.45–7.35 (m, 3H), 7.25–7.01 (m, 2H), 5.19 (s, 2H), 3.09 (s, 3H).

Mass (CI, i-Butane) m/z 350 (M$^+$, 50), 322 (10), 293 (100).

Examples 2–93 have been prepared by similar procedures described in Example 1.

| Example No. | Structure | Yield (%) & Purity (%) | Melting Point (° C.) | ¹HNMR Data |
|---|---|---|---|---|
| 2 | 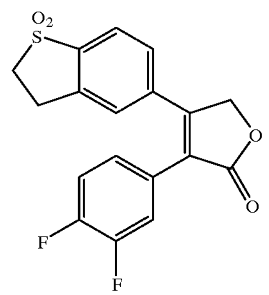 | 16 & 92 | Low melting | (CDCl$_3$, 200 MHz): δ 7.76 (d, J = 8Hz, 1H), 7.42–7.11(m, 5H), 5.10(s, 2H), 3.5(m, 2H), 3.30(m, 2H). |
| 3 | 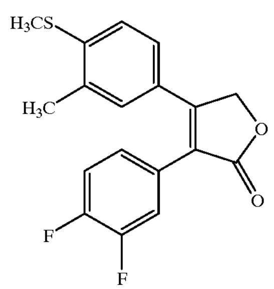 | 42 & 98.8 | 150–153 | (CDCl$_3$, 200 MHz): δ 7.25–7.0(m, 6H), 5.14(s, 2H), 2.47(s, 3H), 2.25(s, 3H). |
| 4 | 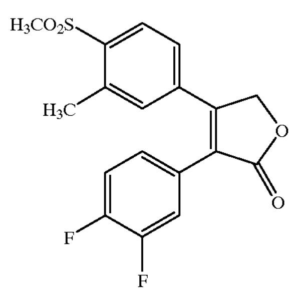 | 60 & 96.5 | 178–180 | (CDCl$_3$, 200 MHz): δ 8.0 (d, J = 7.82Hz, 1H), 7.3–7.1 (m, 5H), 5.1(s, 2H), 3.1(s, 3H), 2.6(s, 3H). |
| 5 | 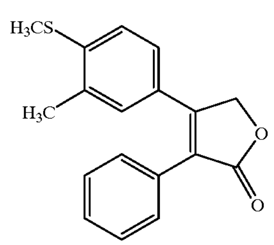 | 45 & 99 | 150–153 | (CDCl$_3$, 200 MHz): δ 7.46–7.0(m, 8H), 5.18(s, 2H), 2.48(s, 3H), 2.24(s, 3H). |
| 6 | 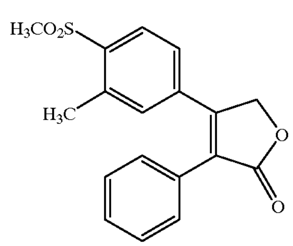 | 75 & 98 | 167–170 | (CDCl$_3$, 200 MHz): δ 8.05–7.95(d, J = 7.89Hz, 1H), 7.4(s, 5H), 5.18(s, 2H), 3.1(s, 3H), 2.64(s, 3H). |

-continued

Examples 2–93 have been prepared by similar procedures described in Example 1.

| Example No. | Structure | Yield (%) & Purity (%) | Melting Point (° C.) | ¹HNMR Data |
|---|---|---|---|---|
| 7 | H₃CS-, H₃C-, F (structure) | 76 & 92.5 | 126–130 | (CDCl₃, 200 MHz): δ 7.4–7.0(m, 7H), 5.14(s, 2H), 2.46(s, 3H), 2.23(s, 3H). |
| 8 | H₃CS-, H₃C-, H₃C (structure) | 82 & 94.5 | 144–147 | (CDCl₃, 200 MHz): δ 7.3–7.0(m, 7H), 5.1(s, 2H), 2.47(s, 3H), 2.38(s, 3H), 2.24(s, 3H). |
| 9 | H₃CO₂S-, H₃C-, F (structure) | 54 & 96.5 | 193–195 | (CDCl₃, 200 MHz): δ 8.03 (d, J = 8.00Hz, 1H), 7.43–7.12(m, 6H), 5.19(s, 2H), 3.1(s, 3H), 2.69(s, 3H). |
| 10 | H₃CO₂S-, H₃C-, H₃C (structure) | 65 & 92.6 | 164–167 | (CDCl₃, 200 MHz): δ 8.09–8.0(d, J = 7.88Hz, 1H), 7.31–7.24(m, 6H), 5.18(s, 2H), 3.12(s, 3H), 2.68(s, 3H), 2.4(s, 3H). |
| 11 | H₃CS-, H₃C-, isobutyl (structure) | 46 & 96.9 | 146–149 | (CDCl₃, 200 MHz): δ 7.35–7.31(d, J = 8.0Hz, 2H), 7.17–7.13(d, J = 8.3, 3H), 7.05–7.0(d, J = 8.3Hz, 2H), 5.14(s, 2H), 2.51–2.46(d, J = 9.13Hz, 2H), 2.46(s, 3H), 2.21(s, 3H), 2.0–1.8 (m, 1H), 0.93–0.9(d, J = 6.6Hz, 6H). |

-continued

Examples 2–93 have been prepared by similar procedures described in Example 1.

| Example No. | Structure | Yield (%) & Purity (%) | Melting Point (°C.) | ¹HNMR Data |
|---|---|---|---|---|
| 12 | H₃CS-, H₃C-, H₃CO- substituted diaryl furanone | 79 & 94.5 | 147–150 | (CDCl$_3$, 200 MHz): δ 7.41–7.37(d, J = 8.68Hz, 2H), 7.1–7.06(m, 3H), 6.93–6.89 (d, J = 8.7, 2H), 5.12(s, 2H), 3.83(s, 3H), 2.47(s, 3H), 2.24(s, 3H). |
| 13 | H₃CO₂S-, H₃C-, H₃CS-, CH₃ substituted diaryl furanone | 52 & 92.0 | 93–96 | (CDCl$_3$, 200 MHz): δ 8.05–8.0(d, J = 7.81Hz, 1H), 7.32–7.14(m, 5H), 5.15(s, 2H), 3.11(s, 3H), 2.68(s, 3H), 2.4(s, 3H), 2.3(s, 3H). |
| 14 | H₃CS-, H₃CO-, phenyl substituted diaryl furanone | 10.0 & 91.52 | 142–144 | (CDCl$_3$, 200 MHz): δ 7.4 (s, 5H), 7.25–7.00(m, 2H), 6.85–6.75(d, J = 7.83Hz, 1H), 5.19(s, 2H), 3.9(s, 3H), 1.99(s, 3H). |
| 15 | H₃CO₂S-, H₃C-, isobutyl substituted diaryl furanone | 55 & 90 | 168–170 | (CDCl$_3$, 200 MHz): δ 8.02–7.98(d, J = 8.2Hz, 1H), 7.33–7.16(m, 6H), 5.15(s, 2H), 3.09(s, 3H), 2.63(s, 3H), 2.52–2.48(d, J = 7.15Hz, 2H), 2.0–1.8(m, 1H), 0.93–0.9(d, J = 6.64Hz, 6H). |
| 16 | H₃CS-, H₃C-, F₃C- substituted diaryl furanone | 68 & 98 | 140–143 | (CDCl$_3$, 200 MHz): δ 7.63–7.6(m, 4H), 7.09–7.03(t, J = 3.73Hz, 3H), 5.19(s, 2H), 2.48(s, 3H), 2.25(s, 3H). |

-continued

Examples 2–93 have been prepared by similar procedures described in Example 1.

| Example No. | Structure | Yield (%) & Purity (%) | Melting Point (° C.) | ¹HNMR Data |
|---|---|---|---|---|
| 17 | 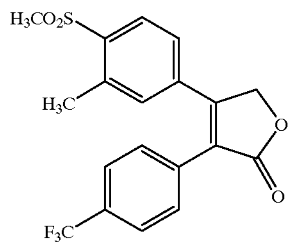 | 74 & 95 | 160–163 | (CDCl$_3$, 200 MHz): δ 8.10–8.0(d, J = 7.89Hz, 1H), 7.69–7.63(d, J = 8.3Hz, 3H), 7.56–7.51(d, J = 8.3Hz, 3H), 5.19(s, 2H), 3.1(s, 3H), 2.66(s, 3H). |
| 18 | 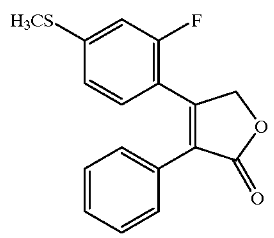 | 53 & 99.7 | 145–147 | (CDCl$_3$, 200 MHz): δ 7.39 (s, 5H), 7.26–6.84(m, 3H), 5.20(s, 2H), 2.48(s, 3H). |
| 19 | 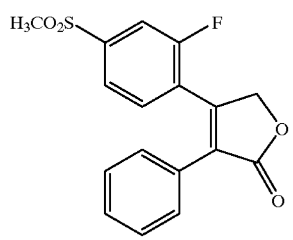 | 53 & 95 | 140 | (CDCl$_3$, 200 MHz): δ 7.75 (d, J = 9.46Hz, 1H), 7.66 (d, J = 8.08Hz, 1H), 7.38(s, 6H), 5.22(s, 2H), 3.09(s, 3H). |
| 20 | 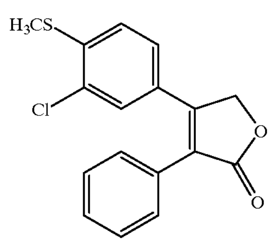 | 35.05 & 97.74 | 151–152 | (CDCl$_3$, 200 MHz): δ 7.4 (s, 5H), 7.27–7.07(m, 3H), 5.14(s, 2H), 2.47(s, 3H). |
| 21 | 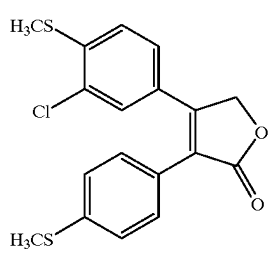 | 32.7 & 96.75 | 157–158 | (CDCl$_3$, 200 MHz): δ 7.38–7.20(m, 6H), 7.06(d, J = 8.3Hz, 1H), 5.11(s, 2H), 2.50(s, 3H), 2.47(s, 3H). |

Examples 2–93 have been prepared by similar procedures described in Example 1.

| Example No. | Structure | Yield (%) & Purity (%) | Melting Point (° C.) | ¹HNMR Data |
|---|---|---|---|---|
| 22 | 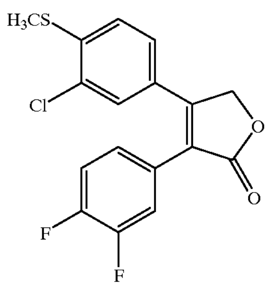 | 28.3 & 95.97 | 151–152 | (CDCl$_3$, 200 MHz): δ 7.27–7.11(m, 6H), 5.13(s, 2H), 2.48(s, 3H). |
| 23 | 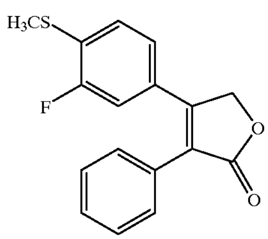 | 34 & 99.18 | 145–146 | (CDCl$_3$, 200 MHz): δ 7.4 (s, 5H), 7.25–6.93(m, 3H), 5.13(s, 2H), 2.46(s, 3H). |
| 24 | 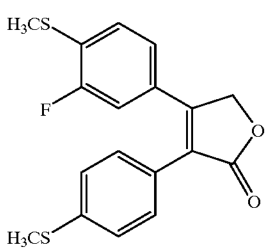 | 36 & 97.81 | 161–162 | (CDCl$_3$, 200 MHz): δ 7.37–7.11(m, 7H), 5.11(s, 2H), 2.49(s, 3H), 2.47(s, 3H). |
| 25 | 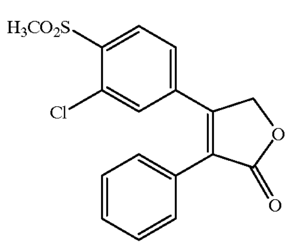 | 25 & 89.09 | 154–155 | (CDCl$_3$, 200 MHz): δ 8.10–8.00(d, J = 8.20Hz, 1H), 7.55–7.25(m, 7H), 5.16(s, 2H), 3.27(s, 3H). |
| 26 | 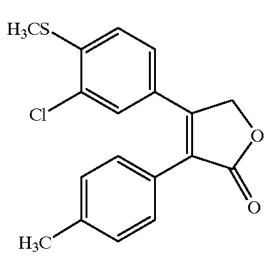 | 35 & 98.21 | 147–149 | (CDCl$_3$, 200 MHz): δ 7.34–7.19(m, 6H), 7.06(d, J = 8.4Hz, 1H), 5.12(s, 2H), 2.48(s, 3H), 2.39(s, 3H). |

-continued

Examples 2–93 have been prepared by similar procedures described in Example 1.

| Example No. | Structure | Yield (%) & Purity (%) | Melting Point (° C.) | ¹HNMR Data |
|---|---|---|---|---|
| 27 | H₃CS—(3-F-phenyl)—C=C(4-methylphenyl)—CH₂—O—C=O (furanone) | 36 & 98.40 | 159–160 | (CDCl₃, 200 MHz): δ 7.33–7.12(m, 7H), 5.12(s, 2H), 2.48(s, 3H), 2.39(s, 3H). |
| 28 | H₃CO₂S—(3-F-phenyl)—C=C(phenyl)—CH₂—O—C=O (furanone) | 36.5 & 95.58 | 155–156 | (CDCl₃, 200 MHz): δ 8.0–7.95(t, J = 7.47Hz, 1H), 7.4–7.2(m, 7H), 5.17(s, 2H), 3.24(s, 3H). |
| 29 | H₃CO₂S—(3-Cl-phenyl)—C=C(4-methylphenyl)—CH₂—O—C=O (furanone) | 20 & 93.94 | 164–166 | (CDCl₃, 200 MHz): δ 8.12 (d, J = 8.30Hz, 1H), 7.43–7.20(m, 6H), 5.16(s, 2H), 3.29(s, 3H), 2.40(s, 3H). |
| 30 | H₃CO₂S—(3-F-phenyl)—C=C(4-methylphenyl)—CH₂—O—C=O (furanone) | 20.6 & 89.93 | 161–163 | (CDCl₃, 200 MHz): δ 8.0–7.90(t, J = 7.5Hz, 1H), 7.3–7.1(m, 6H), 5.16(s, 2H), 3.25(s, 3H), 2.40(s, 3H). |
| 31 | H₃CS—(2-F-phenyl)—C=C(4-CF₃-phenyl)—CH₂—O—C=O (furanone) | 60 & 98.4 | Low melting | (CDCl₃, 200 MHz): δ 7.66–7.54(m, 4H), 7.27–6.90(m, 3H), 5.23(s, 2H), 2.50(s, 3H). |

-continued

Examples 2–93 have been prepared by similar procedures described in Example 1.

| Example No. | Structure | Yield (%) & Purity (%) | Melting Point (° C.) | ¹HNMR Data |
|---|---|---|---|---|
| 32 | H₃CO₂S–(2-F-phenyl)–furanone–(4-CF₃-phenyl) | 44 & 89 | 88 | (CDCl₃, 200 MHz): δ 7.83–7.39(m, 7H), 5.27(s, 2H), 3.13(s, 3H). |
| 33 | H₃CO₂S–(3-CH₃-phenyl)–furanone–(4-SCH₃-phenyl) | 52 & 97 | 100–103 | (CDCl₃, 200 MHz): δ 8.05–8.0(d, J = 7.80Hz, 1H), 7.33–7.12(m, 6H), 5.13(s, 2H), 3.09(s, 3H), 2.66(s, 3H), 2.49(s, 3H). |
| 34 | H₃CO₂S–(2-F-phenyl)–furanone–(4-CH₃-phenyl) | 27 & 98 | 78–80 | (CDCl₃, 200 MHz): δ 7.70 (m, 2H), 7.47(m, 1H), 7.17 (m, 4H), 5.20(s, 2H), 3.1 (s, 3H), 2.37(s, 3H). |
| 35 | H₃CS–(2-F-phenyl)–furanone–(4-iBu-phenyl) | 52 & 96.5 | 92–94 | (CDCl₃, 200 MHz): δ 7.36 (d, J = 7.98Hz, 2H), 7.16 (d, J = 8.07Hz, 2H), 7.09–6.85(m, 3H), 5.2(s, 2H), 2.51–2.46(d, J = 9.00Hz, 2H), 2.45(s, 3H), 1.9(m, 1H), 0.95–0.91(d, J = 7.00 Hz, 6H). |
| 36 | H₃CO₂S–(2-F-phenyl)–furanone–(4-iBu-phenyl) | 68 & 96 | 164–166 | (CDCl₃, 200 MHz): δ 7.76 (d, J = 9.32Hz, 1H), 7.66 (d, J = 7.98Hz, 1H), 7.45(t, J = 7.06, 1H), 7.30(d, J = 8.21Hz, 2H), 7.15(d, J = 7.89Hz, 2H), 5.2(s, 2H), 3.11(s, 3H), 2.52–2.49(d, J = 7.29Hz, 2H), 1.85(m, 1H), 0.92–0.89(d, J = 8.10 Hz, 6H). |

-continued

Examples 2–93 have been prepared by similar procedures described in Example 1.

| Example No. | Structure | Yield (%) & Purity (%) | Melting Point (° C.) | ¹HNMR Data |
|---|---|---|---|---|
| 37 | H₃CO₂S, H₃C, H₃CO (structure) | 53 & 92.0 | 110–112 | (CDCl₃, 200 MHz): δ 8.09–8.0(d, J = 7.85Hz, 1H), 7.38–7.3(t, J = 8.4Hz, 4H), 6.92–6.88(d, J = 8.7Hz, 2H), 5.12(s, 2H), 3.83(s, 3H), 3.09(s, 3H), 2.65(s, 3H). |
| 38 | H₃CS, F, H₃CO (structure) | 30 & 97.84 | 122–124 | (CDCl₃, 200 MHz): δ 7.40–7.35(d, J = 8.8Hz, 2H), 7.25(s, 1H), 7.13–6.9(m, 4H), 5.10(s, 2H), 3.83(s, 3H), 2.47(s, 3H). |
| 39 | H₃CO₂S, F, H₃CO (structure) | 20 & 91.8 | 154–156 | (CDCl₃, 200 MHz): δ 8.0–7.95(t, J = 7.90Hz, 1H), 7.3(m, 4H), 6.92(d, J = 8.70Hz, 2H), 5.12(s, 3H), 3.92(s, 3H), 3.23(s, 3H). |
| 40 | H₃CO₂S, Cl, H₃CO (structure) | 22 & 90.3 | Low melting | (CDCl₃, 200 MHz): δ 7.85–7.80(d, J = 8.00Hz, 1H), 7.45–7.20(m, 5H), 6.80(d, J = 8.4Hz, 1H), 5.09(s, 2H), 3.78(s, 3H), 3.10(s, 3H). |
| 41 | H₃CO₂S, F, H₃C, H₃CS (structure) | 50 & 89.35 | 144 | (CDCl₃, 200 MHz): δ 7.77 (d, J = 9.55Hz, 1H), 7.68 (d, J = 7.97Hz, 1H), 7.48(t, J = 6.64Hz, 1H), 7.26(d, J = 6.64Hz, 1H), 7.12(d, J = 4.98Hz, 2H), 5.20(s, 2H), 3.10(s, 3H), 2.48(s, 3H), 2.28(s, 3H). |

-continued

Examples 2–93 have been prepared by similar procedures described in Example 1.

| Example No. | Structure | Yield (%) & Purity (%) | Melting Point (° C.) | $^1$HNMR Data |
|---|---|---|---|---|
| 42 | 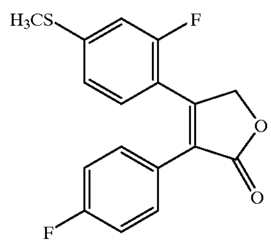 | 56 & 96 | 118 | (CDCl$_3$, 200 MHz): δ 7.45–7.38(m, 2H), 7.25–6.87(m, 5H), 5.17(s, 2H), 2.48(s, 3H). |
| 43 | 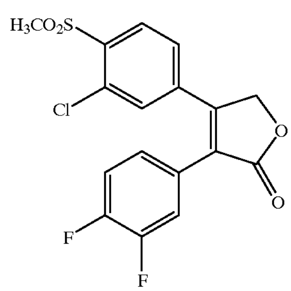 | 30.6 & 90.0 | Low melting | (CDCl$_3$, 200 MHz): δ 8.20–8.10(d, J = 8.3Hz 1H), 7.98–7.96(d, J = 8.3Hz, 2H), 7.6–7.3(m, 3H), 5.21 (s, 2H), 3.28(s, 3H). |
| 44 | 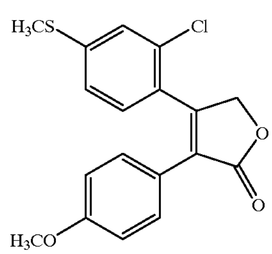 | 23 & 91.0 | Low melting | (CDCl$_3$, 200 MHz): δ 7.40–7.35(d, J = 8.6Hz, 1H), 7.25–7.0(m, 4H), 6.85–6.75(d, J = 7.5Hz, 2H), 5.07(s, 2H), 3.77(s, 3H), 2.49(s, 3H). |
| 45 | 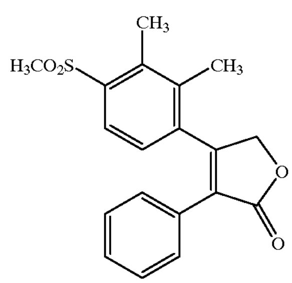 | 46 & 96.79 | 175–177 | (CDCl$_3$, 200 MHz): δ 8.06–8.02(d, J = 8.30Hz, 1H), 7.3–7.2(m, 6H), 4.99(s, 2H), 3.13(s, 3H), 2.64(s, 3H), 2.04(s, 3H). |
| 46 | 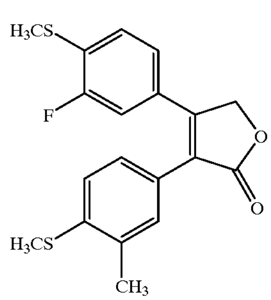 | 40 & 96.0 | 176–178 | (CDCl$_3$, 200 MHz): δ 7.30–6.90(m, 6H), 5.07(s, 2H), 2.56(s, 6H), 2.49(s, 3H). |

-continued

Examples 2–93 have been prepared by similar procedures described in Example 1.

| Example No. | Structure | Yield (%) & Purity (%) | Melting Point (° C.) | ¹HNMR Data |
|---|---|---|---|---|
| 47 | (structure with H₃CO₂S, F, H₃CO₂S, CH₃ substituents on furanone) | 34 & 92.0 | 100–102 | (CDCl$_3$, 200 MHz): δ 8.25–8.15(m, 2H), 7.60(s, 1H), 7.45–7.25(m, 3H), 5.38(s, 2H), 3.42(s, 3H), 3.28(s, 3H), 2.90(s, 3H). |
| 48 | (structure with H₃CO₂S, H₃C, F, H₃C substituents on furanone) | 74 & 98.0 | 130–132 | (CDCl$_3$, 200 MHz): δ 8.03–7.99(d, J = 7.8Hz, J = 7.85 Hz, 1H), 7.28(s, 3H), 7.04–6.99(m, 2H), 5.15(s, 2H), 3.10(s, 3H), 2.66(s, 3H), 2.27(s, 3H). |
| 49 | (structure with H₃CO₂S, H₃C, ethyl substituents on furanone) | 60 & 88.0 | 120–122 | (CDCl$_3$, 200 MHz): δ 8.01–7.95(m, 1H), 7.34–7.23(m, 6H), 5.15(s, 2H), 3.09(s, 3H), 2.69–2.66(m, 2H), 2.65(s, 3H), 1.29–1.21(t, J = 7.3Hz, 3H). |
| 50 | (structure with H₃CO₂S, H₃C, dimethyl substituents on furanone) | 75 & 93.0 | 134–136 | (CDCl$_3$, 200 MHz): δ 8.0–7.95(d, J = 7.81Hz, 1H), 7.30–7.07(m, 5H), 5.15(s, 2H), 3.09(s, 3H), 2.66(s, 3H), 2.28(s, 3H), 2.25(s, 3H). |
| 51 | (structure with H₃CO₂S, H₃C, Br, H₃CO substituents on furanone) | 52 & 97.0 | 175–178 | (CDCl$_3$, 200 MHz): δ 8.05–8.01(d, J = 8.05Hz, 1H), 7.35–7.26(m, 3H), 6.92–6.88(d, J = 8.54Hz, 2H), 5.12(s, 2H), 3.93(s, 3H), 3.11(s, 3H), 2.68(s, 3H). |

-continued

Examples 2–93 have been prepared by similar procedures described in Example 1.

| Example No. | Structure | Yield (%) & Purity (%) | Melting Point (° C.) | ¹HNMR Data |
|---|---|---|---|---|
| 52 | H₃CO₂S–[2-F-phenyl]–[furanone]–[3-F-phenyl] | 84 & 98.4 | 125–128 | (CDCl₃, 200 MHz): δ 7.79–7.67(m, 2H), 7.46–7.11(m, 5H), 5.21(s, 2H), 3.11(s,3H). |
| 53 | H₃CO₂S–[3-F-phenyl]–[furanone]–[3-CH₃,4-SCH₃-phenyl] | 71 & 98.0 | 177–180 | (CDCl₃, 200 MHz): δ 8.01–7.95(m, 1H), 7.32–7.20(m, 5H), 5.14(s, 2H), 3.24(s, 3H), 2.49(s, 3H), 2.31(s, 3H). |
| 54 | H₃CO₂S–[2-F-phenyl]–[furanone]–[Naphthyl-1] | 35 & 90.0 | 145–148 | (CDCl₃, 200 MHz): δ 7.96–7.88(t, J = 8.3Hz, 2H), 7.71–7.13(m, 8H), 5.47(s, 2H), 3.07(s, 3H). |
| 55 | H₃CO₂S–[3-CH₃-phenyl]–[furanone]–[3-CH₃,4-OCH₃-phenyl] | 70 & 98 | 147–150 | (CDCl₃, 200 MHz): δ 7.26 (s, 6H), 5.13(s, 2H), 3.85 (s, 3H), 3.09(s, 3H), 2.66 (s, 3H), 2.19(s, 3H). |
| 56 | H₃CO₂S–[3-F-phenyl]–[furanone]–[4-F-phenyl] | 60 & 95 | 148–150 | (CDCl₃, 200 MHz): δ 8.02–7.95(t, J = 7.5Hz, 1H), 7.44–7.08(m, 6H), 5.16(s, 2H), 3.25(s, 3H). |
| 57 | H₃CO₂S–[3-F-phenyl]–[furanone]–[3-CH₃,4-OCH₃-phenyl] | 68 & 97 | 142–144 | (CDCl₃, 200 MHz): δ 7.25–7.21(m, 6H), 5.13(s, 2H), 3.86(s, 3H), 3.24(s, 3H), 2.20(s, 3H). |

-continued

Examples 2–93 have been prepared by similar procedures described in Example 1.

| Example No. | Structure | Yield (%) & Purity (%) | Melting Point (° C.) | ¹HNMR Data |
|---|---|---|---|---|
| 58 | H₃CO₂S–[phenyl-F]–[furanone]–[phenyl(H₃C, H₃CO)] | 42 & 97 | 144–146 | (CDCl₃, 200 MHz): δ 7.77–7.63(m, 2H), 7.51–7.47(d, J = 6.84Hz, 1H), 7.20–7.18 (m, 2H), 6.79–6.75(d, J = 8.5Hz, 1H), 5.17(s, 2H), 3.83(s, 3H), 3.09(s, 3H), 2.16(s, 3H). |
| 59 | H₃CO₂S–[phenyl-F]–[dimethylfuranone]–[phenyl-F] | 71 & 97 | 163–166 | (CDCl₃, 200 MHz): δ 7.86–7.76(m, 2H), 7.48–7.44(t, J = 6.83Hz, 1H), 7.09–7.06 (m, 4H), 3.14(s, 3H), 1.6 (s, 3H), 1.56(s, 3H). |
| 60 | H₃CO₂S–[phenyl-F]–[dimethylfuranone]–[phenyl-F] | 63 & 98 | 166–169 | (CDCl₃, 200 MHz): δ 7.82–7.79(m, 2H), 7.44–7.31(m, 3H), 7.02–6.98(t, J = 8.79 Hz, 2H), 3.14(s, 3H), 1.59 (s, 3H), 1.56(s, 3H). |
| 61 | H₃CO₂S–[phenyl-F]–[dimethylfuranone]–[phenyl(H₃CO, CH₃)] | 81 & 98 | 178–180 | (CDCl₃, 200 MHz): δ 7.80–7.78(m, 2H), 7.50–7.40(m, 1H), 7.2–7.02(m, 2H), 6.70–6.66(d, J = 8.3Hz, 1H), 3.78(s, 3H), 3.13(s, 3H), 2.10(s, 3H), 1.57(s, 3H), 1.55(s, 3H). |
| 62 | H₃CO₂S–[phenyl(H₃C)]–[dimethylfuranone]–[phenyl-F] | 71 & 99 | 144–148 | (CDCl₃, 200 MHz): δ 8.12–8.08(d, J = 8.3Hz, 1H), 7.38–7.31(m, 3H), 7.17–6.91(m, 3H), 3.13(s, 3H), 2.71(s, 3H), 1.6(s, 3H), 1.57(s, 3H). |

-continued

Examples 2–93 have been prepared by similar procedures described in Example 1.

| Example No. | Structure | Yield (%) & Purity (%) | Melting Point (° C.) | ¹HNMR Data |
|---|---|---|---|---|
| 63 | (H₃CO₂S-phenyl with H₂CBr substituent, furanone with methyl groups, 4-fluorophenyl) | 74 & 94 | 114–117 | (CDCl₃, 200 MHz): δ 8.16–8.12(d, J = 7.8Hz, 1H), 7.44–7.32(m, 4H), 7.03–6.99(m, 2H), 5.03(s, 2H), 3.31(s, 3H), 1.64(s, 3H), 1.54(s, 3H). |
| 64 | (Saccharin-NH-CH₂ linked to H₃CO₂S-phenyl, furanone, 4-fluorophenyl) | 65 & 98 | 178–181 | (CDCl₃, 200 MHz): δ 8.16–8.12(d, J = 7.81Hz, 1H), 8.05–7.91(m, 3H), 7.51(s, 1H), 7.43–7.39(d, J = 8.3 Hz, 1H), 7.26–7.17(m, 3H), 6.78–6.69(t, J = 8.79Hz, 2H), 5.38(s, 2H), 3.36(s, 3H), 1.57(s, 3H), 1.55(s, 3H). |
| 65 | (H₃CO₂S, F-phenyl; H₃CO₂S, CH₃-phenyl; dimethyl furanone) | 80 & 94 | 190–192 | (CDCl₃, 200 MHz): δ 7.91–7.75(m, 3H), 7.45–7.39(m, 2H), 7.18–7.13(d, J = 8.82 Hz, 1H), 3.14(s, 3H), 3.05(s, 3H), 2.64(s, 3H), 1.60(s, 3H), 1.56(s, 3H). |
| 66 | (H₃CO₂S, F-phenyl; 3-fluorophenyl; ethyl furanone) | 91 & 96 | 160–162 | (CDCl₃, 200 MHz): δ 7.99–7.93(t, J = 7.34Hz, 1H), 7.23–7.09(m, 6H), 5.44–5.40(m, 1H), 3.26(s, 3H), 2.01–1.85(m, 1H), 1.59–1.53(m, 1H), 0.99–0.92(t, J = 7.33Hz, 3H). |
| 67 | (H₃CO₂S-phenyl with morpholinomethyl-NH substituent, dimethyl furanone, 4-fluorophenyl) | 50 & 97 | 127–130 | (CDCl₃, 200 MHz): δ 8.18–8.14(d, J = 8.3Hz, 1H), 7.44–7.40(d, J = 8.3Hz, 1H), 7.39–7.23(m, 2H), 7.17(s, 1H), 6.96–6.87(m, 2H), 3.84(s, 2H), 3.57–3.55(m, 4H), 3.41(s, 3H), 2.32–2.30(m, 4H), 1.59(s, 3H), 1.54(s, 3H). |

-continued

Examples 2–93 have been prepared by similar procedures described in Example 1.

| Example No. | Structure | Yield (%) & Purity (%) | Melting Point (° C.) | $^1$HNMR Data |
|---|---|---|---|---|
| 68 | 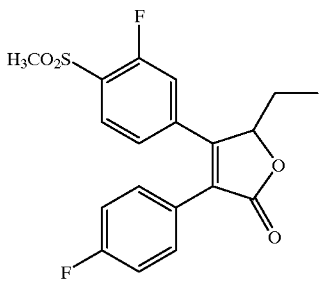 | 86 & 95 | 176–178 | (CDCl$_3$, 200 MHz): δ 8.01–7.94(t, J = 7.81Hz, 1H)), 7.38–7.01(m, 6H), 5.44–5.39(m, 1H), 3.25(s, 3H), 2.0–1.8(m, 1H), 1.60–1.53 (m, 1H), 0.97–0.90(t, J = 7.33Hz, 3H). |
| 69 | 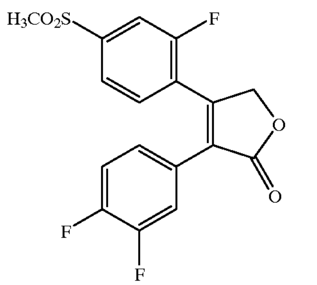 | 80 & 99 | 146–148 | (CDCl$_3$, 200 MHz): δ 7.82–7.73(m, 2H), 7.49–7.33(m, 2H), 7.16–7.13(d, J = 5.86 Hz, 2H), 5.21(s, 2H), 3.13 (s, 3H). |
| 70 | 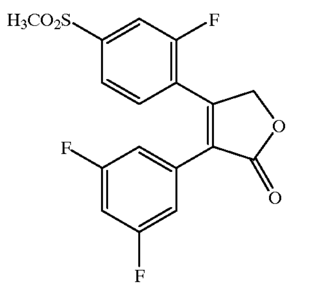 | 68 & 99 | 125–127 | (CDCl$_3$, 200 MHz): δ 7.83–7.75(m, 2H), 7.49–7.42(m, 1H), 6.97–6.87(m, 3H), 5.23(s, 2H), 3.14(s, 3H). |
| 71 | 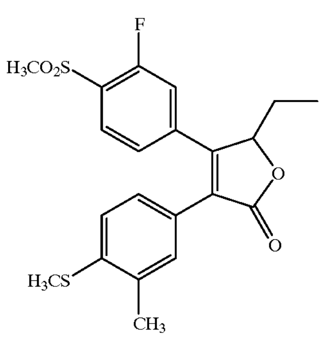 | 41 & 94 | 148–150 | (CDCl$_3$, 200 MHz): δ 7.97–7.93(t, J = 7.32Hz, 1H), 7.26–7.07(m, 5H), 5.43–5.38(m, 1H), 3.26(s, 3H), 2.47(s, 3H), 2.28(s, 3H), 2.0–1.8(m, 1H), 1.56–1.51 (m, 1H), 0.98–0.9 1(t, J = 7.32Hz, 3H). |
| 72 | 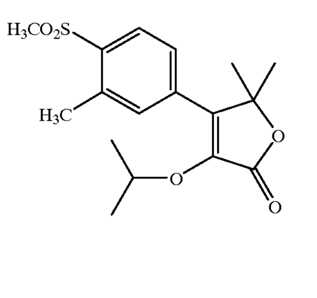 | 75 & 98 | 84–88 | (CDCl$_3$, 200 MHz): δ 8.11–8.06(d, J = 8.3Hz, 1H), 7.65 (s, 1H), 7.62–7.58(d, J = 8.34Hz, 1H), 5.23–5.15 (m, 1H), 3.12(s, 3H), 2.75 (s, 3H), 1.64(s, 3H), 1.58 (s, 3H), 1.29–1.26(d, J = 6.34Hz, 6H). |

-continued

Examples 2–93 have been prepared by similar procedures described in Example 1.

| Example No. | Structure | Yield (%) & Purity (%) | Melting Point (° C.) | ¹HNMR Data |
|---|---|---|---|---|
| 73 | 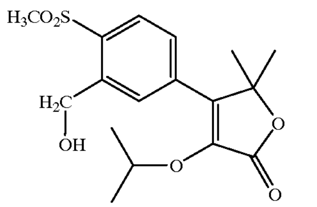 | 59 & 98 | — | (CDCl$_3$, 200 MHz): δ 8.13–8.09(d, J = 8.3Hz, 1H), 7.95(s, 1H), 7.84–7.75(d, J = 8.3Hz, 1H), 5.3–5.2(m, 1H), 5.03–5.0(d, J = 5.6Hz, 2H), 3.22(s, 3H), 1.69(s, 3H), 1.58(s, 3H), 1.33–1.30(d, J = 6.35Hz, 6H). |
| 74 | 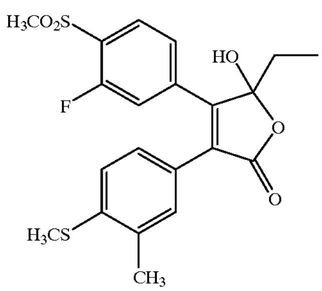 | 63 & 94.44 | 166–168 | (CDCl$_3$, 200 MHz): δ 7.97–7.93(t, J = 7.32Hz, 1H), 7.60–7.07(m, 5H), 3.85(bs, 1H), 3.26(s, 3H), 2.47(s, 3H), 2.28(s, 3H), 2.20–2.00(m, 1H), 1.96–1.75(m, 1H), 0.98–0.91(t, J = 7.32Hz, 3H). |
| 75 | 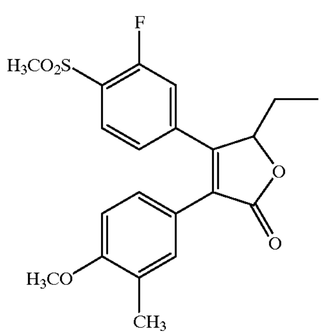 | 58 & 96 | 148–150 | (CDCl$_3$, 200 MHz): δ 7.97–7.89(t, J = 7.82Hz, 1H), 7.23–7.04(m, 4H), 6.76–6.72(d, J = 8.79Hz, 1H), 5.39–5.34(m, 1H), 3.8(s, 3H), 3.23(s, 3H), 2.14(s, 3H), 2.0–1.8(m, 1H), 1.54–1.50(m, 1H), 0.95–0.87(t, J = 7.33Hz, 3H). |
| 76 | 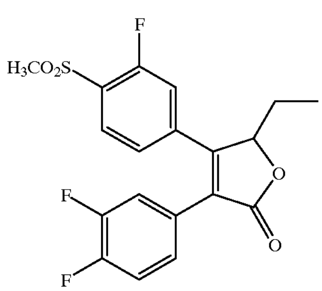 | 64 & 95 | 160–162 | (CDCl$_3$, 200 MHz): δ 8.06–7.98(t, J = 7.81Hz, 1H), 7.28–7.10(m, 5H), 5.44–5.39(m, 1H), 3.28(s, 3H), 2.01–1.87(m, 1H), 1.58–1.52(m, 1H), 0.99–0.91(t, J = 7.32Hz, 3H). |
| 77 | 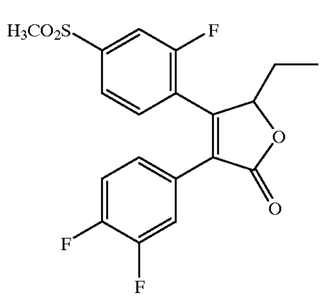 | 66 & 98 | 50–52 | (CDCl$_3$, 200 MHz): δ 7.8–7.74(m, 2H), 7.41–7.08(m, 4H), 5.49(m, 1H), 3.13(s, 3H), 1.94–1.85(m, 1H), 1.56–1.44(m, 1H), 0.99–0.93(t, J = 7.32Hz, 3H). |

-continued

Examples 2–93 have been prepared by similar procedures described in Example 1.

| Example No. | Structure | Yield (%) & Purity (%) | Melting Point (° C.) | ¹HNMR Data |
|---|---|---|---|---|
| 78 | 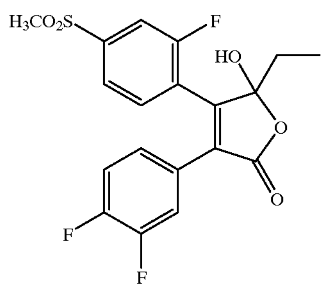 | 43 & 96.47 | 60–62 | (CDCl$_3$, 200 MHz): δ 8.00–7.62(m, 3H), 7.30–7.00(m, 3H), 4.62(bs, 1H), 3.14(s, 3H), 2.20–2.00(m, 1H), 1.95–85(m, 1H), 0.99–0.91 (t, J = 7.35Hz, 3H). |
| 79 | 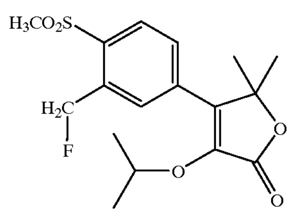 | 72 & 97 | 96–100 | (CDCl$_3$, 200 MHz): δ 8.14–8.10(d, J = 8.3Hz, 1H), 8.04(s, 1H), 7.86–7.82(d, J = 8.3Hz, 1H), 6.0–5.76 (d, J = 46.9Hz, 2H), 5.4–5.3 (m, 1H), 3.15(s, 3H), 1.68 (s, 3H), 1.56(s, 3H), 1.33–1.29(d, J = 6.35Hz, 6H). |
| 80 | 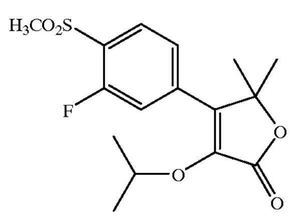 | 93 & 95.11 | 126–128 | (CDCl$_3$, 200 MHz): δ 8.10–8.00(t, J = 7.8Hz, 1H), 7.80–7.70(d, J = 11.7Hz, 1H), 7.60–7.55(d, J = 8.3 Hz, 1H), 5.55–5.40(m, 1H), 3.26(s, 3H), 1.68(s, 6H), 1.34–1.30(d, J = 6.34Hz, 6H). |
| 81 | 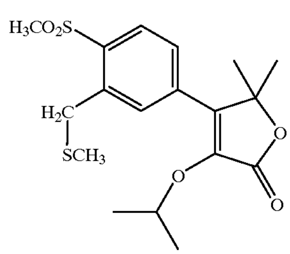 | 54 & 97 | 72–74 | (CDCl$_3$, 200 MHz): δ 8.16–8.12(d, J = 8.3Hz, 1H), 7.88(s, 1H), 7.73–7.69(d, J = 7.8Hz, 1H), 5.38–5.32 (m, 1H), 4.28(s, 2H), 3.3 (s, 3H), 2.17(s, 3H), 1.69 (s, 3H), 1.58(s, 3H), 1.33–1.30(d, J = 5.86Hz, 6H). |
| 82 | 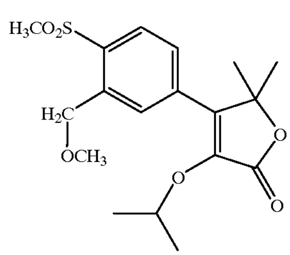 | 57 & 94 | 82–85 | (CDCl$_3$, 200 MHz): δ 8.13–8.09(d, J = 8.8Hz, 1H), 7.97(s, 1H), 7.78–7.74(d, J = 8.8Hz, 1H), 5.31–5.25 (m, 1H), 4.88(s, 2H), 3.52 (s, 3H), 3.18(s, 3H), 1.67 (s, 3H), 1.56(s, 3H), 1.31–1.28(d, J = 6.35Hz, 6H). |
| 83 | 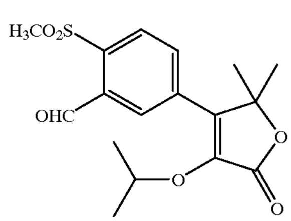 | 79 & 95 | 146–150 | (CDCl$_3$, 200 MHz): δ 10.8 (s, 1H), 8.43(s, 1H), 8.23–8.11(m, 2H), 5.48–5.41(m, 1H), 3.29(s, 3H), 1.67(s, 3H), 1.56(s, 3H), 1.35–1.32(d, J = 5.86Hz, 6H). |

-continued

Examples 2–93 have been prepared by similar procedures described in Example 1.

| Example No. | Structure | Yield (%) & Purity (%) | Melting Point (° C.) | ¹HNMR Data |
|---|---|---|---|---|
| 84 | 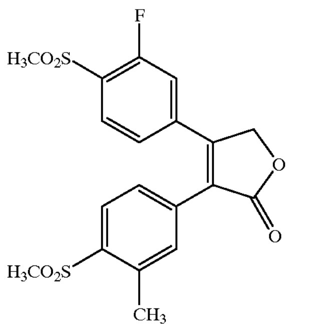 | 85 & 93 | 88–90 | (CDCl$_3$, 200 MHz): δ 8.05–7.94(m, 2H), 7.45(s, 1H), 7.27–7.24(d, J = 5.8Hz, 2H), 7.17–7.12(d, J = 10.26 Hz, 1H), 5.19(s, 2H), 3.23 (s, 3H), 3.09(s, 3H), 2.71 (s, 3H). |
| 85 | 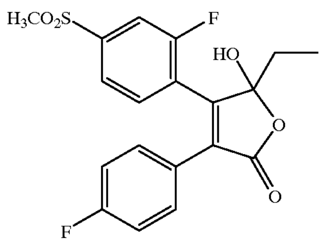 | 96 & 95 | 152–154 | (CDCl$_3$, 200 MHz): δ 7.99–7.32(m, 5H), 7.05–6.96(t, J = 8.3Hz, 2H), 3.71(s, 1H), 3.13(s, 3H), 1.97–1.83 (m, 2H), 0.99–0.92(t, J = 7.32Hz, 3H). |
| 86 | 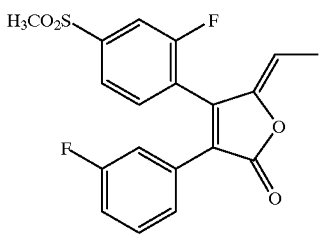 | 99 & 96 | 138–140 | (CDCl$_3$, 200 MHz): δ 7.87–7.75(m, 2H), 7.56–7.49(t, J = 7.33Hz, 1H), 7.26–7.03 (m, 4H), 5.22–5.19(m, 1H), 3.14(s, 3H), 2.05–2.02(d, J = 7.33Hz, 3H). |
| 87 | 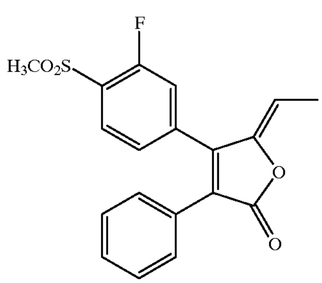 | 17 & 96 | 195–197 | (CDCl$_3$, 200 MHz): δ 8.06–7.98(t, J = 7.33Hz, 1H), 7.33–7.18(m, 7H), 5.30–5.27(m, 1H), 3.28(s, 3H), 2.05–2.02(d, J = 7.33Hz, 3H). |
| 88 | 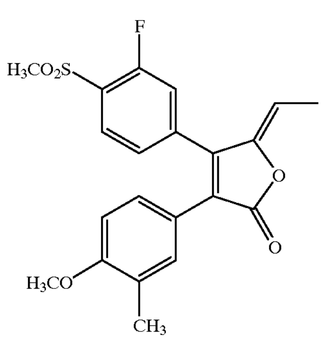 | 18 & 95 | 178–180 | (CDCl$_3$, 200 MHz): δ 8.06–7.99(t, J = 7.33Hz, 1H), 7.31–7.04(m, 4H), 6.73–6.69(d, J = 8.3Hz, 1H), 5.23–5.19(m, 1H), 3.8(s, 3H), 3.28(s, 3H), 2.14(s, 3H), 2.03–2.00(d, J = 7.32 Hz). |

-continued

Examples 2–93 have been prepared by similar procedures described in Example 1.

| Example No. | Structure | Yield (%) & Purity (%) | Melting Point (° C.) | $^1$HNMR Data |
|---|---|---|---|---|
| 89 | 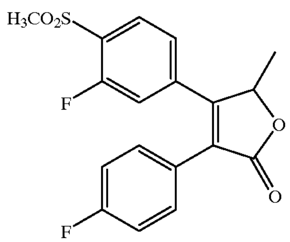 | 77 & 98 | 190–192 | (CDCl$_3$, 200 MHz): δ 8.04–7.96(t, J = 7.81Hz, 1H), 7.41–7.03(m, 6H), 5.55–5.45(m, 1H), 3.27(s, 3H), 1.47–1.44(d, J = 6.83Hz, 3H). |
| 90 | 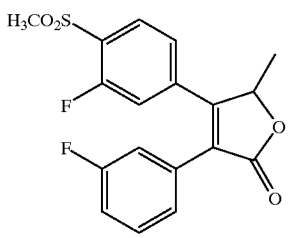 | 65 & 99 | 168–170 | (CDCl$_3$, 200 MHz): δ 8.03–7.96(t, J = 7.82Hz, 1H), 7.35–7.09(m, 6H), 5.52–5.48(m, 1H), 3.26(s, 3H), 1.47–1.43(d, J = 6.84, 3H). |
| 91 | 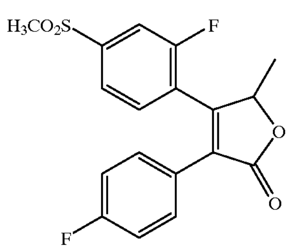 | 56 & 98 | 170–172 | (CDCl$_3$, 200 MHz): δ 7.75–7.7(m, 2H), 7.39–7.04(m, 5H), 5.65–5.53(m, 1H), 3.12(s, 3H), 1.44–1.40(d, J = 6.84Hz, 3H). |
| 92 | 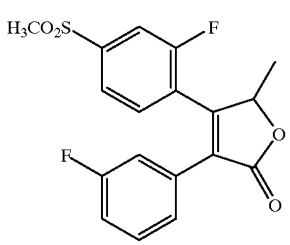 | 57 & 97 | 148–150 | (CDCl$_3$, 200 MHz): δ 7.80–7.71(m, 2H), 7.40–7.08(m, 5H), 5.62–5.58(m, 1H), 3.13(s, 3H), 1.44–1.41(d, J = 6.35Hz, 3H). |
| 93 | 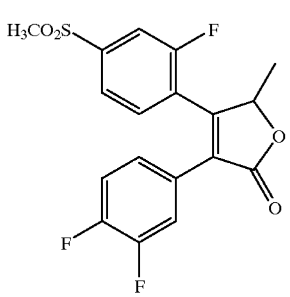 | 40 & 93 | 165–166 | (CDCl$_3$, 200 MHz): δ 7.77–7.74(m, 1H), 7.42–7.08(m, 5H), 5.64–5.55(m, 1H), 3.14(s, 3H), 1.44–1.41(d, J = 6.35Hz, 3H). |

Examples 2–93 have been prepared by similar procedures described in Example 1.

| Example No. | Structure | Yield (%) & Purity (%) | Melting Point (° C.) | ¹HNMR Data |
|---|---|---|---|---|
| 94 | H₃CO₂S-[aryl-F]–[furanone-OCH₃]–[3-fluorophenyl] | 48 & 98 | 104–106 | (CDCl₃, 200 MHz): δ 7.89–7.63(m, 3H), 7.30–7.04(m, 4H), 3.47(s, 3H), 3.12(s, 3H), 1.65(s, 3H). |
| 95 | H₃CO₂S-[aryl-F]–[furanone-CH₃]–[4-methylphenyl] | 18 & 92 | 175–177 | (CDCl₃, 200 MHz): δ 7.78–7.66(m, 2H), 7.40–7.12(m, 5H), 5.6(m, 1H), 3.12(s, 3H), 2.35(s, 3H), 1.43–1.39 (d, J = 6.35Hz, 3H). |
| 96 | H₃CO₂S-[aryl-F]–[furanone-OCH₃]–[4-fluorophenyl] | 50 & 92 | 136–138 | (CDCl₃, 200 MHz): δ 7.89–7.63(m, 3H), 7.41–6.98(m, 4H), 3.46(s, 3H), 3.12(s, 3H), 1.64(s, 3H). |

EXAMPLE 97

1-(4-Fluorophenyl)-4-(3-methylsulfonylphenyl)-3-phenyl-2, 5-dihydro-1H-2-azolone

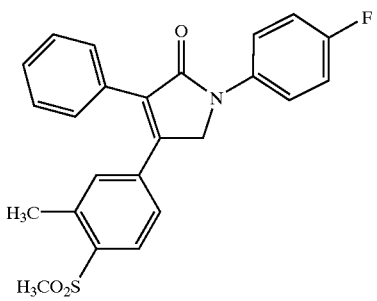

To a solution of N¹-(4-fluorophenyl)-N¹-[2-(3-methyl-4-methylsulfonylphenyl)-2-oxoethyl]-2-phenylacetamide (1 g, 2.27 mmol) in acetonitrile (15 ml was added DBU (0.346 g, 2.27 mmol) under nitrogen atmosphere at 0°–5° C. The mixture was stirred for 4 h, poured into water (50 ml) and extracted with EtOAc (3×15 ml). The organic layers were isolated, combined, dried over anhydrous Na₂SO₄ and concentrated under vacuum. The residue isolated was purified by column chromatography using EtOAc-petroleum ether (1:3) as eluent to give 0.2 g of the title compound in 21% yield. m.p. 207°–209° C.

¹H NMR (200 MHz, CDCl₃): δ 7.9–7.7 (m, 3H), 7.4–7.0 (m, 9H), 4.7 (s, 2H), 3.0 (s, 3H), 2.6 (s, 3H).

Mass (CI, i-Butane) m/z 421 (M⁺, 100).

EXAMPLE 98

3-(2-Fluoro-4-methylsulfonylphenyl)-1-(4-fluorophenyl)-4-phenyl-2,5-dihydro-1H-2,5-azoledione

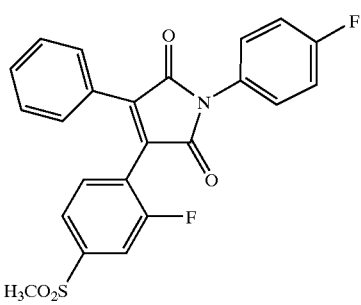

The title compound was prepared in 7% yield from N¹-(4-fluorophenyl)-N1-[2-(2-fluoro-4-methyl-sulfonylphenyl)-2-oxoethyl]-2-phenylacetamide (0.79 g, 1.58 mmol) using DBU (0.481 g, 1.58 mmol) according to the procedure described Example 2. m.p.: 198°–200° C.

$^1$H NMR (200 MHz, CDCl$_3$): δ 7.8–7.1 (m, 12H), 3.1 (s, 3H).

Mass (CI, i-Butane) m/z 439 (M$^+$, 100).

The compounds of the present invention are tested in vitro for their COX-1 and COX-2 inhibitory activity using literature assay methods. The efficacy of the compound in vivo have been tested in male Sprague-Dawley rats using rat carrageenan foot paw edema test (Proc. Soc. Exp. Biol. Med., 111, 544 (1962); Laboratory models for testing NSAIDS in non steroidal antiinflammatory drugs (J. Lombardino ed., 1985).

In Vitro Biochemical Assays

1. Spectrophotometric assay of cox-1 and cox-2:

Microsomal fraction of ram seminal vesicles used as a source of cox-1 enzyme (Hemler et al., 1976) and microsomes from sf-9 cells infected with baculo virus containing human cox-2 c-DNA used as a source of cox-2 enzyme (Wanda et al., 1994). Enzyme activity was measured using a chromogenic assay based on oxidation of N,N,N',N'-tetramethyl-p-phenylenediamine (TMPD) during the reduction of PGG$_2$ to PGH$_2$ as per described by Copeland et al., 1994 with following modifications. The assay mixture (1000 μl) contains 100 μM Tris pH 8.0, 3 μM EDTA, 15 μM hematin, 150 units enzyme and 8% DMSO. The mixture was pre-incubated at 25° C. for 15 minutes before initiation of enzyme reaction in presence of compound/vehicle. The reaction was initiated by the addition of 100 μM arachidonic acid and 120 μM TMPD. The enzyme activity is measured by estimation of the initial velocity of TMPD oxidation over the first 25 seconds of the reaction followed by increase in absorbency at 603 nM. The IC$_{50}$ values were calculated using non-linear regression analysis of percent inhibitions.

| Example No. | Conc. | Percent inhibition COX-1 | Percent inhibition COX-2 |
|---|---|---|---|
| 1 | 100 μM | 33 | 100 |
| 6 | 100 μM | 0 | 82 |
| 52 | 100 μM | 12 | 100 |
| 53 | 100 μM | 44 | 100 |
| 55 | 100 μM | 30 | 100 |
| 58 | 100 μM | 19 | 93 |
| 68 | 100 μM | 0 | 100 |
| 69 | 100 μM | 10 | 93 |
| 70 | 100 μM | 49 | 92 |
| 71 | 100 μM | 3 | 99 |
| 89 | 10 μM | 0 | 95 |

2) Human Whole Blood Assay:

COX-1 Inhibition Assay

Fresh heparinised human whole blood was incubated with lipopolysaccharide (LPS) from *E. coli* at 100 μg/ml and with 2.5 μl vehicle (D)MSO) or test compound for 24 hours at 37° C. PGE$_2$ levels in the plasma were measured using EIA kit (Cayman chemicals, USA) after deproteinization.

COX-2 Inhibition Assay

An aliquot of fresh blood was mixed either with DMSO or test compounds and was allowed to clot for 1 hour at 37° C. TXB$_2$ levels in the serum were measured using EIA kit (Cayman chemicals, USA) after deproteinization.

| Example No. | IC$_{50}$ (μM) COX-I | IC$_{50}$ (μM) COX-II |
|---|---|---|
| 1 | 194.5 ± 27.5 | 2.72 ± 0.425 |
| 6 | >500 | 5.7 |
| 52 | 1220 ± 20 | 0.578 ± 0.011 |
| 53 | 247 ± 24 | 0.368 |
| 55 | >100 | 1 |
| 58 | 357 ± 7.45 | 0.524 ± 0.062 |
| 68 | 296.5 | 1.248 |
| 69 | >500 | 0.318 ± 0.013 |
| 70 | 115 | 0.913 |
| 89 | >1000 | 6.13 |

In Vivo Screening Methods

1. Carrageenen-Induced Rat Paw Edema:

Male Wistar rats (120–140 g) were fasted for 16 h before the experiment. Compounds were suspended in 0.25% CMC and administered orally in volume of 10 ml/kg 2 h before carrageenan injection. Hind paw edema induced in rats by intradermal injection of 50 μl of 1% lambda-carrageenan in saline into the plantar surface of the right hind paw. Paw volume was measured before and 3 h after carrageenan injection by using plethysmometer (Ugo-Basile, Italy). Paw edema was compared with the vehicle control group and percent inhibition was calculated by taking the values in control group as 0%.

| Example No. | Dose | Percent inhibition |
|---|---|---|
| 6 | 30 | 23 |
| 52 | 30 | 62 |
| 53 | 30 | 39 |
| 55 | 10 | 48 |
| 58 | 30 | 44 |
| 68 | 30 | 44 |
| 69 | 30 | 51 |
| v70 | 30 | 51 |
| 71 | 30 | 17 |
| 89 | 30 | 31 |

What is claimed is:

1. A compound of formula (I),

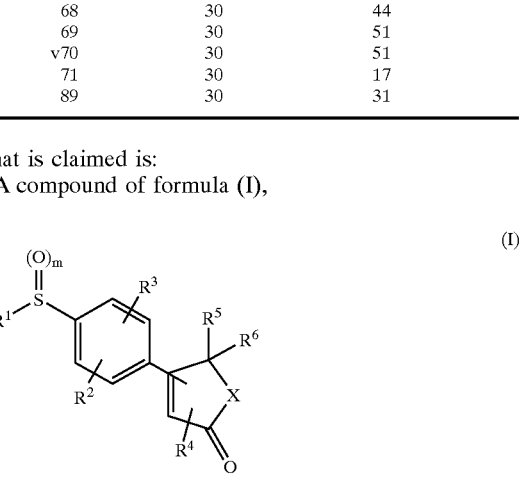

wherein R$^1$ represents amino or substituted or unsubstituted groups selected from alkyl, alkylamino, acylamino, cycloalkyl, cyclicamino, carboethoxycarbonylalkyl hydrazino, hydrazido, aminoacid residue, aryl, heteroaryl or —N=CR(NR)$_2$ where R represents hydrogen or lower alkyl group; R$^2$ represents halogen, hydroxy, cyano, nitro, azido, formyl, oximealkyl, thio or substituted or unsubstituted groups selected from amino, allyl, alkoxy, hydrazino, hydrazinoalkyl, hydrazido, hydrazidoalkyl, aminoacid residue, amino acid residue alkyl, acyl, carbonyloxyalkyl, haloalkyl, aminoalkyl, haloalkoxy, hydroxyalkyl, alkoxyalkyl, thioalkyl, alkylthio, alkylsulfinyl, alkylsulfonyl, aryl, aralkyl, aryloxy, aralkoxy, aryloxyalkyl, aralkoxyalkyl, carboxamidoalkyl carbonylaminoalkyl groups or when the groups —S(=O)$_m$—R$^1$ and R$^2$ are present on adjacent carbon atoms, R$^1$ and R$^2$ together with atoms to which they are attached also form a substituted or unsubstituted 5–7 membered cyclic structure containing carbon atoms, a sulfur atom and optionally contain one or two heteroatoms selected from O, S or N; R$^3$ represents hydrogen, halogen atom, hydroxy, nitro, cyano, azido or substituted or unsubstituted groups selected from hydrazino, hydrazinoalkyl, hydrazido, hydrazidoalkyl, aminoacid residues, alkyl, alkoxy, hydroxyalkyl, alkoxyalkyl, acylamino or amino groups; R$^4$ and R$^5$ are same or different and independently represent hydrogen, halogen, hydroxy, cyano, nitro, thio, hydroxylamino, substituted or unsubstituted groups selected from alkyl, alkoxy, acyl, acyloxy, amino, hydrazino, hydrazinoalkyl, hydrazido, hydrazidoalkyl, aminoacid residues, aminoacyl, carboxyalkyl, carboxyalkenyl, aryl, aryloxy, aralkyl, aralkoxy, alkoxycarbonyl, aryloxycarbonyl, aralkoxycarbonyl, heteroaryl, heteroaryloxy, heteroaralkyl, heteroaralkoxy, heteroarylcarbonyl heteroaryloxycarbonyl, heteroaralkylcarbonyl, heteroaralkoxycarbonyl, heterocyclylcarbonyl, aminocarbonyl, aminocarbonylalkyl, carbonylamino, cycloalkylacylamino, alkylaminoalkoxy, alkylaminoacyl, carboxylic acid or its derivatives, saturated or partially saturated or aromatic single or fused 5 to 7 membered carbocycle ring or saturated or partially saturated or aromatic, single or fused 5 to 7 membered heterocycle ring; R$^6$ represents hydrogen, halogen, hydroxy, amino, cyano, nitro, thio, hydroxylamino or unsubstituted or substituted groups selected from alkyl, alkoxy, or carboxyalkyl; R$^5$ and R$^6$ together represent =C(R$^a$)(R$^b$), where R$^a$ and R$^b$ are same or different and independently represent hydrogen, substituted or unsubstituted (C$_1$–C$_6$)alkyl or aryl; =O or =NR$^7$ where R$^7$ represents hydrogen, aryl or heteroaryl group; X represents oxygen and m is an integer in the range of 0–2, its analogs, its tautomeric forms, its stereoisomers, its regioisomers, its polymorphs, its pharmaceutically acceptable salts, or its pharmaceutically acceptable solvates.

2. A compound of formula (I) according to claim 1, wherein when R$^1$ and R$^2$ together form a cyclic structure, R$^1$ and R$^2$ together represent substituted or unsubstituted —NH—C(=O)—(CH$_2$)$_n$—, —CH2—(CH$_2$)$_n$—, —(CH$_2$)$_n$—C(=O)—, —CH$_2$—C(=O)—CH$_2$—, —NH—(CH$_2$)$_n$—, —NH—C(=O)—, —NH—(CH$_2$)$_n$—C(=O)—, —(CH$_2$)$_n$—C(=O)—NH—, —NH—(CH$_2$)$_n$—O—, —NH—(CH$_2$)$_n$—S—, —CH$_2$—(CH$_2$)$_n$—O—, —CH$_2$—(CH$_2$)$_n$—S—, where n is 1 or 2.

3. A compound of formula (I) according to claim 1, wherein when the groups represented by R$^1$ and R$^2$ are substituted, the substituents are selected from hydroxy, linear or branched (C$_1$–C$_6$)alkyl, (C$_1$–C$_6$)alkoxy, aryl, aralkyl, aralkoxy, acyl, heteroaryl, heteroaralkyl, heterocyclyl, sulfonyl, (C$_1$–C$_6$)alkylsulfinyl, arylsulfinyl, (C$_1$–C$_6$)alkylsulfonyl or arylsulfonyl.

4. The compound according to claim 3, wherein the substituents on (C$_1$–C$_6$)alkyl and aryl moieties are selected from hydroxy, halogen, nitro or amino groups.

5. A compound of formula (I) according to claim 1, wherein when the groups represented by R$^4$ and R$^5$ are substituted, the substituents are selected from halogen atom, hydroxy, cyano, nitro, optionally halogenated (C$_1$–C$_6$)alkyl, optionally halogenated (C$_1$–C$_3$)alkoxy, acyl, amino, acylamino, (C$_3$–C$_8$)cycloalkyl, (C$_3$–C$_8$)cycloalkoxy, aryl, aryloxy, aralkyl, aralkoxy, heteroaryl, heterocyclyl, heteroaryloxy, heteroaralkyl, heteroaralkoxy, heteroaryloxycarbonyl, heteroaralkoxycarbonyl, heteroaryloxycarbonylamino, heteroaralkoxycarbonylamino, acyloxy, (C$_1$–C$_6$)alkoxycarbonyl, aryloxycarbonyl, aralkoxycarbonyl, monoalkylamino, (C$_1$–C$_6$)dialkylamino, arylamino, aralkylamino, amino (C$_1$–C$_6$)alkyl, hydroxy(C$_1$–C$_6$)alkyl, (C$_1$–C$_6$)alkoxy (C$_1$–C$_6$)alkyl, aryloxy(C$_1$–C$_6$)alkyl, aralkoxy(C$_1$–C$_6$)alkyl, (C$_1$–C$_6$)alkoxycarbonylamino, aryloxycarbonylamino, aralkoxycarbonylamino, thio, thio(C$_1$–C$_6$)alkyl, (C$_1$–C$_6$) alkylthio, (C$_1$–C$_6$)alkylsulfinyl, (C$_1$–C$_6$)alkylsulfonyl, sulfonic acid or its derivatives or carboxylic acid or its derivatives.

6. A compound of formula (I) according to claim 1, wherein when the groups represented by R$^3$, R$^6$ and R$^8$ are substituted, the substituents are selected from halogen, hydroxy, nitro, thio, amino or cyano groups.

7. A process for the preparation of compound of formula (I),

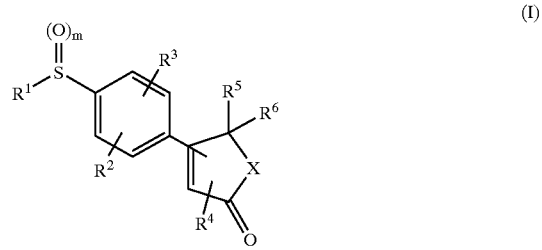

wherein R$^1$ represents amino or substituted or unsubstituted groups selected from alkyl, alkylamino, acylamino, cycloalkyl, cyclicamino, carboethoxycarbonylalkyl, hydrazino, hydrazido, aminoacid residue, aryl, heteroaryl or —N=CR(NR)$_2$ where R represents hydrogen or lower alkyl group; R$^2$ represents halogen, hydroxy, cyano, nitro, azido, formyl, oximealkyl, thio or substituted or unsubstituted groups selected from amino, alkyl, alkoxy, hydrazino, hydrazinoalkyl, hydrazido, hydrazidoalkyl, aminoacid residue, aminoacid residue alkyl, acyl, carbonyloxyalkyl, haloalkyl, aminoalkyl, haloalkoxy, hydroxyalkyl, alkoxyalkyl, thioalkyl, alkylthio, alkylsulfinyl, alkylsulfonyl, aryl, aralkyl, aryloxy, aralkoxy, aryloxyalkyl, aralkoxyalkyl, carboxamidoalkyl, carbonylaminoalkyl groups or when the groups —S(=O)$_m$—R$^1$ and R$^2$ are present on adjacent carbon atoms, R$^1$ and R$^2$ together with atoms to which they are attached also form a substituted or unsubstituted 5–7 membered cyclic structure containing carbon atoms, a sulfur atom and optionally contain one or two heteroatoms selected from O, S or N; R$^3$ represents hydrogen, halogen atom, hydroxy, nitro, cyano, azido or substituted or unsubstituted groups selected from hydrazino, hydrazinoalkyl, hydrazido, hydrazidoalkyl, aminoacid residues, alkyl, alkoxy, hydroxyalkyl, alkoxyalkyl, acylamino or amino groups; R$^4$ and R$^5$ are same or different and independently represent hydrogen, halogen, hydroxy, cyano, nitro, thio, hydroxylamino, substituted or unsubstituted groups selected from alkyl, alkoxy, acyl, acyloxy, amino, hydrazino, hydrazinoalkyl, hydrazido, hydrazidoalkyl, aminoacid residues, aminoacyl, carboxyalkyl, carboxyalkenyl, aryl, aryloxy, aralkyl, aralkoxy, alkoxycarbonyl, aryloxycarbonyl, aralkoxycarbonyl, heteroaryl, heteroaryloxy, heteroaralkyl, heteroaralkoxy, heteroarylcarbonyl, heteroaryloxycarbonyl, heteroaralkylcarbonyl, heteroaralkoxycarbonyl, heterocyclylcarbonyl, aminocarbonyl, aminocarbonylalkyl, carbonylamino, cycloalkylacylamino, alkylaminoalkoxy, alkylaminoacyl, carboxylic acid or its derivatives, saturated or partially saturated or aromatic single or fused 5 to 7 membered carbocycle ring or saturated or partially saturated or aromatic, single or fused 5 to 7 membered hetero cycle ring, $R^6$ represents hydrogen, halogen, hydroxy, amino, cyano, nitro, thio, hydroxylamino or unsubstituted or substituted groups selected from alkyl, alkoxy, or carboxyalkyl; $R^5$ and $R^6$ together represent $=C(R^a)(R^b)$ where $R^a$ and $R^b$ are same or different and independently represent hydrogen, substituted or unsubstituted ($C_1$–$C_6$)alkyl or aryl; —O or $=NR^7$, where $R^7$ represents hydrogen, aryl or heteroaryl group; X represents oxygen and m is an integer in the range of 0–2; its analogs, its tautomeric forms, its stereoisomers, its regioisomers, its polymorphs, or its pharmaceutically acceptable salts, its pharmaceutically acceptable solvates, which comprises:

(a) reacting a compound of formula (I-1)

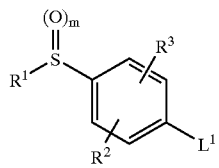

(I-1)

where $L^1$ represents $B(OR)_2$, wherein R represents hydrogen or ($C_1$–$C_6$)alkyl and all other symbols are as defined above, with a compound of formula (I-2)

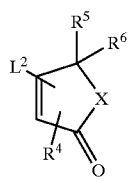

(I-2)

where $L^2$ represents halogen atom or leaving group and all other symbols are as defined above; or (b) reacting the compound of formula (I-3)

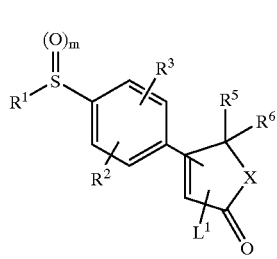

(I-3)

where all the symbols are as defined above, with a compound of formula (I-4)

$$R^4—L^2 \quad (I\text{-}4)$$

where $R^4$ and $L^2$ are as defined above; or (c) reacting the compound of formula (I-5)

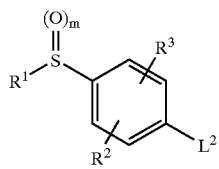

(I-5)

where all the symbols are as defined above, with a compound of formula (I-6)

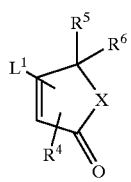

(I-6)

where $L^1$ represents $B(OR)_2$ and all other symbols are as defined above; or (d) reacting the compound of formula (I-7)

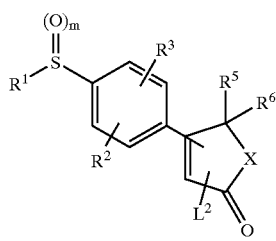

(I-7)

where $L^2$ represents halogen atom or leaving groups and all other symbols are as defined above, with a compound of formula (I-8)

$$R^4—L^1 \quad (I\text{-}8)$$

where $L^1$ represents $B(OR)_2$ and all other symbols are as defined above; or e) reacting the compound of formula (II-2)

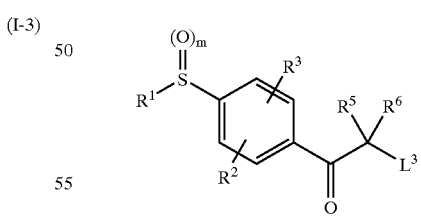

(II-2)

where $L^3$ represents halogen atom and all other symbols are as defined above, with compound of formula (II-3)

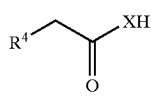

(II-3)

where $R^4$ and X are as defined above; or (f) reacting compound of formula (II-4)

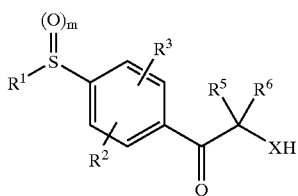

where all the symbols are as defined above, with a compound of formula (II-5)

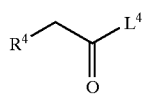

where $L^4$ represents hydroxy or halogen atom and all other symbols are as defined above; or g. transforming a compound of formula (I), where $R^1$ represents $(C_1-C_6)$ alkyl, m represents 2 and all other symbols are as defined above, to produce a compound of formula (I), where $R^1$ represents amino group and m represents 2; or h. reducing a compound of formula (I), where in represents 1 or 2 and all other symbols are as defined above, to produce a compound of formula (I), where m represents 0 and all other symbols are as defined above; or i. oxidizing a compound of formula (I), where m represents 0 and all other symbols are as defined above, to produce a compound of formula (I), where m represents 1 or 2 and all other symbols are as defined above.

8. A process for the preparation of compound of formula (I),

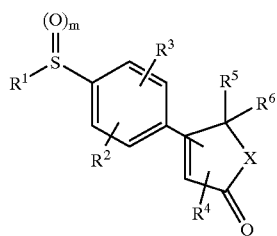

wherein $R^1$ represents amino or substituted or unsubstituted groups selected from alkyl, alkylamino, acylamino, cycloalkyl, cyclicamino, carboethoxycarbonylalkyl, hydrazino, hydrazido, aminoacid residue, aryl, heteroaryl or —N=CR(NR)$_2$ where R represents hydrogen or lower alkyl group; $R^2$ represents halogen, hydroxy, cyano, nitro, azido, formyl, oximealkyl, thio or substituted or unsubstituted groups selected from amino, allyl, alkoxy, hydrazino, hydrazinoalkyl, hydrazido, hydrazidoalkyl, aminoacid residue, aminoacid residue alkyl, acyl, carbonyloxyalkyl, haloalkyl, aminoalkyl, haloalkoxy, hydroxyalkyl, alkoxyalkyl, thioalkyl, alkylthio, alkylsulfinyl, alkylsulfonyl, aryl, aralkyl, aryloxy, aralkoxy, aryloxyalkyl, aralkoxyalkyl, carboxamidoalkyl, carbonylaminoalkyl groups or when the groups —S(=O)$_m$—R$^1$ and $R^2$ are present on adjacent carbon atoms, $R^1$ and $R^2$ together with atoms to which they are attached also form a substituted or unsubstituted 5-7 membered cyclic structure containing carbon atoms, a sulfur atom and optionally contain one or two heteroatoms selected from O, S or N, $R^3$ represents hydrogen, halogen atom, hydroxy, nitro, cyano, azido or substituted or unsubstituted groups selected from hydrazino, hydrazinoalkyl, hydrazido, hydrazidoalkyl, aminoacid residues, alkyl, alkoxy, hydroxyalkyl, alkoxyalkyl, acylamino or amino groups, $R^4$ and $R^5$ are same or different and independently represent hydrogen, halogen, hydroxy, cyano, nitro, thio, hydroxylamino, substituted or unsubstituted groups selected from alkyl, alkoxy, acyl, acyloxy, amino, hydrazino, hydrazinoalkyl, hydrazido, hydrazidoalkyl, aminoacid residues, aminoacyl, carboxyalkyl, carboxyalkenyl, aryl, aryloxy, aralkyl, aralkoxy, alkoxycarbonyl, aryloxycarbonyl, aralkoxycarbonyl, heteroaryl, heteroaryloxy, heteroaralkyl, heteroaralkoxy, heteroarylcarbonyl, heteroaryloxycarbonyl, heteroaralkylcarbonyl, heteroaralkoxycarbonyl, heterocyclylcarbonyl, aminocarbonyl, aminocarbonylalkyl, carbonylamino, cycloalkylacylamino, alkylaminoalkoxy, alkylaminoacyl, carboxylic acid or its derivatives, saturated or partially saturated or aromatic single or fused 5 to 7 membered carbocycle ring or saturated or partially saturated or aromatic, single or fused 5 to 7 membered heterocycle ring; $R^6$ represents hydrogen, halogen, hydroxy, amino, cyano, nitro, thio, hydroxylamino or unsubstituted or substituted groups selected from alkyl, alkoxy, or carboxyalkyl; $R^5$ and $R^6$ together represent =C(R$^a$R$^b$), where R$^a$ and R$^b$ are same or different and independently represent hydrogen, $(C_1-C_6)$alkyl or aryl; =O or =NR$^7$, where $R^7$ represents hydrogen, aryl or heteroaryl group; X represents oxygen and m is an integer in the range of 0–2; its analogs, its tautomeric forms, its stereoisomers, its regioisomers, its polymorphs, its pharmaceutically acceptable salts, or its pharmaceutically acceptable solvates, which comprises:

(a) reacting compound of formula (II-1)

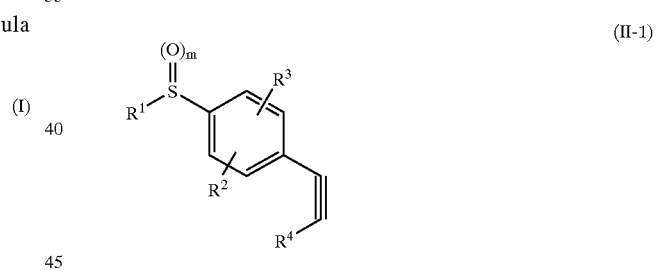

where $R^1$, $R^2$, $R^3$, $R^4$ and m are as defined above, with carbon monoxide and water; or (b) reacting compound of formula (II-1)

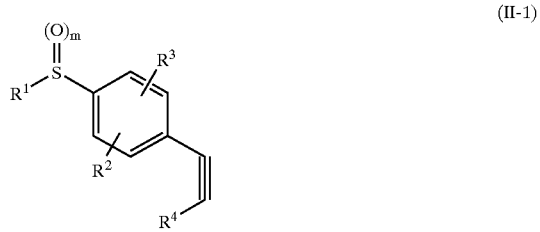

where all the symbols are as defined above, with a transition metal carbonyl complex.

9. A process as claimed in claim 8 wherein the transition metal carbonyl complex is selected from $Rh_4(CO)_{12}$ or $Rh_4(CO)_{16}$.

10. A compound as claimed in claim 1, which is selected from the group consisting of:

4-(1,1-Dioxo-2,3-dihydrobenzo[b]thiophen-5-yl)-3-(3,4-difluorophenyl)-2,5-dihydro-2-furanone;

4-(3-Methyl-4-methylsulfanylphenyl)-3-(3,4-difluorophenyl)-2,5-dihydro-2-furanone;

4-(3-Methyl-4-methylsulfonylphenyl)-3-(3,4-difluorophenyl)-2,5-dihydro-2-furanone;

4-(3-Methyl-4-methylsulfanylphenyl)-3-phenyl-2,5-dihydro-2-furanone;

4-(3-Methyl-4-methylsulfonylphenyl)-3-phenyl-2,5-dihydro-2-furanone;

4-(3-Methyl-4-methylsulfanylphenyl)-3-(4-fluorophenyl)-2,5-dihydro-2-furanone;

4-(3-Methyl-4-methylsulfanylphenyl)-3-(4-methylphenyl)-2,5-dihydro-2-furanone;

4-(3-Methyl-4-methylsulfonylphenyl)-3-(4-fluorophenyl)-2,5-dihydro-2-furanone;

4-(3-Methyl-4-methylsulfonylphenyl)-3-(4-methylphenyl)-2,5-dihydro-2-furanone;

4-(3-Methyl-4-methylsulfanylphenyl)-3-(4-isobutylphenyl)-2,5-dihydro-2-furanone;

4-(3-Methyl-4-methylsulfanylphenyl)-3-(4-methoxyphenyl)-2,5-dihydro-2-furanone;

4-(3-Methyl-4-methylsulfonylphenyl)-3-(3-methyl-4-methylsulfanylphenyl)-2,5-dihydro-2-furanone;

3-Phenyl-4-(3-methoxy-4-methylsulfanylphenyl)-2,5-dihydro-2-furanone;

4-(3-Methyl-4-methylsulfonylphenyl)-3-(4-isobutylphenyl)-2,5-dihydro-2-furanone;

4-(3-Methyl-4-methylsulfanylphenyl)-3-(4-trifluoromethylphenyl)-2,5-dihydro-2-furanone;

4-(3-Methyl-4-methylsulfonylphenyl)-3-(4-trifluorophenyl)-2,5-dihydro-2-furanone;

4-(2-Fluoro-4-methylsulfanylphenyl)-3-phenyl-2,5-dihydro-2-furanone;

4-(2-Fluoro-4-methylsulfonylphenyl)-3-phenyl-2,5-dihydro-2-furanone;

4-(4-Methylsulfanyl-3-chlorophenyl)-3-phenyl-2,5-dihydro-2-furanone;

3-(4-Methylsulfanylphenyl)-4-(3-chloro-4-methylsulfanylphenyl)-2,5-dihydro-2-furanone;

4-(4-Methylsulfanyl-3-chlorophenyl)-3-(3,4-difluorophenyl)-2,5-dihydro-2-furanone;

4-(4-Methylsulfanyl-3-fluorophenyl)-3-phenyl-2,5-dihydro-2-furanone;

4-(4-Methylsulfanyl-3-fluorophenyl)-3-(4-methylsulfanylphenyl)-2,5-dihydro-2-furanone;

4-(4-Methylsulfonyl-3-chlorophenyl)-3-phenyl-2,5-dihydro-2-furanone;

4-(4-Methylsulfanyl-3-chlorophenyl)-3-(4-methylphenyl)-2,5-dihydro-2-furanone;

4-(4-Methylsulfanyl-3-fluorophenyl)-3-(4-methylphenyl)-2,5-dihydro-2-furanone;

4-(4-Methylsulfonyl-3-fluorophenyl)-3-phenyl-2,5-dihydro-2-furanone;

4-(4-Methylsulfonyl-3-chlorophenyl)-3-(4-methylphenyl)-2,5-dihydro-2-furanone;

4-(4-Methylsulfonyl-3-fluorophenyl)-3-(4-methylphenyl)-2,5-dihydro-2-furanone;

4-(2-Fluoro-4-methylsulfanylphenyl)-3-(4-trifluoromethylphenyl)-2,5-dihydro-2-furanone;

4-(2-Fluoro-4-methylsulfonylphenyl)-3-(4-trifluoromethylphenyl)-2,5-dihydro-2-furanone;

4-(3-Methyl-4-methylsulfonylphenyl)-3-(4-methylsulfanylphenyl)-2,5-dihydro-2-furanone;

4-(2-Fluoro-4-methylsulfonylphenyl)-3-(4-methylphenyl)-2,5-dihydro-2-furanone;

4-(2-Fluoro-4-methylsulfanylphenyl)-3-(4-isobutylphenyl)-2,5-dihydro-2-furanone;

4-(2-Fluoro-4-methylsulfonylphenyl)-3-(4-isobutylphenyl)-2,5-dihydro-2-furanone;

4-(3-Methyl-4-methylsulfonylphenyl)-3-(4-methoxyphenyl)-2,5-dihydro-2-furanone;

4-(4-Methylsulfanyl-3-fluorophenyl)-3-(4-methoxyphenyl)-2,5-dihydro-2-furanone;

4-(4-Methylsulfonyl-3-fluorophenyl)-3-(4-methoxyphenyl)-2,5-dihydro-2-furanone;

4-(4-Methylsulfonyl-2-chlorophenyl)-3-(4-methoxyphenyl)-2,5-dihydro-2-furanone;

4-(2-Fluoro-4-methylsulfonylphenyl)-3-(3-methyl-4-methylsulfanylphenyl)-2,5-dihydro-2-furanone;

4-(2-Fluoro-4-methylsulfanylphenyl)-3-(4-fluorophenyl)-2,5-dihydro-2-furanone;

4-(4-Methylsulfonyl-3-chlorophenyl)-3-(3,4-difluorophenyl)-2,5-dihydro-2-furanone;

4-(4-Methylsulfanyl-2-chlorophenyl)-3-(4-methoxyphenyl)-2,5-dihydro-2-furanone;

4-(2-Fluoro-4-methylsulfonylphenyl)-3-(4-fluorophenyl)-2,5-dihydro-2-furanone;

4-(2,3-Dimethyl-4-methylsulfonylphenyl)-3-phenyl-2,5-dihydro-2-furanone;

4-(3-Fluoro-4-methylsulfanylphenyl)-3-(3-methyl-4-sulfanylphenyl)-2,5-dihydro-2-furanone;

4-(3-Fluoro-4-methylsulfonylphenyl)-3-(3-methyl-4-methylsulfonylphenyl)-2,5-dihydro-2-furanone;

4-(3-Methyl-4-methylsulfonylphenyl)-3-(3-fluoro-4-methylphenyl)-2,5-dihydro-2-furanone;

4-(3-Methyl-4-methylsulfonylphenyl)-3-(4-ethylphenyl)-2,5-dihydro-2-furanone;

4-(3-Methyl-4-methylsulfonylphenyl)-3-(3,4-dimethylphenyl)-2,5-dihydro-2-furanone;

4-(3-Methyl-4-methylsulfonylphenyl)-3-(3-bromo-4-methoxyphenyl)-2,5-dihydro-2-furanone;

4-(2-Fluoro-4-methylsulfonylphenyl)-3-(3-fluorophenyl)-2,5-dihydro-2-furanone;

4-(3-Fluoro-4-methylsulfonylphenyl)-3-(3-methyl-4-methylsulfanylphenyl)-2,5-dihydro-2-furanone;

4-(2-Fluoro-4-methylsulfonylphenyl)-3-(1-naphthyl)-2,5-dihydro-2-furanone;

3-(3-Methyl-4-methoxyphenyl)-4-(3-methyl-4-methylsulfonylphenyl)-2,5-dihydro-2-furanone;

4-(3-Fluoro-4-methylsulfonylphenyl)-3-(4-fluorophenyl)-2,5-dihydro-2-furanone;

4-(3-Fluoro-4-methylsulfonylphenyl)-3-(3-methyl-4-methoxyphenyl)-2,5-dihydro-2-furanone;

4-(2-Fluoro-4-methylsulfonylphenyl)-3-(3-methyl-4-methoxyphenyl)-2,5-dihydro-2-furanone;

4-(2-Fluoro-4-methylsulfonylphenyl)-3-(3-fluorophenyl)-5,5-dimethyl-2,5-dihydro-2-furanone;

4-(2-Fluoro-4-methylsulfonylphenyl)-3-(4-fluorophenyl)-5,5-dimethyl-2,5-dihydro-2-furanone;

4-(2-Fluoro-4-methylsulfonylphenyl)-3-(3-methyl-4-methoxyphenyl)-5,5-dimethyl-2,5-dihydro-2-furanone;

4-(3-Methyl-4-methylsulfonylphenyl)-3-(3-fluorophenyl)-5,5-dimethyl-2,5-dihydro-2-furanone;

4-(3-Bromomethyl-4-methylsulfonylphenyl)-3-(4-fluorophenyl)-5,5-dimethyl-2,5-dihydro-2-furanone;

2-{5-[4-(4-Fluorophenyl)-2,2-dimethyl-5-oxo-2,5-dihydro-3-furanyl]-2-methylsulfonyl benzyl}-2,3-dihydrobenzo[d]isothiazol-3-oxo-1,1-dioxide;

4-(2-Fluoro-4-methylsulfonylphenyl)-5,5-dimethyl-3-(3-methyl-4-methylsulfonyl phenyl)-2,5-dihydro-2-furanone;

5-Ethyl-4-(3-fluoro-4-methylsulfonylphenyl)-3-(3-fluorophenyl)-2,5-dihydro-2-furanone;

3-(4-Fluorophenyl)-5,5-dimethyl-4-(4-methylsulfonyl-3-morpholinomethylphenyl)-2,5-dihydro-2-furanone;

5-Ethyl-4-(3-fluoro-4-methylsulfonylphenyl)-3-(4-fluorophenyl)-2,5-dihydro-2-furanone;

3-(3,4-Difluorophenyl)-4-(2-fluoro-4-methylsulfonylphenyl)-2,5-dihydro-2-furanone;

3-(3,5-Difluorophenyl)-4-(2-fluoro-4-methylsulfonylphenyl)-2,5-dihydro-2-furanone;

5-Ethyl-4-(3-fluoro-4-methylsulfonylphenyl)-3-(3-methyl-4-methylsulfanylphenyl)-2,5-dihydro-2-furanone;

3-Isopropoxy-5,5-dimethyl-4-(3-methyl-4-methylsulfonylphenyl)-2,5-dihydro-2-furanone;

4-(3-Hydroxymethyl-4-methylsulfonylphenyl)-3-isopropoxy-5,5-dimethyl-2,5-dihydro-2-furanone;

5-Ethyl-4-(3-fluoro-4-methylsulfonylphenyl)-3-(3-methyl-4-methylsufanylphenyl)-5-hydroxy-2,5-dihydro-2-furanone;

5-Ethyl-4-(3-fluoro-4-methylsulfonylphenyl)-3-(4-methoxy-3-methylphenyl)-2,5-dihydro-2-furanone;

5-Ethyl-4-(3-fluoro-4-methylsulfonylphenyl)-3-(3,4-difluorophenyl)-2,5-dihydro-2-furanone;

3-(3,4-Difluorophenyl)-5-ethyl-4-(2-fluoro-4-methylsulfonylphenyl)-2,5-dihydro-2-furanone;

3-(3,4-Difluorophenyl)-5-ethyl-4-(2-fluoro-4-methylsulfonylphenyl)-5-hydroxy-2,5-dihydro-2-furanone;

4-(3-Fluoromethyl-4-methylsulfonylphenyl)-3-isopropoxy-5,5-dimethyl-2,5-dihydro-2-furanone;

3-Isopropoxy-5,5-dimethyl-4-(3-fluoro-4-methylsulfonylphenyl)-2,5-dihydro-2-furanone;

3-Isopropoxy-5,5-dimethyl-4-(3-methylsulfanyl-4-methylsulfonylphenyl)-2,5-dihydro-2-furanone;

3-Isopropoxy-4-(3-methoxymethyl-4-methylsulfonylphenyl)-5,5-dimethyl-2,5-dihydro-2-furanone;

4-(3-Formyl-4-methylsulfonylphenyl)-3-isopropoxy-5,5-dimethyl-2,5-dihydro-2-furanone;

4-(3-Fluoro-4-methylsulfonylphenyl)-3-(3-methyl-4-methylsulfonylphenyl)-2,5-dihydro-2-furanone;

5-Ethyl-4-(2-fluoro-4-methylsulfonylphenyl)-3-(4-fluorophenyl)-5-hydroxy-2,5-dihydro-2-furanone;

5-Ethylidene-4-(2-fluoro-4-methylsulfonylphenyl)-3-(3-fluorophenyl)-2,5-dihydro-2-furanone;

5-Ethylidene-4-(2-fluoro-4-methylsulfonylphenyl)-3-phenyl-2,5-dihydro-2-furanone;

5-Ethylidene-4-(2-fluoro-4-methylsulfonylphenyl)-3-(3-methyl-4-methoxyphenyl)-2,5-dihydro-2-furanone;

4-(3-Fluoro-4-methylsulfonylphenyl)-3-(4-fluorophenyl)-5-methyl-2,5-dihydro-2-furanone;

4-(3-Fluoro-4-methylsulfonylphenyl)-3-(3-fluorophenyl)-5-methyl-2,5-dihydro-2-furanone;

4-(2-Fluoro-4-methylsulfonylphenyl)-3-(4-fluorophenyl)-5-methyl-2,5-dihydro-2-furanone;

4-(2-Fluoro-4-methylsulfonylphenyl)-3-(3-fluorophenyl)-5-methyl-2,5-dihydro-2-furanone;

4-(2-Fluoro-4-methylsulfonylphenyl)-3-(3,4-difluorophenyl)-5-methyl-2,5-dihydro-2-furanone;

4-(2-Fluoro-4-methylsulfonylphenyl)-3-(3-fluorophenyl)-5-methoxy-5-methyl-2,5-dihydro-2-furanone;

4-(2-Fluoro-4-methylsulfonylphenyl)-3-(4-methylphenyl)-5-methyl-2,5-dihydro-2-furanone;

4-(2-Fluoro-4-methylsulfonylphenyl)-3-(4-fluorophenyl)-5-methoxy-5-methyl-2,5-dihydro-2-furanone;

1-(4-Fluorophenyl)-4-(3-methyl-4-methylsulfonylphenyl)-3-phenyl-2,5-dihydro-1H-2-azolone and 3-(2-Fluoro-4-methylsulfonylphenyl)-1-(4-fluorophenyl)-4-phenyl-2,5-dihydro-1H-2,5-azoledione.

11. A compound according to claim 1 wherein in the pharmaceutically acceptable salt is selected from Li, Na, K, Ca, Mg, Fe, Cu, Zn, Mn; salts of organic bases such as N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine or spermidine; chiral bases like alkylphenylamine, glycinol or phenyl glycinol; salts of natural amino acids selected from glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids selected from D-isomers or substituted amino acids; guanidine, substituted guanidine wherein the substituents are selected from nitro, amino, alkyl, alkenyl, alkynyl, ammonium or substituted ammonium salts and aluminum salts, salts may include acid addition salts where appropriate which are, sulphates, nitrates, phosphates, perchlorates, borates, halides, acetates, tartrates, maleates, citrates, succinates, palmoates, methanesulphonates, benzoates, salicylates, hydroxynaphthoates, benzenesulfonates, ascorbates, glycerophosphates or ketoglutarates.

12. A pharmaceutical composition, which comprises a compound of formula (I)

(I)

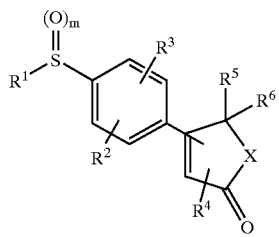

as defined in claim 1 and a pharmaceutically acceptable carrier, diluent, excipient or solvate.

13. A pharmaceutical composition as claimed in claim 12 in the form of a tablet, capsule, powder, syrup, solution or suspension.

14. A pharmaceutical composition which comprises a compound of formula (I) as defined in claim 1 and acetaminophen, phenacetin, caffeine, a $H_2$ antagonist, aluminum or magnesium hydroxide, simethicone, phenylephrine, phenyl propanolamine, pseudophedrine, oxymetazoline, epinephrine, nephazoline, propylhexadrine or levo-desoxyephedrine, xylomatazoline, a sedating or non sedating antihistamine, dextromethorphan, carbetapentane, caramiphen, hydrocodeine, codeine, or a diuretic agent or a combination thereof and a pharmaceutically acceptable carrier, diluent, excipient or solvate.

15. A method of treating inflammation, pyrexia, arthritis, pain, Alzheimer disease, dysmenorrhea, premature labor, asthma, bronchitis, inflammatory bowel disease, prostanoid-induced smooth muscle contraction, gastritis, irritable bowel syndrome, Crohn's disease, ulcerative colitis, diverticulitis, regional enteritis, peptic ulcers, cancer, bacterial infections, skin inflammation disorders, allergic rhinitis, respiratory distress syndrome, endotoxin shock syndrome, atherosclerosis, or ophthalmic diseases, comprising administering a therapeutically effective amount of a compound of formula (I) as claimed in claim 1 to a mammal in need thereof.

16. A method according to claim 15, wherein the pain is caused due to premature labor, back and neck pain, head ache, tooth ache, sprains, muscular pain, strains, myostis, neuralgia, synovitis, bursitis, tendinitis, injuries following surgical and dental procedures, pain from cancer, or post-operative pain.

17. A method according to claim 15, wherein the inflammation is caused due to common cold, influenza, viral infections, pulmonary inflammation, post-operative inflammation, skin inflammation, inflammation, vascular diseases, migraine head aches, periarteritis nodosa, thyroiditis, aplastic anemia, Behcat's syndrome, Hodgkin's diseases, scleroderma, myasthenia gravies, sarcoidosis, nephrotic syndrome, Type I diabetes, polymyositis, conjunctivitis, gingivitis, myocardial ischaemia, nephritis, swelling after injury, or hypersensitivity.

18. A method according to claim 15, wherein the arthritis is selected from rheumatoid arthritis, osteoarthritis, gouty arthritis, juvenile arthritis, or spondylo arthritis.

19. A method according to claim 15, for the treatment of inflammation, pyrexia, arthritis, pain, Alzheimer disease, dysmenorrhea, premature labor, asthma, bronchitis, inflammatory bowel disease, prostanoid-induced smooth muscle contraction, gastritis, irritable bowel syndrome, Crohn's disease, ulcerative colitis, diverticulitis, regional enteritis, peptic ulcers, cancer, bacterial infections, skin inflammation disorders such as eczema, burns, dermatitis, psoriasis, allergic rhinitis, respiratory distress syndrome, endotoxin shock syndrome, atherosclerosis, or ophthalmic diseases, wherein the compound of formula (I) is a cyclooxygenase inhibitor.

20. A method according to claim 18, wherein the compound of formula (I) is a cyclooxygenase 2 inhibitor.

21. A method of treating inflammation, pyrexia, arthritis, pain, Alzheimer disease, dysmenorrhea, premature labor, asthma, bronchitis, inflammatory bowel disease, prostanoid-induced smooth muscle contraction, gastritis, irritable bowel syndrome, Crohn's disease, ulcerative colitis, diverticulitis, regional enteritis, peptic ulcers, cancer, bacterial infections, skin inflammation disorder, allergic rhinitis, respiratory distress syndrome, endotoxin shock syndrome, atherosclerosis, or ophthalmic disease, comprising administering a therapeutically effective amount of a pharmaceutical composition as claimed in claim 14 to a mammal in need thereof.

22. A pharmaceutical composition, which comprises a compound as claimed 10 and a pharmaceutically acceptable carrier, diluent, excipient or solvate.

23. A pharmaceutical composition as claimed in claim 22 in the form of a tablet, capsule, powder, syrup, solution or suspension.

24. A pharmaceutical composition which comprises a compound as claimed in claim 10 and acetaminophen, phenacetin, caffeine, a $H_2$ antagonist, aluminum or magnesium hydroxide, simethicone, phenylephrine, phenyl propanolamine, pseudophedrine, oxymetazoline, epinephrine, nephazoline, propylhexadrine or levo-desoxyephedrine, xylomatazoline, a sedating or non sedating antihistamine, dextromethorphan, carbetapentane, caramiphen, hydrocodeine, codeine, or a diuretic agent or a combination thereof and a pharmaceutically acceptable carrier, diluent, excipient or solvate.

25. A method of treating inflammation, pyrexia, arthritis, pain, Alzheimer disease, dysmenorrhea, premature labor, asthma, bronchitis, inflammatory bowel disease, prostanoid-induced smooth muscle contraction, gastritis, irritable bowel syndrome, Crohn's disease, ulcerative colitis, diverticulitis, regional enteritis, peptic ulcers, cancer, bacterial infections, skin inflammation disorder, allergic rhinitis, respiratory distress syndrome, endotoxin shock syndrome, atherosclerosis, or ophthalmic disease comprising administering a therapeutically effective amount of a compound as claimed in claim 10 to a mammal in need thereof.

26. A method according to claim 25, wherein the said pain is caused due to premature labor, back and neck pain, head ache, tooth ache, sprains, muscular pain, strains, myostis, neuralgia, synovitis, bursitis, tendinitis, injuries following surgical and dental procedures, pain from cancer, or post-operative pain.

27. A method according to claim 25, wherein the inflammation is caused due to common cold, influenza, viral infections, pulmonary inflammation, post-operative inflammation, skin inflammation, inflammation, vascular disease, migraine head aches, periarteritis nodosa, thyroiditis, aplastic anemia, Behcat's syndrome, Hodgkin's diseases, scleroderma, myasthenia gravies, sarcoidosis, nephrotic syndrome, Type I diabetes, polymyositis, conjunctivitis, gingivitis, myocardial ischaemia, nephritis, swelling after injury, or hypersensitivity.

28. A method according to claim 25, wherein the arthritis is selected from rheumatoid arthritis, osteoarthritis, gouty arthritis, juvenile arthritis, or spondylo arthritis.

29. A method according to claim 25, for the treatment of inflammation, pyrexia, arthritis, pain, Alzheimer disease, dysmenorrhea, premature labor, asthma, bronchitis, inflammatory bowel disease, prostanoid-induced smooth muscle contraction, gastritis, irritable bowel syndrome, Crohn's disease, ulcerative colitis, diverticulitis, regional enteritis, peptic ulcers, cancer, bacterial infections, skin inflammation disorder, allergic rhinitis, respiratory distress syndrome, endotoxin shock syndrome, atherosclerosis, or ophthalmic diseases wherein the compound of claim 10 is a cyclooxygenase inhibitor.

30. A method of treating inflammation, pyrexia, arthritis, pain, Alzheimer disease, dysmenorrhea, premature labor, asthma, bronchitis, inflammatory bowel disease, prostanoid-induced smooth muscle contraction, gastritis, irritable bowel syndrome, Crohn's disease, ulcerative colitis, diverticulitis, regional enteritis, peptic ulcers, cancer, bacterial infections, skin inflammation disorders, allergic rhinitis, respiratory distress syndrome, endotoxin shock syndrome, atherosclerosis, or ophthalmic diseases comprising administering a therapeutically effective amount of a pharmaceutical composition as claimed in claim 23 to a mammal in need thereof.

31. A method of treating inflammation, pyrexia, arthritis, pain, Alzheimer disease, dysmenorrhea, premature labor, asthma, bronchitis, inflammatory bowel disease, prostanoid-induced smooth muscle contraction, gastritis, irritable bowel syndrome, Crohn's disease, ulcerative colitis, diverticulitis, regional enteritis, peptic ulcers, cancer, bacterial infections, skin inflammation disorders, allergic rhinitis, respiratory distress syndrome, endotoxin shock syndrome, atherosclerosis, or ophthalmic diseases comprising administering a therapeutically effective amount of a pharmaceutical composition as claimed in claim 24 to a mammal in need thereof.

32. A method according to claim 30, wherein the said pain is caused due to premature labor, back and neck pain, head ache, tooth ache, sprains, muscular pain, strains, myostis, neuralgia, synovitis, bursitis, tendinitis, injuries following surgical and dental procedures, pain from cancer, or post-operative pain.

33. A method according to claim 31, wherein the said pain is caused due to premature labor, back and neck pain, head ache, tooth ache, sprains, muscular pain, strains, myostis, neuralgia, synovitis, bursitis, tendinitis, injuries following surgical and dental procedures, pain from cancer, or post-operative pain.

34. A method according to claim 30, wherein the inflammation is caused due to common cold, influenza, viral infections, pulmonary inflammation, post-operative inflammation, skin inflammation, inflammation, vascular disease, migraine head aches, periarteritis nodosa, thyroiditis, aplastic anemia, Behcat's syndrome, Hodgkin's diseases, scleroderma, myasthenia gravies, sarcoidosis, nephrotic syndrome, Type I diabetes, polymyositis, conjunctivitis, gingivitis, myocardial ischaemia, nephritis, swelling after injury, or hypersensitivity.

35. A method according to claim 31, wherein the inflammation is caused due to common cold, influenza, viral infections, pulmonary inflammation, post-operative inflammation, skin inflammation, inflammation, vascular disease, migraine head aches, periarteritis nodosa, thyroiditis, aplastic anemia, Behcat's syndrome, Hodgkin's diseases, scleroderma, myasthenia gravies, sarcoidosis, nephrotic syndrome, Type I diabetes, polymyositis, conjunctivitis, gingivitis, myocardial ischaemia, nephritis, swelling after injury, or hypersensitivity.

36. A method according to claim 30, wherein the arthritis is selected from rheumatoid arthritis, osteoarthritis, gouty arthritis, juvenile arthritis, or spondylo arthritis.

37. A method according to claim 31, wherein the arthritis is selected from rheumatoid arthritis, osteoarthritis, gouty arthritis, juvenile arthritis, or spondylo arthritis.

38. A method according to claim 15, wherein the ophthalmic desease is retinitis, retinopathy, uveitis, ocular photophobia or acute injury to eye tissue.

39. A method according to claim 21, wherein the ophthalmic desease is retinitis, retinopathy, uveitis, ocular photophobia or acute injury to eye tissue.

40. A method according to claim 25, wherein the ophthalmic desease is retinitis, retinopathy, uveitis, ocular photophobia or acute injury to eye tissue.

41. A method according to claim 29, wherein the ophthalmic desease is retinitis, retinopathy, uveitis, ocular photophobia or acute injury to eye tissue.

42. A method according to claim 30, wherein the ophthalmic desease is retinitis, retinopathy, uveitis, ocular photophobia or acute injury to eye tissue.

43. A method according to claim 31, wherein the ophthalmic desease is retinitis, retinopathy, uveitis, ocular photophobia or acute injury to eye tissue.

44. A method according to claim 15, wherein the skin inflammation disorder is eczema, burns, dermatitis or psoriasis.

45. A method according to claim 21, wherein the skin inflammation disorder is eczema, burns, dermatitis or psoriasis.

46. A method according to claim 25, wherein the skin inflammation disorder is eczema, burns, dermatitis or psoriasis.

47. A method according to claim 29, wherein the skin inflammation disorder is eczema, burns, dermatitis or psoriasis.

48. A method according to claim 30, wherein the skin inflammation disorder is eczema, burns, dermatitis or psoriasis.

49. A method according to claim 31, wherein the skin inflammation disorder is eczema, burns, dermatitis or psoriasis.

* * * * *